US012791547B2

(12) United States Patent
Wang et al.

(10) Patent No.: US 12,791,547 B2
(45) Date of Patent: Nov. 10, 2026

(54) WELL EVALUATION USING WATER CHEMISTRY ANALYSIS

(71) Applicant: Chevron U.S.A. Inc., San Ramon, CA (US)

(72) Inventors: Wei Wang, Houston, TX (US); Wei Wei, Sugar Land, TX (US); Jason Robert Parizek, Midland, TX (US); Yuguang Chen, Bellaire, TX (US); Baosheng Liang, Houston, TX (US); Christopher Thomas Lannen, Houston, TX (US)

(73) Assignee: CHEVRON U.S.A. INC., San Ramon, CA (US)

( * ) Notice: Subject to any disclaimer, the term of this patent is extended or adjusted under 35 U.S.C. 154(b) by 396 days.

(21) Appl. No.: 18/525,073

(22) Filed: Nov. 30, 2023

(65) Prior Publication Data

US 2024/0410873 A1 Dec. 12, 2024

Related U.S. Application Data

(60) Provisional application No. 63/472,337, filed on Jun. 11, 2023.

(51) Int. Cl.
*G01N 33/28* (2006.01)
*E21B 43/26* (2006.01)
*E21B 49/08* (2006.01)

(52) U.S. Cl.
CPC ....... *G01N 33/2823* (2013.01); *E21B 49/086* (2013.01); *G01N 33/2847* (2013.01); *E21B 43/26* (2013.01); *E21B 2200/20* (2020.05)

(58) Field of Classification Search
CPC ............ G01N 33/2823; G01N 33/2847; E21B 49/086; E21B 43/26; E21B 2200/20
See application file for complete search history.

(56) References Cited

U.S. PATENT DOCUMENTS 9,528,874 B2 * 12/2016 Larter ...................... E21B 49/10
11,421,148 B1 * 8/2022 Al-Yousif .............. C09K 8/584
(Continued)

FOREIGN PATENT DOCUMENTS

CN 109312615 A * 2/2019 ......... G01N 33/2835

OTHER PUBLICATIONS

M. Baker et al., Well Design and Well Spacing Optimisation In Unconventional Plays, Society of Petroleum Engineers, SPE 159325, Presented at SPE Asia Pacific Oil and Gas Conference and Exhibition, Perth, Australia, Oct. 22-24, 2012, 22 pages.
(Continued)

*Primary Examiner* — Raul J Rios Russo
*Assistant Examiner* — Carl F.R. Tchatchouang
(74) *Attorney, Agent, or Firm* — Smith & Woldesenbet Law Group, PLLC

(57) ABSTRACT

A method for evaluating multiple wells using water chemistry analysis may include testing a parameter associated with a first sample obtained from each of the wells over a period of time prior to implementing the field operation of the well. The method may also include generating a baseline of the parameter associated with the first samples for each of the wells. The method may further include testing the parameter associated with second samples obtained from each of the wells during the field operation of the well. The method may also include determining a difference in the parameter between the baseline and results of testing the second samples for at least one of the wells, where the difference exceeds a threshold parameter value for the parameter, and where the difference includes a characterization of water saturation.

20 Claims, 20 Drawing Sheets

(56) References Cited

U.S. PATENT DOCUMENTS

| | | | | |
|---|---|---|---|---|
| 2012/0247759 | A1* | 10/2012 | Manrique | C09K 8/602 166/270.1 |
| 2015/0088424 | A1* | 3/2015 | Burlakov | G01V 1/40 702/6 |
| 2022/0155275 | A1* | 5/2022 | Zuo | G01N 30/8693 |

OTHER PUBLICATIONS

F. Lalehrokh et al., Well Spacing Optimization In Eagle Ford, Society of Petroleum Engineers, SPE 171640-MS, Presented at the SPE/CSUR Unconventional Resources Conference—Canada, Calgary, Alberta, Canada, Sep. 30-Oct. 2, 2014, 11 pages.

Hongjie Xiong et al., Optimizing Well Completion Design and Well Spacing With Integration of Advanced Multi-Stage Fracture Modeling & Reservoir Simulation—A Permian Basin Case Study, Society of Petroleum Engineers, SPE 189855-MS, Presented at the SPE Hydraulic Fracturing Technology Conference & Exhibition, The Woodlands, Texas, USA, Jan. 23-25, 2018, 21 pages.

Chigozie Aniemena et al., Well Spacing Optimization In Shale Reservoirs Using Rate Transient Analytics, Unconventional Resources Technology Conference, URTeC 2019-278, Presented at the Unconventional Resources Technology Conference, Denver, Colorado, USA, Jul. 22-24, 2019, 20 pages.

Do Shin et al., Optimizing Vertical and Lateral Spacing of Horizontal Wells In Permian Basin Stacked Bench Developments, Unconventional Resources Technology Conference, URTeC 2669025, Presented at the Unconventional Resources Technology Conference, Austin, Texas, USA, Jul. 24-26, 2017, 18 pages.

Baosheng Liang et al., Fracture Hit Monitoring and Its Mitigation Through Integrated 3D Modeling In the Wolfcamp Stacked Pay In the Midland Basin, Unconventional Resources Technology Conference, URTeC 2671336, Presented at the Unconventional Resources Technology Conference, Austin, Texas, USA, Jul. 24-26, 2017, 16 pages.

Baosheng Liang et al., Subsurface Well Spacing Optimization In the Permian Basin, Unconventional Resources Technology Conference, URTeC 2671346, Presented at the Unconventional Resources Technology Conference, Austin, Texas, USA, Jul. 24-26, 2017, 12 pages.

Mehdi Rafiee et al., Well Spacing Optimization In Eagle Ford Shale: An Operator's Experience, Unconventional Resources Technology Conference, URTeC 2695433, Presented at the Unconventional Resources Technology Conference, Austin, Texas, USA, Jul. 24-26, 2017, 23 pages.

Wei Wang et al., Subsurface Scale Diagnosis and Remediation of Uplift Oil Production, Society of Petroleum Engineers, SPE 209490-MS, Presented at SPE International Oilfield Scale Conference and Exhibition, Aberdeen, Scotland, UK, May 25-26, 2022, 9 pages.

* cited by examiner

1397

1497

1597

1697

1797

1897

1997

2097

2197

2297

2397

2497

3197

WELL EVALUATION USING WATER CHEMISTRY ANALYSIS

CROSS-REFERENCE TO RELATED APPLICATIONS

This application claims priority under 35 U.S.C. § 119 to U.S. Provisional Patent Application Ser. No. 63/472,337, titled "Well Evaluation Using Water Chemistry Analysis" and filed on Jun. 11, 2023, the entire contents of which are hereby incorporated herein by reference.

TECHNICAL FIELD

The present application is related to subterranean field operations and, more particularly, to well evaluation using water chemistry analysis.

BACKGROUND

Hydrocarbon resources (e.g., oil, natural gas) in subterranean reservoirs, such as with unconventional reservoirs, may be more easily accessed and collected using horizontal drilling and fracturing technologies. Fracturing, such as hydraulic fracturing, involves the injection of large quantities of fluid, which includes water and chemical additives, into a reservoir to create a fracture network that provides pathways for the hydrocarbon resources to flow.

Wells drilled into unconventional reservoirs may be hydraulically fractured to produce meaningful quantities of hydrocarbon from their low permeability reservoirs. When new wells are fractured near existing wells, for example, fracture-driven interactions may occur. Fracture-driven interactions may include unintended interactions between nearby wells that may occur during hydraulic fracturing. These fracture-driven interactions may create a number of different issues, including, reducing hydrocarbon production. Thus, there is a need in the art in the context of evaluating wells.

SUMMARY

In general, in one aspect, the disclosure relates to a method for evaluating a plurality of wells using water chemistry analysis. The method may include testing, using the water chemistry analysis, a parameter associated with a first sample obtained from each of the plurality of wells over a period of time prior to implementing a field operation of a well of the plurality of wells, where the first sample includes water. The method may also include generating, based on results of testing the parameter associated with the first samples, a baseline of the parameter associated with the first samples for each of the plurality of wells. The method may further include testing, using the water chemistry analysis, the parameter associated with a second sample obtained from each of the plurality of wells during the field operation of the well, where the second sample includes water. The method may also include determining a difference in the parameter between the baseline and results of testing the second sample for at least one of the plurality of wells, where the difference exceeds a threshold parameter value for the parameter, and where the difference includes a characterization of water saturation.

In another aspect, the disclosure relates to a system for evaluating a plurality of wells using water chemistry analysis. The system may include a plurality of wells from which initial samples and subsequent samples are obtained. The system may also include a fluid source that is configured to provide a field operation fluid that is used in a field operation for one of the plurality of wells. The system may further include an analytic system that includes a testing apparatus and a controller communicably coupled to the testing apparatus. The testing apparatus of the analytic system may be configured to test, using the water chemistry analysis, a parameter associated with the initial sample obtained from each of the plurality of wells over a period of time prior to implementing the field operation of the one of the plurality of wells, where the initial sample includes water. The testing apparatus of the analytic system may also be configured to test, using the water chemistry analysis, the parameter associated with the subsequent samples obtained from the plurality of wells during the field operation of the one of the plurality of wells, where the subsequent samples include water. The controller of the analytic system may be configured to generate, based on results of testing the parameter associated with the initial samples, a baseline of the parameter associated with initial samples for each of the plurality of wells. The controller of the analytic system may also be configured to determine a difference in the parameter between the baseline and results of testing the subsequent samples for at least one of the plurality of wells, where the difference exceeds a threshold parameter value for the parameter, and where the difference includes a characterization of water saturation.

In yet another aspect, the disclosure relates to a method for evaluating a well using water chemistry analysis. The method may include testing, using the water chemistry analysis, a parameter associated with a plurality of first samples obtained from the well over a period of time prior to implementing a field operation. The method may also include generating, based on results of testing the parameter associated with the plurality of first samples, a baseline of the parameter associated with the plurality of first samples for the well. The method may further include testing, using the water chemistry analysis, the parameter associated with a second sample obtained from the well during the field operation. The method may also include determining a difference in the parameter between the baseline and results of testing the second sample for the well, where the difference exceeds a threshold parameter value for the parameter, and where the difference includes a characterization of water saturation.

These and other aspects, objects, features, and embodiments will be apparent from the following description and the appended claims.

BRIEF DESCRIPTION OF THE DRAWINGS

The drawings illustrate only example embodiments and are therefore not to be considered limiting in scope, as the example embodiments may admit to other equally effective embodiments. The elements and features shown in the drawings are not necessarily to scale, emphasis instead being placed upon clearly illustrating the principles of the example embodiments. Additionally, certain dimensions or positions may be exaggerated to help visually convey such principles. In the drawings, the same reference numerals used in different figures may designate like or corresponding but not necessarily identical elements.

DETAILED DESCRIPTION

Figure 1:
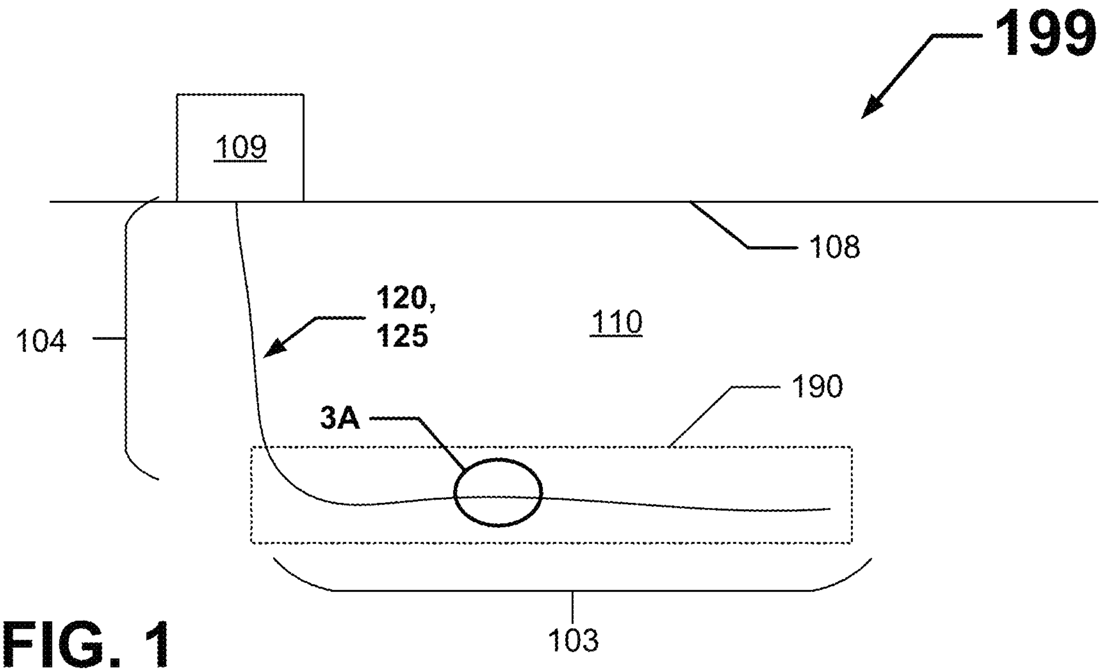
FIG. 1 shows a field system in which example embodiments may be used.

The example embodiments discussed herein are directed to systems, apparatus, methods, and devices for well evaluation using water chemistry analysis. In some cases, use of example embodiments may allow for field operations that occur at the subsurface (e.g., in a fractured subterranean formation adjacent to a well) to be evaluated, which may lead to additional subterranean resources being extracted from the subsurface and/or increasing the injection capacity and life of a saltwater disposal (SWD) well. Examples of such additional subterranean resources may include, but are not limited to, oil and natural gas. Use of example embodiments on production and injection wells may be designed to comply with certain standards and/or requirements. Example embodiments may be used for wellbores drilled in conventional and/or unconventional (e.g., tight shale) subterranean formations and reservoirs. Example embodiments of well evaluation using water chemistry analysis (e.g., for injection SWD wells, for production wells) may be at a subsurface (e.g., within and adjacent to a wellbore in a subterranean formation) for injection (e.g., SWD) wells and production wells (e.g., wells undergoing a fracturing operation).

Supplemental information about well evaluation using water chemistry analysis according to example embodiments may be found in two appendices that accompany this document. One Appendix is a technical paper entitled "Time-lapse Produced Water Source Allocation: Characterizing Impact of Fracture-Driven Interaction, Insights on Life-of-Well Water Cut Trends and Asset Development Optimization in the Permian Midland Basin" written by Wei Wang et al. for the Unconventional Resources Technology Conference held in Denver Colorado, U.S.A. from 13-15 Jun. 2023 (URTeC: 3858760), 13 pages. The other Appendix is a presentation titled "Time-lapse Produced Water Source Allocation: Characterizing Impact of Fracture-Driven Interaction (FDI), Insights on Life-of-Well Water Production Profile and Asset Development Optimization in the Permian Midland Basin", created by Wei Wang et al, and presented on 15 Jun. 2023 at the Unconventional Resources Technology Conference held in Denver Colorado, U.S.A., 16 pages. The entire contents of the above-listed Appendices are hereby incorporated herein by reference.

Example embodiments relate to a water chemistry and production/injection rate-based approach to directly monitor, track, and/or quantify real-time interaction/fluid communication between wells and/or formations. Well evaluation using water chemistry analysis may include determining well placement and/or completion design (e.g., fracture geometry, frac water treatment, frac water composition) of a well (e.g., a new production well, a SWD well). In addition, or in the alternative, well evaluation using water chemistry analysis may be used for key decision making in unconventional (e.g., shale & tight asset development) formations. In addition, or in the alternative, well evaluation using water chemistry analysis may be used to improve water saturation characterization.

In addition, or in the alternative, well evaluation using water chemistry analysis may be used to optimize reservoir simulation and production forecasts/optimization. In addition, or in the alternative, well evaluation using water chemistry analysis may be used for production trouble shooting/root cause analysis for both parent and new wells. In addition, or in the alternative, well evaluation using water chemistry analysis may be used to optimize working conceptual models for water disposal and interaction with producers. Well evaluation using water chemistry analysis may additionally or alternatively include corrosion assessment and control within a well.

Well evaluation using water chemistry analysis according to example embodiments may provide results and insights into one or more of a number of factors related to a well. Such factors may include but are not limited to water geochemistry surveillance (e.g., for SWD wells, for FDI (defined below)), fracturing fluid chemistry and chemical additives, hydrocarbon properties, geoscience considerations (e.g., structural configurations, lithology, stratigraphy methods, gross thickness, net-to-gross ratio, net pay, porosity, saturation, permeability, heterogeneity), engineering considerations (e.g., reservoir depth, pressure, temperature, fluid properties, recovery mechanisms, fluid mobilities, fluid distribution, well productivity), and/or operational considerations (e.g., water depth, well types, completion, spacing, facility type and constraints, artificial lift, pattern type and spacing, injector/producer ratio).

As defined herein, improving well placement involves evaluating one or more aspects of a well so that the placement of that well is optimal for the purpose (e.g., production of subterranean resources, injection of saltwater) for which it and the adjacent wells are designed. Examples of such aspects may include, but are not limited to, horizontal distance between horizontal wellbores, vertical distance between vertical wellbores, number of wellbores drilled and completed in a given volume of reservoir, and the lithologic target in which the well is placed.

As defined herein, improving completion design involves evaluating one or more aspects of the completion design of a well so that such completion design is optimal for the purpose (e.g., production of subterranean resources, injection of saltwater) for which it and the adjacent wells are designed. Examples of such aspects may include, but are not limited to, the volume of water and/or the volume of proppant pumped into each cluster (perforation), each stage (group of clusters), and/or the entire well, the cluster spacing, orientation of perforations within each cluster, perforation diameter (whether or not HCl is used), and the chemical additives.

As defined herein, a sample obtained from a well may be or include one or more of any of a number of materials. A sample obtained from a well may be or include a liquid, a solid, and/or a gas. In certain example embodiments, a sample obtained from a well includes some amount (e.g., trace amounts, 5% by volume or weight, 50% by volume or weight, 75% by volume or weight, 95% by volume or weight) of water. Such water may include one or more elements in addition to hydrogen and oxygen. In implementations, a sample may include produced water, formation water, fracturing fluid (also referred to as frac water), and/or hydrocarbon (e.g., oil).

An FDI may include practically any fluidic interaction involving one or more fractures. For example, the fluidic interaction may be related to fractures generated by hydraulic fracturing. For example, the fluidic interaction may be related to fractures generated from injection, such as saltwater injection. Example embodiments may apply to practically any fluidic interaction, such as those caused by fractures. In one implementation, the fluidic interaction may be between a parent well and a child well. In one implementation, the fluidic interaction may be between a first child well and a second child well. In one implementation, the fluidic interaction may be between a first formation or first zone and a second formation or second zone that both produce water to a single well, such as a saltwater disposal zone above a hydrocarbon producing zone that both produce water into a single well. In one implementation, the fluidic interaction may be between a first formation or first zone and a second formation or second zone that produce water to a single well, such as a saltwater disposal zone below a hydrocarbon producing zone that both produce water into a single well. In one implementation, the fluidic interaction may be between a first formation or first zone and a second formation or second zone that produce water to a single well, such as a saltwater disposal zone above a hydraulic fracturing zone that both produce water into a single well. Potentially, in one implementation, the fluidic interaction may be between a first formation or first zone and a second formation or second zone that produce water to a single well, such as a saltwater disposal zone below a hydraulic fracturing zone that both produce water into a single well. This is not an exhaustive list of fluidic interactions, and example embodiments may be applied to other instances of fluidic interaction (e.g., fluidic interactions with three wells, a well in fluidic interaction with three or more formations/three or more zones, multiple wells in fluidic interaction with two or more formations/two or more zones, etc.).

As defined herein, water may be of any type and/or from any source of water, including but not limited to produced water, formation water, without adding any chemicals or making any other alterations to the water. Alternatively, water may be of any type and/or from any source of water that has added thereto one or more chemicals and/or has otherwise been altered in some way. Examples of such water may include, but are not limited to, water within a fracturing fluid, water with an acid added to it, and water with scale inhibitor added to it. The water may include one or more types of solid-generating components (e.g., bivalent cations, trivalent cations). In addition, the water may include various amounts of total dissolved solids (TDSs) (e.g., between 1,000 mg/L and 500,000 mg/L, between 30,000 mg/L and 100,000 mg/L, between 50,000 mg/L and 250,000 mg/L, between 20,000 mg/L and 50,000 mg/L, between 100,000 mg/L and 200,000 mg/L).

The use of the terms "about", "approximately", and similar terms applies to all numeric values, whether or not explicitly indicated. These terms generally refer to a range of numbers that one of ordinary skill in the art would consider as a reasonable amount of deviation to the recited numeric values (i.e., having the equivalent function or result). For example, this term may be construed as including a deviation of ±10 percent of the given numeric value provided such a deviation does not alter the end function or result of the value. Therefore, a value of about 1% may be construed to be a range from 0.9% to 1.1%. Furthermore, a range may be construed to include the start and the end of the range. For example, a range of 10% to 20% (i.e., range of 10%-20%) includes 10% and also includes 20%, and includes percentages in between 10% and 20%, unless explicitly stated otherwise herein. Similarly, a range of between 10% and 20% (i.e., range between 10%-20%) includes 10% and also includes 20%, and includes percentages in between 10% and 20%, unless explicitly stated otherwise herein.

A "subterranean formation" refers to practically any volume under a surface. For example, it may be practically any volume under a terrestrial surface (e.g., a land surface), practically any volume under a seafloor, etc. Each subsurface volume of interest may have a variety of characteristics, such as petrophysical rock properties, reservoir fluid properties, reservoir conditions, hydrocarbon properties, or any combination thereof. For example, each subsurface volume of interest may be associated with one or more of: temperature, porosity, salinity, permeability, water composition, mineralogy, hydrocarbon type, hydrocarbon quantity, reservoir location, pressure, etc. Those of ordinary skill in the art will appreciate that the characteristics are many, including, but not limited to: shale gas, shale oil, tight gas, tight oil, tight carbonate, carbonate, vuggy carbonate, unconventional formation (e.g., a permeability of less than 25 millidarcy (mD) such as a permeability of from 0.000001 mD to 25 mD)), diatomite, geothermal, mineral, etc.

In some embodiments, the unconventional formation may have a permeability of less than 25 millidarcy (mD) (e.g., 20 mD or less, 15 mD or less, 10 mD or less, 5 mD or less, 1 mD or less, 0.5 mD or less, 0.1 mD or less, 0.05 mD or less, 0.01 mD or less, 0.005 mD or less, 0.001 mD or less, 0.0005 mD or less, 0.0001 mD or less, 0.00005 mD or less, 0.00001 mD or less, 0.000005 mD or less, 0.000001 mD or less, or less). In some embodiments, the unconventional formation may have a permeability of at least 0.000001 mD (e.g., at least 0.000005 mD, at least 0.00001 mD, 0.00005 mD, at least 0.0001 mD, 0.0005 mD, 0.001 mD, at least 0.005 mD, at least 0.01 mD, at least 0.05 mD, at least 0.1 mD, at least 0.5 mD, at least 1 mD, at least 5 mD, at least 10 mD, at least 15 mD, or at least 20 mD).

The unconventional formation may include a permeability ranging from any of the minimum values described above to any of the maximum values described above. For example, in some embodiments, the unconventional formation may have a permeability of from 0.000001 mD to 25 mD (e.g., from 0.001 mD to 25 mD, from 0.001 mD to 10 mD, from 0.01 mD to 10 mD, from 0.1 mD to 10 mD, from 0.001 mD to 5 mD, from 0.01 mD to 5 mD, or from 0.1 mD to 5 mD).

The terms "formation", "subsurface formation", "hydrocarbon-bearing formation", "reservoir", "subsurface reservoir", "subsurface area of interest", "subsurface region of interest", "subsurface volume of interest", and the like may be used synonymously. The term "subterranean formation" is not limited to any description or configuration described herein.

A "well" or a "wellbore" refers to a single hole, usually cylindrical, that is drilled into a subsurface volume of interest. A well or a wellbore may be drilled in one or more directions. For example, a well or a wellbore may include a vertical well, a horizontal well, a deviated well, and/or other type of well. A well or a wellbore may be drilled in the subterranean formation for exploration and/or recovery of resources. A plurality of wells (e.g., tens to hundreds of wells) or a plurality of wellbores are often used in a field depending on the desired outcome.

A well or a wellbore may be drilled into a subsurface volume of interest using practically any drilling technique and equipment known in the art, such as geosteering, directional drilling, etc. Drilling the well may include using a tool, such as a drilling tool that includes a drill bit and a drill string. Drilling fluid, such as drilling mud, may be used while drilling in order to cool the drill tool and remove cuttings. Other tools may also be used while drilling or after drilling, such as measurement-while-drilling (MWD) tools, seismic-while-drilling tools, wireline tools, logging-while-drilling (LWD) tools, or other downhole tools. After drilling to a predetermined depth, the drill string and the drill bit may be removed, and then the casing, the tubing, and/or other equipment may be installed according to the design of the well. The equipment to be used in drilling the well may be dependent on the design of the well, the subterranean formation, the hydrocarbons, and/or other factors.

A well may include a plurality of components, such as, but not limited to, a casing, a liner, a tubing string, a sensor, a packer, a screen, a gravel pack, artificial lift equipment (e.g., an electric submersible pump (ESP)), and/or other components. If a well is drilled offshore, the well may include one or more of the previous components plus other offshore components, such as a riser. A well may also include equipment to control fluid flow into the well, control fluid flow out of the well, or any combination thereof. For example, a well may include a wellhead, a choke, a valve, and/or other control devices. These control devices may be located on the surface, in the subsurface (e.g., downhole in the well), or any combination thereof. In some embodiments, the same control devices may be used to control fluid flow into and out of the well. In some embodiments, different control devices may be used to control fluid flow into and out of a well. In some embodiments, the rate of flow of fluids through the well may depend on the fluid handling capacities of the surface facility that is in fluidic communication with the well. The equipment to be used in controlling fluid flow into and out of a well may be dependent on the well, the subsurface region, the surface facility, and/or other factors. Moreover, sand control equipment and/or sand monitoring equipment may also be installed (e.g., downhole and/or on the surface). A well may also include any completion hardware that is not discussed separately. The term "well" may be used synonymously with the terms "borehole," "wellbore," or "well bore." The term "well" is not limited to any description or configuration described herein.

"Hydraulic fracturing" is one way that hydrocarbons may be recovered (sometimes referred to as produced) from the formation. For example, hydraulic fracturing may entail preparing a fracturing fluid and injecting that fracturing fluid into the wellbore at a sufficient rate and pressure to open existing fractures and/or create fractures in the formation. The fractures permit hydrocarbons to flow more freely into the wellbore. In the hydraulic fracturing process, the fracturing fluid may be prepared on-site to include at least proppants. The proppants, such as sand or other particles, are meant to hold the fractures open so that hydrocarbons may more easily flow to the wellbore. The fracturing fluid and the proppants may be blended together using at least one blender. The fracturing fluid may also include other components in addition to the proppants.

The wellbore and the formation proximate to the wellbore are in fluid communication (e.g., via perforations), and the fracturing fluid with the proppants is injected into the wellbore through a wellhead of the wellbore using at least one pump (oftentimes called a fracturing pump). The fracturing fluid with the proppants is injected at a sufficient rate and pressure to open existing fractures and/or create fractures in the subsurface volume of interest. As fractures become sufficiently wide to allow proppants to flow into those fractures, proppants in the fracturing fluid are deposited in those fractures during injection of the fracturing fluid. After the hydraulic fracturing process is completed, the fracturing fluid is removed by flowing or pumping it back out of the wellbore so that the fracturing fluid does not block the flow of hydrocarbons to the wellbore. The hydrocarbons will typically enter the same wellbore from the formation and go up to the surface for further processing.

The equipment to be used in preparing and injecting the fracturing fluid may be dependent on the components of the fracturing fluid, the proppants, the wellbore, the formation, etc. However, for simplicity, the term "fracturing apparatus" is meant to represent any tank(s), mixer(s), blender(s), pump(s), manifold(s), line(s), valve(s), fluid(s), fracturing fluid component(s), proppants, and other equipment and non-equipment items related to preparing the fracturing fluid and injecting the fracturing fluid.

It is understood that when combinations, subsets, groups, etc. of elements are disclosed (e.g., combinations of components in a composition, or combinations of steps in a method), that while specific reference of each of the various individual and collective combinations and permutations of these elements may not be explicitly disclosed, each is specifically contemplated and described herein. By way of example, if an item is described herein as including a component of type A, a component of type B, a component of type C, or any combination thereof, it is understood that this phrase describes all of the various individual and collective combinations and permutations of these components. For example, in some embodiments, the item described by this phrase could include only a component of type A. In some embodiments, the item described by this phrase could include only a component of type B. In some embodiments, the item described by this phrase could include only a component of type C. In some embodiments, the item described by this phrase could include a component of type A and a component of type B. In some embodiments, the item described by this phrase could include a component of type A and a component of type C. In some embodiments, the item described by this phrase could include a component of type B and a component of type C. In some embodiments, the item described by this phrase could include a component of type A, a component of type B, and a component of type C. In some embodiments, the item described by this phrase could include two or more components of type A (e.g., A1 and A2). In some embodiments, the item described by this phrase could include two or more components of type B (e.g., B1 and B2). In some embodiments, the item described by this phrase could include two or more components of type C (e.g., C1 and C2). In some embodiments, the item described by this phrase could include two or more of a first component (e.g., two or more components of type A (A1 and A2)), optionally one or more of a second component (e.g., optionally one or more components of type B), and optionally one or more of a third component (e.g., optionally one or more components of type C). In some embodiments, the item described by this phrase could include two or more of a first component (e.g., two or more components of type B (B1 and B2)), optionally one or more of a second component (e.g., optionally one or more components of type A), and optionally one or more of a third component (e.g., optionally one or more components of type C). In some embodiments, the item described by this phrase could include two or more of a first component (e.g., two or more components of type C (C1 and C2)), optionally one or more of a second component (e.g., optionally one or more components of type A), and optionally one or more of a third component (e.g., optionally one or more components of type B).

If a component of a figure is described but not expressly shown or labeled in that figure, the label used for a corresponding component in another figure may be inferred to that component. Conversely, if a component in a figure is labeled but is not described, the description for such component may be substantially the same as the description for the corresponding component in another figure. The numbering scheme for the various components in the figures herein is such that each component is a three-digit number or a four-digit number, and corresponding components in other figures have the identical last two digits. For any figure shown and described herein, one or more of the components may be omitted, added, repeated, and/or substituted. Accordingly, embodiments shown in a particular figure should not be considered limited to the specific arrangements of components shown in such figure.

Further, a statement that a particular embodiment (e.g., as shown in a figure herein) does not have a particular feature or component does not mean, unless expressly stated, that such embodiment is not capable of having such feature or component. For example, for purposes of present or future claims herein, a feature or component that is described as not being included in an example embodiment shown in one or more particular drawings is capable of being included in one or more claims that correspond to such one or more particular drawings herein.

Example embodiments of well evaluation using water chemistry analysis will be described more fully hereinafter with reference to the accompanying drawings, in which example embodiments of well evaluation using water chemistry analysis are shown. Well evaluation using water chemistry analysis may, however, be embodied in many different forms and should not be construed as limited to the example embodiments set forth herein. Rather, these example embodiments are provided so that this disclosure will be thorough and complete, and will fully convey the scope of well evaluation using water chemistry analysis to those of ordinary skill in the art. Like, but not necessarily the same, elements (also sometimes called components) in the various figures are denoted by like reference numerals for consistency.

Terms such as "first", "second", "primary," "secondary," "above", "below", "inner", "outer", "distal", "proximal", "end", "top", "bottom", "upper", "lower", "side", "left", "right", "front", "rear", and "within", when present, are used merely to distinguish one component (or part of a component or state of a component) from another. This list of terms is not exclusive. Such terms are not meant to denote a preference or a particular orientation, and they are not meant to limit embodiments of well evaluation using water chemistry analysis. In the following detailed description of the example embodiments, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Figure 2:
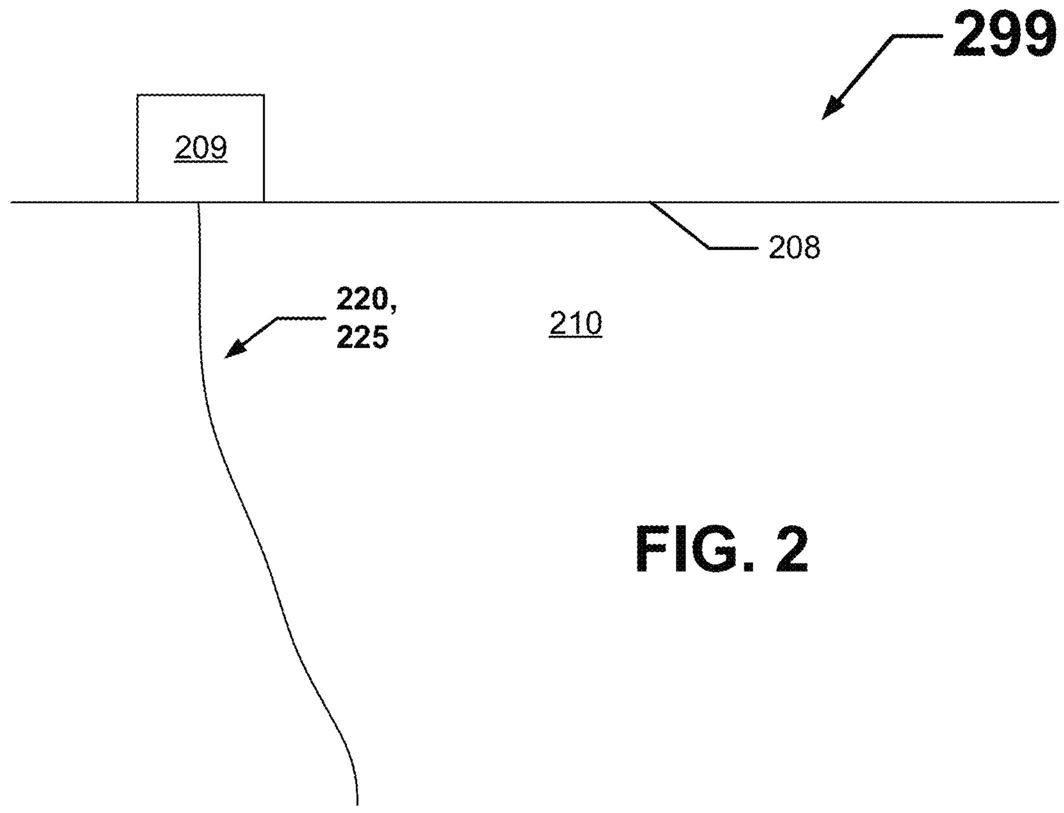
FIG. 2 shows another field system in which example embodiments may be used.
Figure 3A:
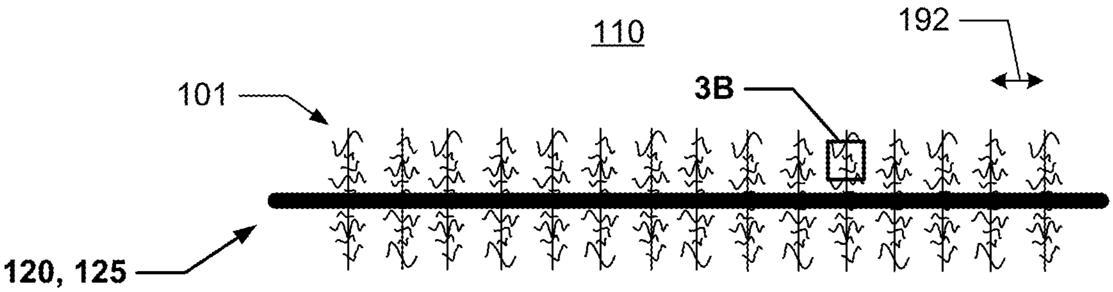
FIGS. 3A and 3B show detailed views of the field system of FIG. 1 in which example embodiments may be used.
Figure 3B:
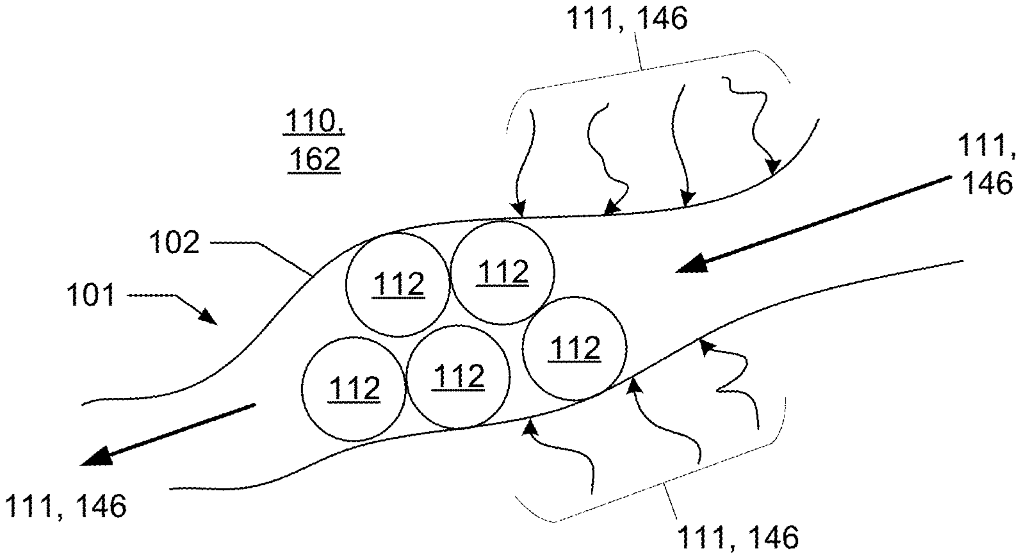

FIG. 1 shows a schematic diagram of a land-based field system 199 with which example embodiments may be used. FIG. 2 shows a schematic diagram of another land-based field system 299 with which example embodiments may be used. FIG. 3A shows a detail of a substantially horizontal section 103 of the wellbore 120 of FIG. 1. FIG. 3B shows a detail of a fracture 101 of FIG. 3A. The field system 199 of FIG. 1 includes a producing wellbore 120 disposed in a subterranean formation 110 using field equipment 109 (e.g., a derrick, a tool pusher, a clamp, a tong, drill pipe, casing pipe, a drill bit, a wireline tool, a fluid pumping system)

located above a surface 108 and within the wellbore 120. Example embodiments may also be used in other types of wells (e.g., injection wells, geothermal wells) that have vertical sections 104 and/or horizontal sections 103.

With respect to the system 199 of FIG. 1, once the wellbore 120 is drilled, a casing string 125 is inserted into the wellbore 120 to stabilize the wellbore 120 and allow for the extraction of subterranean resources (e.g., natural gas, oil, produced water) from the subterranean formation 110. Field equipment 109, located at the surface 108, is used to drill, encase, fracture, produce, and/or perform any other part of a field operation with respect to the wellbore 120. The wellbore 120 of FIG. 1 starts out with a substantially vertical section 104, and then has a substantially horizontal section 103. This configuration of the wellbore 120 is common for exploration and production of subterranean resources, such as oil and natural gas.

Similarly, with respect to the system 299 of FIG. 2, once the wellbore 220 is drilled, a casing string 225 is inserted into the wellbore 220 to stabilize the wellbore 220 from the subterranean formation 210. Field equipment 209, located at the surface 208, is used to drill, encase, fracture, produce, and/or perform any other part of a field operation with respect to the wellbore 220. The wellbore 220 of FIG. 2 is substantially vertical. This configuration of the wellbore 220 is common for injection wells.

Referring back to FIG. 1, the surface 108 may be ground level for an onshore application and the sea floor (or other similar floor under a body of water) for an offshore application. A body of water may include, but it not limited to, sea water, brackish water, flowback or produced water, wastewater (e.g., reclaimed or recycled), brine (e.g., reservoir or synthetic brine), fresh water (e.g., fresh water comprises <1,000 ppm TDS), any other type of water, or any combination thereof. For offshore applications, at least some of the field equipment may be located on a platform that sits above the water level. The point where the wellbore 120 begins at the surface 108 may be called the wellhead.

While not shown in FIGS. 1 and 2, there may be multiple wellbores 120, 220, each with its own wellhead but that is located close to the other wellheads, drilled into the subterranean formation 110, 210 and having substantially vertical sections and/or horizontal sections 103 that are close to each other. In such a case, the multiple wellbores 120, 220 may be drilled at the same pad or at different pads.

During the process of drilling the wellbore 120 of FIG. 1, as detailed in FIGS. 3A and 3B, cuttings, water 146 (e.g., produced water, formation water), and other subterranean resources 111 (e.g., relatively small amounts of oil or natural gas) may be extracted (or otherwise obtained) from downhole to the surface 108, where some of the field equipment 109 separates out at least some of the cuttings and recirculates the produced water back downhole. When the drilling process is complete, other operations, such as fracturing operations, may be performed. While the subterranean formation 110 may have naturally-occurring fractures 101 and some fractures 101 that may be created when drilling the wellbore 120, these fractures 101 may need to be enlarged and elongated, and additional fractures 101 may need to be created, in order to extract additional subterranean resources 111 (e.g., oil, natural gas) from the subsurface. The fractures 101 are shown to be located in the horizontal section 103 of the wellbore 120 in FIG. 1. The fractures 101, whether created and/or naturally occurring, may additionally or alternatively be located in other sections (e.g., a substantially vertical section 104, a transition area between a vertical section 104 and a horizontal section 103) of the wellbore 120. In some cases, a wellbore 220 has no substantially horizontal sections, as shown in FIG. 2. Example embodiments may be used along any portion of a wellbore (e.g., wellbore 120, wellbore 220) where fractures 101 are located.

The subterranean formation 110 may include one or more of a number of formation types, including but not limited to shale, limestone, sandstone, clay, sand, and salt. In certain embodiments, a subterranean formation 110 may include one or more reservoirs in which one or more resources (e.g., oil, natural gas, water, steam) may be located. One or more of a number of field operations (e.g., fracturing (e.g., hydraulic fracturing), coring, tripping, drilling, setting casing, extracting downhole resources, production) may be performed to reach an objective of a user with respect to the subterranean formation 110.

The wellbore 120 may have one or more of a number of segments or hole sections, where each segment or hole section may have one or more of a number of dimensions. Examples of such dimensions may include, but are not limited to, a size (e.g., diameter) of the wellbore 120, a curvature of the wellbore 120, a total vertical depth of the wellbore 120, a measured depth of the wellbore 120, and a horizontal displacement of the wellbore 120. There may be multiple overlapping casing strings of various sizes (e.g., length, outer diameter) contained within and between these segments or hole sections to ensure the integrity of the wellbore construction. In this case, one or more of the segments of the subterranean wellbore 120 is the substantially horizontal section 103.

As discussed above, inserted into and disposed within the wellbore 120 of FIGS. 1 and 2 are a number of casing pipes that are coupled to each other end-to-end to form the casing string 125 and the casing string 225, respectively. In these cases, each end of a casing pipe has mating threads (a type of coupling feature) disposed thereon, allowing a casing pipe to be directly or indirectly mechanically coupled to another casing pipe in an end-to-end configuration. The casing pipes of the casing string 125 and the casing string 225 may be indirectly mechanically coupled to each other using a coupling device, such as a coupling sleeve.

Each casing pipe of the casing string 125 and the casing string 225 may have a length and a width (e.g., outer diameter). The length of a casing pipe may vary. For example, a common length of a casing pipe is approximately 40 feet. The length of a casing pipe may be longer (e.g., 60 feet) or shorter (e.g., 10 feet) than 40 feet. The width of a casing pipe may also vary and may depend on the cross-sectional shape of the casing pipe. For example, when the shape of the casing pipe is cylindrical, the width may refer to an outer diameter, an inner diameter, or some other form of measurement of the casing pipe. Examples of a width in terms of an outer diameter may include, but are not limited to, 4½ inches, 7 inches, 7⅝ inches, 8⅝ inches, 10¾ inches, 13⅜ inches, and 14 inches.

The size (e.g., width, length) of the casing string 125 and the casing string 225 may be based on the information (e.g., diameter of the borehole drilled) gathered using field equipment with respect to the subterranean wellbore 120 and the subterranean wellbore 220, respectively. The walls of the casing string 125 and the casing string 225 have an inner surface that forms a cavity that traverses the length of the casing string 125 and the casing string 225. Each casing pipe may be made of one or more of a number of suitable materials, including but not limited to steel. Cement is poured into the wellbore 120 through the cavity and then forced upward between the outer surface of the casing string 125 and the wall of the subterranean wellbore 120. Similarly, cement is poured into the wellbore 220 through the cavity and then forced upward between the outer surface of the casing string 225 and the wall of the subterranean wellbore 220. In some cases, a liner may additionally be used with, or alternatively be used in place of, some or all of the casing pipes.

Referring to the system 199 of FIGS. 1, 3A, and 3B, once the cement dries to form concrete, a number of fractures 101 are created in the subterranean formation 110. The fractures 101 may be created in any of a number of ways known in the industry, including but not limited to hydraulic fracturing, fracturing using electrodes, and/or other methods of inducing fractures. The hydraulic fracturing process involves the injection of large quantities of fluids containing water, chemical additives, and proppant 112 into the subterranean formation 110 from the wellbore 120 to create fracture networks. A subterranean formation 110 naturally has fractures 101, but these naturally occurring fractures 101 have inconsistent characteristics (e.g., length, spacing) and so in some cases cannot be relied upon for extracting subterranean resources without having additional fractures 101, such as what is shown in FIG. 3A, created in the subterranean formation 110.

Operations that create fractures 101 in the subterranean formation 110 use any of a number of fluids that include proppant 112 (e.g., sand, ceramic pellets). When proppant 112 is used, some of the fractures 101 (also sometimes called principal or primary fractures) receive proppant 112, while a remainder of the fractures 101 (also sometimes called secondary fractures) do not have any proppant 112 in them.

As shown in FIG. 3B, the proppant 112 is designed to become lodged inside at least some of the created fractures 101 to keep those fractures 101 open after the fracturing operation is complete. The size of the proppant 112 is an important design consideration. Sizes (e.g., 40/70 mesh, 50/140 mesh) of the proppant 112 may vary. While the shape of the proppant 112 is shown as being uniformly spherical, and the size is substantially identical among the proppant 112, the actual sizes and shapes of the proppant 112 may vary. If the proppant 112 is too small, the proppant 112 will not be effective at keeping the fractures 101 open enough to effectively allow water 146 and/or other subterranean resources 111 to flow through the fractures 101 from the rock matrices 162 in the subterranean formation 110 to the wellbore 120. If the proppant 112 is too large, the proppant 112 may plug up the fractures 101, blocking the flow of the water 146 and/or other subterranean resources 111 through the fractures 101.

The use of proppant 112 in certain types of subterranean formation 110, such as shale, may be important. Shale formations typically have permeabilities on the order of microdarcys (μD) to nanodarcys (nD). When fractures 101 are created in such formations with low permeabilities, it is important to sustain the fractures 101 and their permeability and conductivity for an extended period of time in order to extract more of the subterranean resource 111. Example embodiments may also be applied to fluids used in other types of field operations, including but not limited to fracturing operations, wells used to utilize subterranean geothermal resources, and injection wells.

Regardless of the type (e.g., conventional, unconventional) of subterranean formation 110, when proppant 112 and/or other similar components of a fracturing fluid are used in a fracturing operation, The proppant 112 and/or other similar components may be designed to become lodged within fractures 101 that result in principal fractures, which are designed to last (stay open) for a longer period of time as fluids (e.g., water 146, subterranean resources 111) flow therethrough. Fractures 101 that do not have proppant 112 and/or other similar components lodged therein may be referred to as secondary fractures, which may not last as long (close or reduce in size more quickly) as principal fractures.

The various created fractures 101 that originate at the wellbore 120 and extend outward into the rock matrices 162 in the subterranean formation 110 in this case have consistent penetration lengths perpendicular to the wellbore 120 and have consistent coverage along at least a portion of the lateral length (substantially horizontal section) of the wellbore 120. For example, created fractures 101 may be 50 meters high and 200 meters long. Further, the created fractures 101 may be spaced a distance 192 apart from each other. The distance 192 (e.g., 25 meters, 5 meters, 12 meters) may be optimized based on the permeability and the porosity of the rock matrix 162 of the subterranean formation 110.

The created fractures 101 create a volume 190 within the subterranean formation 110 where the rock matrix 162 of the subterranean formation 110 is connected to the high conductivity fractures 101 located a short distance away. In addition to different configurations of the fractures 101, other factors that may contribute to the viability of the subterranean formation 110 may include, but are not limited to, permeability of the rock matrix 162, capillary pressure, and the temperature and pressure of the subterranean formation 110. Each fracture 101, whether created or naturally occurring, is defined by a wall 102, also called a frac face 102 herein. The frac face 102 provides a transition between the paths formed by the rock matrices 162 in the subterranean formation 110 and the fracture 101. The subterranean resources 111 flow through the paths formed by the rock matrices 162 in the subterranean formation 110 into the fracture 101.

The rock matrices 162, as well as the rest of the subterranean formation 110, both without and outside the volume 190, have a certain amount of water 146 therein. The water 146 may be or include, for example, formation water from the formation matrix within the volume 190, moveable free formation water, and "external" water from non-targeted formation/sources (e.g., outside the target volume 190). These external sources of water 146 may include water from a nearby SWD source(s), a nearby hydrocarbon producing source, and/or other sources.

The water 146 may have any of a number of different components (e.g., minerals, chemical additives, acids, completion brine) in addition to formation water. The contents of water 146 in one part (e.g., outside the volume 190) of the subterranean formation 110 may be the same as, or different than, the contents of the water 146 in other parts (e.g., in the rock matrices 162) of the subterranean formation 110. In some cases, such as during a stage (e.g., a hydraulic fracturing stage) of a field operation, the fluids (e.g., fracturing fluid) used in that stage may mix with or include the water 146, thereby changing the contents or composition of the in situ water chemistry in parts (e.g., at or near the fractures 101) of the subterranean formation 110. The water 146 may include one or more of a number of types of water, including but not limited to sea water, brackish water, flowback or produced water, wastewater (e.g., reclaimed or recycled), brine (e.g., reservoir or synthetic brine), fresh water (e.g., fresh water comprises <1,000 ppm TDS), any other type of water, or any combination thereof.

Figure 4:
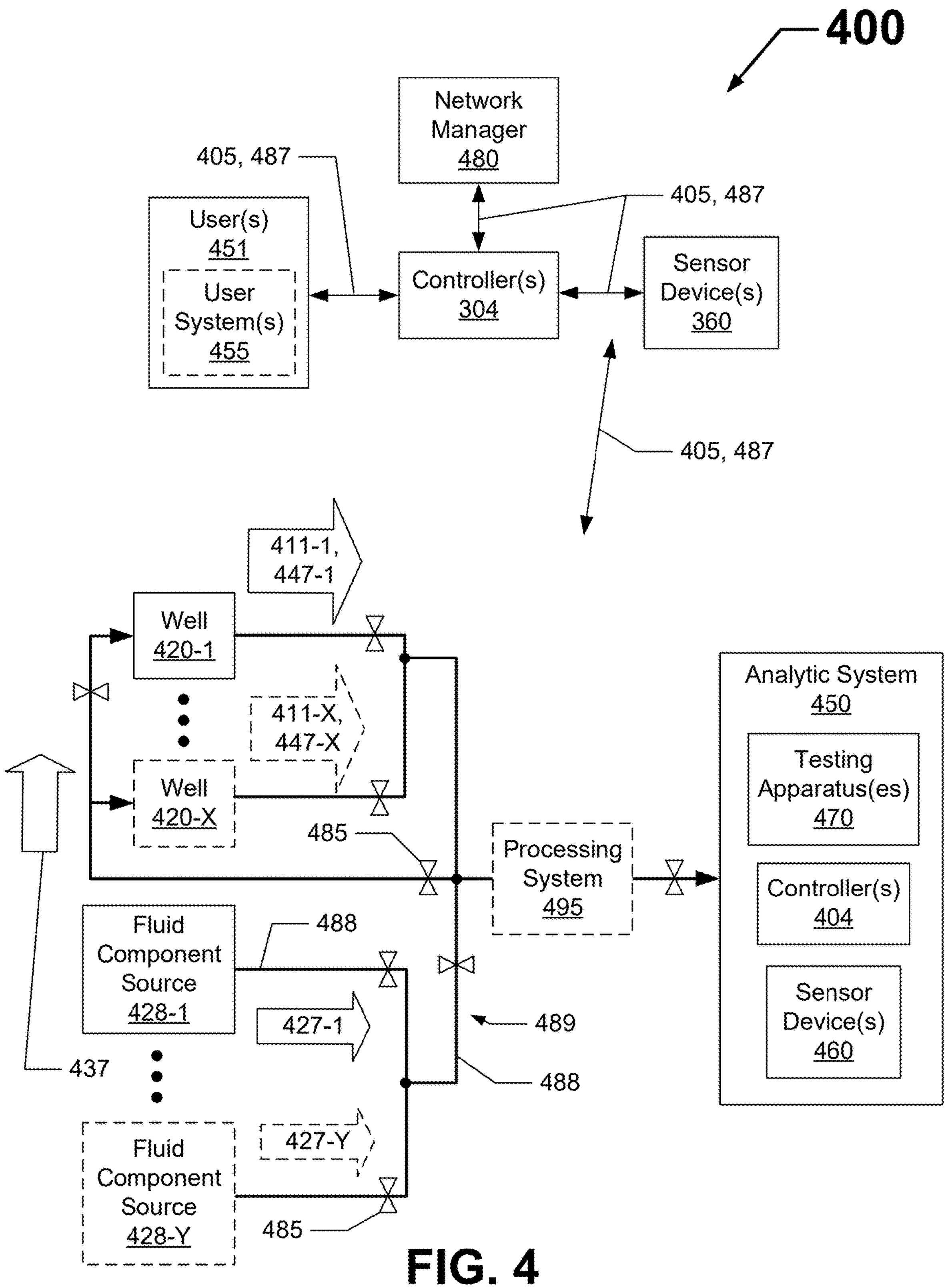
FIG. 4 shows a diagram of a system for well evaluation using water chemistry analysis according to certain example embodiments.

FIG. 4 shows a diagram of a system 400 for well evaluation using water chemistry analysis according to certain example embodiments. The system 400 of FIG. 4 includes one or more fluid component sources 428, one or more wells 420, an example analytic system 450, an optional processing system 495, one or more controllers 304, one or more sensor devices 360, one or more users 451 (including one or more optional user systems 455), a network manager 480, a material conveyance system 488, and one or more valves 485. The analytic system 450 in this case includes one or more testing apparatuses 470, one or more controllers 404, and one or more sensor devices 460.

The components shown in FIG. 4 are not exhaustive, and in some embodiments, one or more of the components shown in FIG. 4 may not be included in the example system 400. Any component of the system 400 may be discrete or combined with one or more other components of the system 400. Also, one or more components of the system 400 may have different configurations. For example, one or more sensor devices 360 may be disposed within or disposed on other components (e.g., the material conveyance system 488, a valve 485, a fluid component source 428, a well 420). As another example, a controller 304, rather than being a stand-alone device, may be part of one or more other components (e.g., a fluid component source 428, a well 420) of the system 400.

Referring to FIGS. 1 through 4, the system 400 may include one or more wells 420 (in this case, well 420-1 through well 420-X). Each of the wells 420 of the system 400 may be substantially similar to the wells discussed above. Some or all of the wells 420 may be from a common pad. Each well 420 may produce water (e.g., water 146), subterranean resources 411, cuttings, other materials, or any combination thereof. From these materials that flow uphole from each well 420 to the surface, one or more samples 447 may be obtained. Each sample 447 that is obtained may be transported through the material conveyance system 488, through the optional processing system 495, and to the analytic system 450. Over time, a well 420 may be used for different purposes. For example, well 420-1 may be used as a production well at one time, as a geothermal resource at another time, and as an injection well at yet another time.

A sample 447 of FIG. 4 may include water, which may be substantially the same as the water 146 discussed above. Specifically, the water may be any type of water, including but not limited to the produced water, sea water, brackish water, wastewater (e.g., reclaimed or recycled), brine (e.g., reservoir or synthetic brine), fresh water (e.g., fresh water comprises <1,000 ppm TDS), or any other type of water. Each sample 447 is specifically categorized as being from a particular well 420. A sample 447 may include formation water, fracturing fluid (frac water), and/or hydrocarbon (e.g., oil, natural gas). For example, samples 447-1 are from well 420-1, and samples 447-X are from well 420-X.

The samples 447 are moved from each well 420 toward the analytic system 450 using a conveyance system 448. The conveyance system 448 may be configured to extract the samples 447 from a well 420 and convey the samples 447 through the conveyance system 488 toward the analytic system 450. The conveyance system 448 may additionally or alternatively be configured to extract a fluid component 427 from a fluid component source 428 and convey the fluid component 427 through the conveyance system 488 to the analytic system 450, As discussed above, the system 400 may also include one or more fluid component sources 428. Each fluid component source 428 may hold one or more fluid components 427. A fluid component source 428 may include, but is not limited to, a natural vessel (e.g., land that forms walls to contain a liquid, a subterranean cavity that holds carbon dioxide or other gas or liquid) and a man-made storage tank or other type of vessel. Each fluid component 427 may be or include a liquid, a solid, and/or a gas. A fluid component 427 may be in the form of a liquid, a gas, and/or a solid. A single fluid component 427 or a mixture of multiple fluid component g427 may be disposed in a fluid component source 428.

Examples of a fluid component 427 may include, but are not limited to, carbon dioxide, gas with various concentrations of $CO_2$ (e.g., in liquid form, in gas form, in produced gas from a field operation, from a source external to a field operation), hydrocarbons, a chemical used for a fracturing operation, water that does not come from a well 420, methane, $H_2S$, nucleation catalyzing metals, an alkali salt (e.g., NaOH), sodium bicarbonate ($NaHCO_3$), sodium carbonate ($Na_2CO_3$), polymers and/or other substances, and flocculation agents. In some cases, multiple fluid components 427 may be combined to form a fluid 437. In some other cases, a single fluid component 427 may also be a fluid 437.

A fluid component 427 may serve one or more purposes in one or more field operations. For example, a fluid component 427 may be used in a fluid 437 to generate and/or enhance fractures 101 in a subterranean formation 110 adjacent to a well 420 during a fracturing operation. As another example, a fluid component 427 may be carbon dioxide, a gas stream containing carbon dioxide (e.g., stored, produced), or any combination thereof, which may be used during injection of an injection well. One of ordinary skill in the art will appreciate that other fluid components 427 and/or combinations thereof are possible in example embodiments. As yet another example, a fluid component 427 may be used in a fluid 437 that is injected into a well 420 to utilize a geothermal resource (e.g., heat and extract the heated fluid 437, extract steam that results from interaction of the fluid 437 with the geothermal resource) within the well 420.

The conveyance system 448 may include one or more of a number of pieces of equipment to perform its function. Examples of such equipment may include, but are not limited to, a compressor, a motor, a pump, a conveyer, a truck or other vehicle, a rail system, a crane, a shaker, a vibrator, piping, a valve (e.g., valve 485), a controller (e.g., controller 404), and a sensor device (e.g., sensor device 460). Some or all of the conveyance system 448 may operate using a controller (e.g., controller 404). In addition, or in the alternative, one or more users 451 may perform one or more of the various functions required to move some or all of the samples 447, one or more of the fluid components 427, and/or one or more of the fluids 437 using the conveyance system 448. The conveyance system 488 (including the collection area 489) may include any components, devices, subsystems, etc. that transport the samples 447, the fluid components 427, and the fluid 437 within the system 400 from one component to another component. The conveyance system 488 may be configured to transport solids, liquids, and/or gases.

For example, in order to transport liquids and gases within the system 400, the conveyance system 488 may include piping. In such a case, the piping may include multiple pipes, ducts, elbows, joints, sleeves, collars, and similar components that are coupled to each other (e.g., using coupling features such as mating threads) to establish a network for transporting such liquids and/or gases within the system 400. Each component of the piping may have an appropriate size (e.g., inner diameter, outer diameter) and be made of an appropriate material (e.g., steel, PVC) to safely and efficiently handle the pressure, temperature, flow rate, and other characteristics of the liquids and/or gases that flow therethrough. As another example, in order to transport solids within the system 400, the conveyance system 488 may include conveyer belts, trucks, bulldozers, backhoes, and/or other similar equipment.

There may be a number of valves 485 placed in-line with the conveyance system 488 (or portions thereof) at various locations in the system 400 to control the flow of the samples 447, the fluid components 427, and/or the fluid 437 in liquid and/or gas form. A valve 485 may have one or more of any of a number of configurations, including but not limited to a guillotine valve, a ball valve, a gate valve, a butterfly valve, a pinch valve, a needle valve, a plug valve, a diaphragm valve, and a globe valve. One valve 485 may be configured the same as or differently compared to another valve 485 in the system 400. Also, one valve 485 may be controlled (e.g., manually by a user 451, automatically by a controller 404 of the analytic system 450) the same as or differently compared to another valve 485 in the system 400.

In some cases, positioned within the material conveyance system 488 between the wells 420, the fluid component sources 428, and the analytic system 450 may be an optional processing system 495. Such a processing system 495 may be or include part of the field equipment 109 discussed above. The processing system 495 may be designed to separate cuttings, other subterranean resources 411 (e.g., oil, natural gas), and/or other elements from the samples 447 as the samples 447 are prepared for testing in the analytic system 450 and/or for recirculation into a well 420 (e.g., the same well 420 from which the samples 447 are obtained, another well 420 (e.g., a SWD well)).

Such a processing system 495 may include one or more of a number of various pieces of equipment. Such equipment may include, but is not limited to, a pump, a motor, a filter, a centrifuge, a heater, a blower, a condenser, a vessel, a funnel, a strainer, a separator, an agitator, a paddle, a circulating system, an aerator, a heat exchanger, a column, a test tube, a separator, a mixer (e.g., a centrifuge mixer, a desander, a tumbler mixer, a homogenizer, a static mixer, a drum mixer, a fluidization mixer, agitator mixers, paddle mixers, an emulsifier, a drum mixer, a pail mixer, a convective mixer, an agitator, a batch mixer, and a ribbon mixer), a controller (e.g., controller 304, controller 404), and a sensor device (e.g., sensor device 360, sensor device 460).

The processing system 495 may operate substantially continuously (as when the samples 447 and/or the fluid components 427 substantially continuously flow into the processing system 495) or at intervals (as when the samples 447 and/or the fluid components 427 are introduced into the processing system 495 intermittently). The processing system 495 may be or include a single apparatus (with or without multiple portions) or multiple apparatus (or portions thereof) that operate in series and/or in parallel with each other. As an example, the processing system 495 may include a temperature conditioning portion, a mixing portion, a drying portion, and a separating portion that operate in series with each other. As another example, the processing system 495 may include multiple mixers that operate in parallel with each other, where each mixer may mix one or more fluid components 427 and/or one or more of the samples 447 into a different fluid 437 simultaneously. Some or all of the processing system 495 may be controlled by one or more controllers 404 of the analytic system 450.

The processing system 495 may control various aspects (e.g., temperature, pressure, flow rate) of the samples 447, the fluid components 427, and/or the fluid 437. In some cases, the processing system 495 is designed to subject the samples 447, the fluid components 427, and/or the fluid 437 to conditions (e.g., pressure, temperature, flow rate) that simulate the conditions at the subsurface (e.g., corresponding downhole conditions of the fractures 101 and rock matrix in the subterranean formation 110 adjacent to the wellbore 120).

In some cases, some or all of the processing system 495 may be operated, paused, and/or stopped so that the samples 447, the fluid components 427, and/or the fluid 437 may be evaluated by the testing apparatus 470. Testing by the testing apparatus 470 may be controlled by a user 451 (e.g., a human being) and/or a controller 404 of the analytic system 450. Testing by the testing apparatus 470 may be based on historical data and/or field data (e.g., measurements from sensor devices 460). Testing by the testing apparatus 470 may generate test scenarios or expected results. Testing by the testing apparatus 470 may operate using one or more algorithms 533, one or more protocols 532, and/or stored data 534 (all discussed below).

Whether inside the processing system 495 or in a collection area 489 (e.g., a header, a manifold), some or all of the samples 447 and/or some or all of the fluid components 427 may be introduced to each other. Conditions (e.g., temperature, pressure) in some or all of the processing system 495 may vary and may be customized or otherwise controlled (e.g., to represent field operating conditions)

To control the composition of a fluid 437 at a given point in time, the amount of one or more of the samples 447 and/or the amount of the one or more fluid components 427 that are released or withdrawn from the one or more wells 420 and/or the one or more fluid component sources 428, respectively, may be regulated in real time. This regulation may be performed automatically by a controller (e.g., controller 404) and/or manually by a user 451 (which may include an associated user system 455). This regulation may be performed using equipment such as the processing system 495 (including portions thereof), pumps, compressors, field equipment (e.g., field equipment 109), the conveyance system 488, valves 485, regulators, sensor devices 460, etc. The samples 447 of a well 420 and a fluid component 427 of a fluid component source 428 may have any of a number of different compositions that are naturally occurring or man-made.

The analytic system 450 of the system 400 may be configured to perform water chemistry analysis on one or more of the samples 447 from one or more of the wells 420. In addition, the analytic system 450 of the system 400 may be configured to perform a chemical and/or other type of analysis of one or more of the subterranean resources 411 from one or more of the wells 420, one or more of the fluid components 427 from one or more of the fluid component sources 428, and/or one or more of the fluids 437 that are delivered to one or more of the wells 420. As a result, the system 400 (and more specifically the analytic system 450) may be used to evaluate multiple wells using water chemistry analysis of the water in the samples 447, analysis of subterranean resources 411, analysis of fluid components 427, and/or analysis of the fluids 437. As a result, example embodiments may be used, for example, to optimize the results of a particular field operation (e.g., a fracturing procedure).

As discussed above, the analytic system 450 may include one or more components. For example, in this case, the analytic system 450 includes one or more testing apparatuses 470, one or more controllers 404, and one or more sensor devices 460. Each testing apparatus 470 may be configured to test one or more of the samples 447, one or more of the subterranean resources 411, one or more of the fluid components 427, and/or one or more of the fluids 437. A single testing apparatus 470 may perform multiple tests (e.g., on a single fluid component 427, on samples 447 from a single well 420, on a fluid 437 and on a subterranean resource 411) simultaneously.

When the analytic system 450 has multiple testing apparatuses 470, one testing apparatus 470 may operate in conjunction with, or independently of, one or more of the other testing apparatuses 470. Further, when the analytic system 450 has multiple testing apparatuses 470, one testing apparatus 470 may be configured (e.g., in terms of equipment, in terms of operating capability) the same as, or differently than, one or more of the other testing apparatuses 470. The operation of a testing apparatus 470 may be controlled by a user 451 (including an associated user system 455) and/or a controller 404 of the analytic system 450.

A testing apparatus 470 may include or interact with one or more sensor devices 460 (discussed below) to perform one or more of its functions. Testing performed by a testing apparatus 470 may use or include historical data and/or field data (e.g., measurements from sensor devices 460). Testing may generate test scenarios or expected results. Testing may include the use of process chemistry simulators, fluid electrolyte modeling, chemistry calculations using field/historical data to model the process, etc.

A controller 404 of the analytic system 450 may be configured to evaluate, using results of tests performed by a testing apparatus 470, the samples 447 obtained from one or more wells 420, one or more of the subterranean resources 411 obtained from one or more of the wells 420, one or more of the fluid components 427 obtained from one or more of the fluid component sources 428, and/or one or more of the fluids 437 that are delivered to one or more of the wells 420. In some cases, a controller 404 may be configured to facilitate the implementation of a test on a sample 447, control the parameters of a test performed on a sample 447, and/or take other actions associated with the testing of samples 447.

In some cases, one or more controllers 404 of the analytic system 450 may be used to control or facilitate control of the implementation of the output of any of the algorithms 533 (e.g., models) of the analytic system 450. For example, when the output of an algorithm 533 indicates a particular amount and type of chemical component or compound to add to a fluid 437 for use in one or more wells 420 during a current or planned field operation, one or more of the controllers 404 of the analytic system 450 may obtain the amount and type of chemical component or compound from one or more of the fluid component sources 428, mix the chemical component or compound into a fluid 437 using the processing system 495, and deliver the resulting fluid 437 to one or more of the wells 420 using the conveyance system 488.

As another example, based on the output of an algorithm 533, a controller 404 of the analytic system 450 may determine that a new well 420 would be beneficial to the overall production of subterranean resources 411 from the network of wells 420. In such a case, one or more of the controllers 404 of the analytic system 450 may generate a drilling plan for the new well 420, implement or facilitate implementation of the drilling plan, evaluate the drilling plan in real time as the new well is drilled, make any revisions to the drilling plan based on the real-time evaluation, and implement or facilitate implementation of the revisions to the drilling plan.

A testing apparatus 470 of the analytic system 450 may be configured to process one or more solids in addition to fluids. In such a case, the testing apparatus 470 may be configured to provide analysis of one or more precipitated solids 467, including but not limited to Fourier transformed infrared spectroscopy (FT-IR), x-ray fluorescence (XRF), x-ray diffraction (XRD), elemental analysis, etc. The testing apparatus 470 may include one or more of any of a number of different equipment, including but not limited to a sifter, a shaker, a screen, a motor, a controller (e.g., controller 404), and a sensor device (e.g., sensor device 460). In some cases, the testing apparatus 470, or portions thereof, may operate using a controller 404. In addition, or in the alternative, one or more users 451 may perform one or more of the various functions required to operate some or all of the testing apparatus 470.

Each testing apparatus 470 of the analytic system 450 may be configured to test the samples 447 of one or more wells 420, one or more fluid components 427, and one or more of the fluids 437. A testing apparatus 470 may be used in conjunction with one or more sensor devices 460 of the analytic system 450. A testing apparatus 470 may be or include a vessel (e.g., a bottle, a column, a test tube) inside of which various materials (e.g., samples 447 from a well 420, a fluid component 427, a fluid 437) are disposed for testing. In some cases, the materials placed in a testing apparatus 470 are first processed in the processing system 495. In any case, the materials are provided to a testing apparatus 470 by the conveyance system 488. A testing apparatus 470 may be used to test samples 447, a fluid component 427, a fluid 437, and/or any other component during a fracturing operation of one or more wells 420, during shut-in of a well 420, during pre-production of a well 420, during production of a well 420, and/or at any other time.

A testing apparatus 470 may include one or more components or pieces of equipment to perform its function. Examples of such components or pieces of equipment may include, but are not limited to, a membrane, a sifter, a shaker, a screen, an immersion separator, a reverse osmosis membrane, a nanofiltration membrane, a pH adjustment apparatus, a softening apparatus, a motor, a controller (e.g., controller 404), and a sensor device (e.g., sensor device 460). In some cases, a testing apparatus 470, or portions thereof, may operate using a controller 404. In addition, or in the alternative, one or more users 451 (e.g., a human being) may perform some or all of the various functions required to operate some or all of a testing apparatus 470.

The analytic system 450 may include one or more sensor devices 460. Each sensor device 460 includes one or more sensors that measure one or more parameters (e.g., pressure, flow rate, temperature, humidity, fluid content, voltage, current, permeability, porosity, rock characteristics, chemical elements in a fluid, chemical elements in a solid, concentrations, etc.). Examples of a sensor of a sensor device 460 may include, but are not limited to, a temperature sensor, a flow sensor, a pressure sensor, a gas spectrometer, a voltmeter, an ammeter, a permeability meter, a spectrograph, a gas chromatograph a porosimeter, and a camera. A sensor device 460 may be a stand-alone device or integrated with another component of the analytic system 450.

A parameter measured by a sensor device 460 may be associated with one or more components of the system 400. For example, a sensor device 460 may be configured to measure a parameter (e.g., flow rate, pressure, temperature, composition, concentration) of samples 447, a fluid component 427, and/or a fluid 437, a solid 467 at any location (e.g., between a well 420 and the analytic system 450, between a fluid component source 428 and the analytic system 450, within the processing system 495, etc.) of the system 400 at a particular time.

As another example, a sensor device 460 may be configured to determine how open or closed a valve 485 within the system 400 is. As yet another example, one or more sensor devices 460 may be used to identify the water chemistry of a sample 447. As still another example, one or more sensor devices 460 may be used to identify the contents of a fluid 437. As yet another example, one or more sensor devices 460 may be used to identify the contents of a fluid component 427.

In some cases, the measurements made by a number of sensor devices 460, each measuring a different parameter, may be used in isolation or in combination to determine and/or confirm whether a controller 404 should take a particular action (e.g., operate a valve 485, operate or adjust the operation of a testing apparatus 470, operate or adjust the operation of the processing system 495). When a sensor device 460 includes its own controller 404 (or portions thereof), then the sensor device 460 may be considered a type of computer device, as discussed below with respect to FIG. 6.

The analytic system 450 may include one or more controllers 404. A controller 404 of the analytic system 450 communicates with and in some cases controls one or more of the other components (e.g., a sensor device 460, a testing apparatus 470) of the analytic system 450 and/or one or more other components (e.g., a sensor device 360, a controller 304, the conveyance system 488, one or more valves 485, a fluid component source 428, the processing system 495) of a remainder of the system 400. A controller 404 performs any of a number of functions that include, but are not limited to, obtaining and sending data, evaluating data, following protocols, running algorithms, and sending commands.

Figure 5:
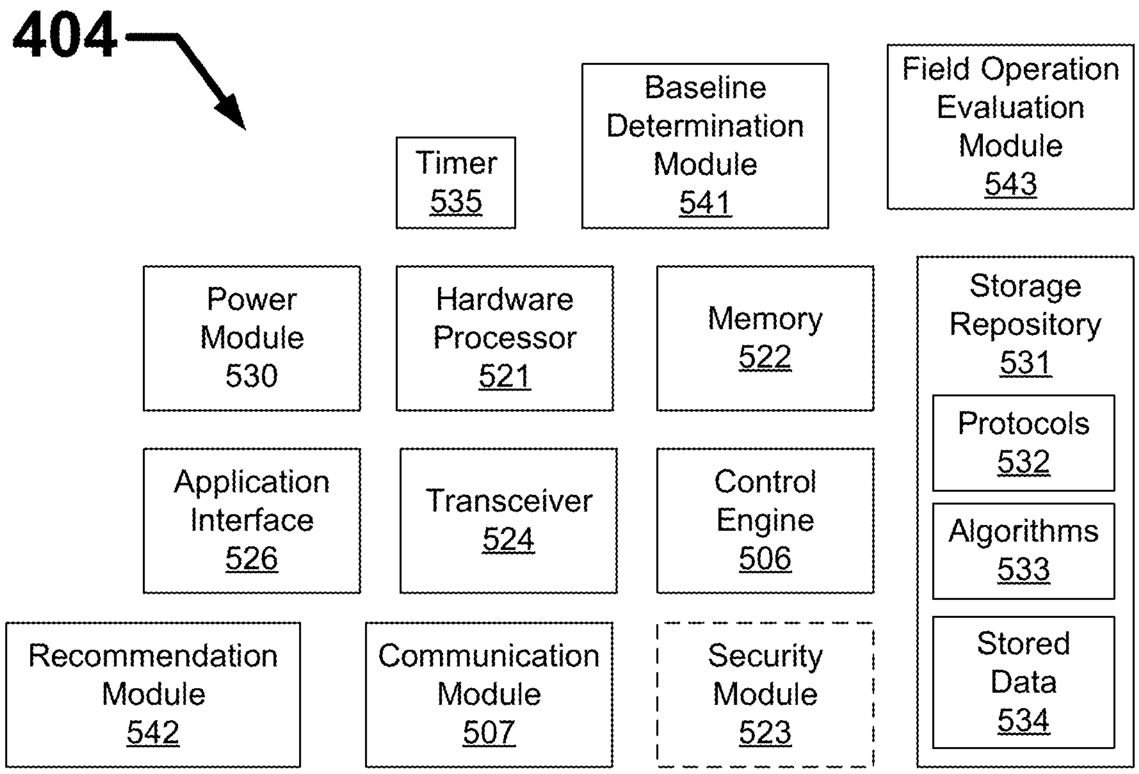
FIG. 5 shows a system diagram of a controller according to certain example embodiments.

A controller 404 may include one or more of a number of components. For example, as shown in FIG. 5, such components of a controller 404 may include, but are not limited to, a control engine 506, a baseline determination module 541, a recommendation module 542, a field operation evaluation module 543, a communication module 507, a timer 535, a power module 530, a storage repository 531, a hardware processor 521, a memory 522, a transceiver 524, an application interface 526, and, optionally, a security module 523. A controller 404 (or components thereof) may be located at or near the various components of the analytic system 450. In addition, or in the alternative, the controller 404 (or components thereof) may be located remotely from (e.g., in the cloud, at an office building) the various components of the analytic system 450.

In certain example embodiments, a controller 404 may be used to implement and/or alter a parameter (e.g., a design parameter for a current wellbore 420, an operating parameter for a current wellbore 420, a design parameter for a different wellbore 420 in the subterranean formation (e.g., subterranean formation 110, subterranean formation 210) an operating parameter for a different wellbore 420 in the subterranean formation) of a field operation. When there are multiple controllers 404 (e.g., one controller 404 for a testing apparatus 470, another controller 404 for a fluid component source 428, yet another controller 404 for the processing system 495), each controller 404 may operate independently of each other. Alternatively, two or more of the multiple controllers 404 may work cooperatively with each other. As yet another alternative, one of the controllers 404 may control some or all of one or more other controllers 404 in the system 400 or portion thereof. Each controller 404 may be considered a type of computer device, as discussed below with respect to FIG. 6.

The storage repository 531 may be a persistent storage device (or set of devices) that stores software and data used to assist a controller 404 in communicating with one or more other components of a system, such as the users 451 (including associated user systems 455), each well 420, each fluid component source 428, the processing system 495, the controllers 304, the sensor devices 360, other controllers 404 of the analytic system 450, the network manager 480, the sensor devices 460, etc. of the system 400 of FIG. 4 above. In one or more example embodiments, the storage repository 531 stores one or more protocols 532, one or more algorithms 533, and stored data 534.

The protocols 532 of the storage repository 531 may be any procedures (e.g., a series of method steps) and/or other similar operational processes that the control engine 506 of the controller 404 follows based on certain conditions at a point in time. The protocols 532 may include any of a number of communication protocols that are used to send and/or obtain data between a controller 404 and other components of a system (e.g., the system 400). Such protocols 532 used for communication may be time-synchronized protocols. Examples of such time-synchronized protocols may include, but are not limited to, a highway addressable remote transducer (HART) protocol, a WirelessHART protocol, and an International Society of Automation (ISA) 100 protocol. In this way, one or more of the protocols 532 may provide a layer of security to the data transferred within a system (e.g., the system 400). Other protocols 532 used for communication may be associated with the use of Wi-Fi, Zigbee, visible light communication (VLC), cellular networking, BLE, UWB, and Bluetooth.

The algorithms 533 may be any formulas, mathematical models, forecasts, simulations, and/or other similar tools that the control engine 506 of a controller 404 uses to reach a computational conclusion. For example, one or more algorithms 533 may be used, in conjunction with one or more protocols 532, to assist a controller 404 to determine when to start, adjust, and/or stop the operation of a well 420, a fluid component source 428, a testing apparatus 470, the processing system 495, a sensor device 460, and/or another controller 404 of the analytic system 450. As another example, one or more algorithms 533 may be used, in conjunction with one or more protocols 532, to assist a controller 404 to determine when to have a sensor device 460 measure a parameter and subsequently assist the controller 404 in performing a calculation or make a determination using the measurement.

As yet another example, one or more algorithms 533 may be used, in conjunction with one or more protocols 532, to assist a controller 404 to identify an optimal (e.g., most cost effective, most likely to generate a target chemistry of the water and/or other parts of a sample 447) or recommended fluid component 427 based on the composition of the samples 447 to be mixed with the fluid component to form a fluid 437. As still another example, one or more algorithms 533 may be used, in conjunction with one or more protocols 532, to assist a controller 404 in identifying and tracking the composition of water in the samples 447 from a well 420 and evaluating the actual composition of the water and/or other parts of the samples 447 against the anticipated composition of the water and/or other parts of the samples 447.

Stored data 534 may be any data associated with a field (e.g., the subterranean formation 110, the fractures 101 within the volume 190 adjacent to a wellbore 120, the characteristics of proppant 112 used in a field operation, composition of the water and/or other parts of the samples 447), other fields (e.g., other wellbores and subterranean formations), the other components (e.g., the user systems 455, the testing apparatuses 470, the sensor devices 460, the sensor devices 360, the controllers 304, the fluid components 427, the processing system 495), including associated equipment (e.g., motors, pumps, compressors), of the system 400, measurements made by the sensor devices 460 and the sensor devices 360, threshold values, tables, results of previously run or calculated algorithms 533, updates to protocols 532, user preferences, and/or any other suitable data. Such data may be any type of data, including but not limited to historical data, present data, and future data (e.g., forecasts). The stored data 534 may be associated with some measurement of time derived, for example, from the timer 535.

Examples of a storage repository 531 may include, but are not limited to, a database (or a number of databases), a file system, cloud-based storage, a hard drive, flash memory, some other form of solid-state data storage, or any suitable combination thereof. The storage repository 531 may be located on multiple physical machines, each storing all or a portion of the communication protocols 532, the algorithms 533, and/or the stored data 534 according to some example embodiments. Each storage unit or device may be physically located in the same or in a different geographic location.

The storage repository 531 may be operatively connected to the control engine 506. In one or more example embodiments, the control engine 506 includes functionality to communicate with the users 451 (including associated user systems 455), the testing apparatuses 470, the processing system 495, the sensor devices 460, the sensor devices 360, the controllers 304, the network manager 480, and/or the other components in the system 400. More specifically, the control engine 506 sends information to and/or obtains information from the storage repository 531 in order to communicate with the users 451 (including associated user systems 455), the testing apparatuses 470, the processing system 495, the sensor devices 460, the sensor devices 360, the controllers 304, the network manager 480, and/or the other components of the system 400. As discussed below, the storage repository 531 may also be operatively connected to the communication module 507 in certain example embodiments.

In certain example embodiments, the control engine 506 of a controller 404 controls the operation of one or more components (e.g., the communication module 507, the timer 535, the transceiver 524) of the controller 404. For example, the control engine 506 may activate the communication module 507 when the communication module 507 is in "sleep" mode and when the communication module 507 is needed to send data obtained from another component (e.g., a sensor device 460) in the system 400. In addition, the control engine 506 of a controller 404 may control the operation of one or more other components (e.g., a testing apparatus 470, the processing system 495, a fluid component source 428, a well 420), or portions thereof, of the system 400.

The control engine 506 of a controller 404 may communicate with one or more other components of the system 400. For example, the control engine 506 may use one or more protocols 532 to facilitate communication with the sensor devices 460 to obtain data (e.g., measurements of various parameters, such as water chemistry, temperature, pressure, and flow rate), whether in real time or on a periodic basis and/or to instruct a sensor device 460 to take a measurement. As another example, the control engine 506 may use one or more algorithms 533 and/or protocols 532 to decide which tests (e.g., determining an ion concentration, determining an ion ratio, determining an amount of a stable isotope) to perform on the samples 447 from a well 420.

As yet another example, the control engine 506 may use one or more algorithms 533 and/or protocols 532 to generate a new algorithm 533 that provides expected results using the baseline for a well 420. As still another example, the control engine 506 may use one or more algorithms 533 and/or protocols 532 to determine, using the results of testing the one or more parameters associated with the samples 447, a volume of the field operation fluid (e.g., fracturing fluid when the field operation includes fracturing, saltwater when the field operation is injecting the saltwater into a well 420 configured as an injection well, a fluid (e.g., water) when the field operation is utilizing a geothermal resource by heating the fluid and/or creating steam) that migrates through a FDI (defined below) to one or more wells 420, whether during and/or after the field operation. A number of other capabilities of the control engine 506 (as well as the controller 404 as a whole and/or other portions of the controller 404) are discussed below with respect to FIG. 7.

The control engine 506 may generate and process data associated with control, communication, and/or other signals sent to and obtained from the users 451 (including associated user systems 455), the sensor devices 460, the sensor devices 360, the controllers 304, the other controllers 404 of the analytic system 450, the fluid component sources 428, the conveyance system 488, the network manager 480, and the other components of the system 400. In certain embodiments, the control engine 506 of the controller 404 may communicate with one or more components of a system external to the system 400. For example, the control engine 506 may interact with an inventory management system by ordering replacements for components or pieces of equipment (e.g., a sensor device 460, a valve 485, a motor) within the system 400 that has failed or is failing. As another example, the control engine 506 may interact with a contractor or workforce scheduling system by arranging for the labor needed to replace a component or piece of equipment in the system 400. In this way and in other ways, the controller 404 is capable of performing a number of functions beyond what could reasonably be considered a routine task.

In certain example embodiments, the control engine 506 may include an interface that enables the control engine 506 to communicate with the sensor devices 460, the sensor devices 360, the controllers 304, the other controllers 404 of the analytic system 450, the fluid component sources 428, the conveyance system 488, the user systems 455, the network manager 480, and/or other components of the system 400. For example, if a user system 455 operates under IEC Standard 62386, then the user system 455 may have a serial communication interface that will transfer data to the controller 404. Such an interface may operate in conjunction with, or independently of, the protocols 532 used to communicate between the controller 404 and the users 451 (including corresponding user systems 455), the sensor devices 460, the sensor devices 360, the controllers 304, the other controllers 404 of the analytic system 450, the fluid component sources 428, the conveyance system 488, the network manager 480, and the other components of the system 400.

The control engine 506 (or other components of the controller 404) may also include one or more hardware components and/or software elements to perform its functions. Such components may include, but are not limited to, a universal asynchronous receiver/transmitter (UART), a serial peripheral interface (SPI), a direct-attached capacity (DAC) storage device, an analog-to-digital converter, an inter-integrated circuit (I2C), and a pulse width modulator (PWM).

The baseline determination module 541 of the controller 404 may be configured to determine a baseline for one or more of the wells 420. For example, the baseline determination module 541 may use measurements of parameters taken by one or more of the sensor devices 460, where the parameters are associated with the samples 447 or portions thereof (e.g., produced water) from a well 420. Using one or more protocols 532 and/or one or more algorithms 533, the baseline determination module 541 may generate a baseline of the parameters associated with the samples 447 (e.g., samples 447-1, samples 447-X) for each well 420 (well 420-1, well 420-X). In addition, the baseline determination module 541 may also be configured to modify an existing baseline using measurements of one or more parameters by one or more sensor devices 460, one or more protocols 532, one or more algorithms 533, and/or stored data 534.

Implementation of the functions of the baseline determination module 541 may be performed in one or more of a number of ways. For example, the baseline determination module 541 may determine a difference in at least one parameter between a baseline and results of testing the samples 447 or portions thereof (e.g., produced water) for at least one of the wells 420 during a field operation, where the difference exceeds a threshold parameter value (e.g., part of the stored data 534) for the at least one parameter.

The recommendation module 542 of the controller 404 may be configured to generate a recommendation regarding one or more of the wells 420. For example, the recommendation module 542 may use one or more protocols 532 and/or one or more algorithms 533 to generate a recommendation as to particular features (e.g., a particular fluid 437 to be used, a flow rate of the fluid 437, a pressure of the fluid 437, a particular well 420 to target, a duration, a start date and time) of a field operation and/or one or more particular wells 420 to direct the field operation. In some cases, the recommendation module 542 may also modify one or more of the features of a field operation that is in progress.

As another example, the recommendation module 542 may use one or more protocols 532 and/or one or more algorithms 533 to recommend an alteration of a chemical composition of a fluid (also sometimes called a field operation fluid) used for a field operation. As yet another example, the recommendation module 542 may use one or more protocols 532 and/or one or more algorithms 533 to recommend an alteration of altering at least one parameter (e.g., a flow rate, a pressure, a temperature) of the field operation fluid.

Implementation of the functions of the recommendation module 542 may be performed in one or more of a number of ways. For example, the recommendation module 542 may use one or more algorithms 533 and/or protocols 532 to determine that a difference between the results and the expected results exceeds a threshold forecast value. In such a case, the recommendation module 542 may use one or more algorithms 533 and/or protocols 532 to generate a revision to the algorithm 533 (e.g., a forecasting model) based on the difference. As another example, the recommendation module 542 may use one or more algorithms 533 and/or protocols 532 to generate a recommendation for a subsequent well 420 added to a pad of existing wells 420.

The field operation evaluation module 543 of the controller 404 may be configured to evaluate a field operation currently being performed or planned to be performed on one or more of the wells 420. For example, the operation evaluation module 543 may use one or more protocols 532 and/or one or more algorithms 533, as well as measurements of one or more parameters made by one or more sensor devices 460, to compare the results of testing samples 447 from a well 420 during a field operation to expected results generated by one or more algorithms 533 (e.g., a forecasting model). Any differences that exceed a threshold value may be used by the field operation evaluation module 543 as a basis of evaluating the field operation.

Implementation of the functions of the field operation evaluation module 543 may be performed in one or more of a number of ways. For example, the field operation evaluation module 543 may use one or more algorithms 533 and/or protocols 532 to recommend a change to a field operation based on a difference determined between the baseline and the results of testing the samples 447 from one or more wells 420 during the field operation.

The communication module 507 of the controller 404 determines and implements the communication protocol (e.g., from the protocols 532 of the storage repository 531) that is used when the control engine 506 communicates with (e.g., sends signals to, obtains signals from) the user systems 455, the sensor devices 460, the sensor devices 360, the controllers 304, the other controllers 404 of the analytic system 450, the fluid component sources 428, the conveyance system 488, the network manager 480, and the other components of the system 400. In some cases, the communication module 507 accesses the stored data 534 to determine which communication protocol is used to communicate with another component of the system 400. In addition, the communication module 507 may identify and/or interpret the communication protocol of a communication obtained by the controller 404 so that the control engine 506 may interpret the communication. The communication module 507 may also provide one or more of a number of other services with respect to data sent from and obtained by the controller 404. Such services may include, but are not limited to, data packet routing information and procedures to follow in the event of data interruption.

The timer 535 of the controller 404 may track clock time, intervals of time, an amount of time, and/or any other measure of time. The timer 535 may also count the number of occurrences of an event, whether with or without respect to time. Alternatively, the control engine 506 may perform a counting function. The timer 535 is able to track multiple time measurements and/or count multiple occurrences concurrently. The timer 535 may track time periods based on an Instruction obtained from the control engine 506, based on an instruction obtained from a user 451, based on an instruction programmed in the software for the controller 404, based on some other condition (e.g., the occurrence of an event) or from some other component, or from any combination thereof. In certain example embodiments, the timer 535 may provide a time stamp for each packet of data obtained from another component (e.g., a sensor device 460) of the system 400.

The power module 530 of the controller 404 obtains power from a power supply (e.g., AC mains) and manipulates (e.g., transforms, rectifies, inverts) that power to provide the manipulated power to one or more other components (e.g., the timer 535, the control engine 506) of the controller 404, where the manipulated power is of a type (e.g., alternating current, direct current) and level (e.g., 12V, 24V, 120V) that may be used by the other components of the controller 404. In some cases, the power module 530 may also provide power to one or more of the sensor devices 460.

The power module 530 may include one or more of a number of single or multiple discrete components (e.g., transistor, diode, resistor, transformer) and/or a microprocessor. The power module 530 may include a printed circuit board, upon which the microprocessor and/or one or more discrete components are positioned. In addition, or in the alternative, the power module 530 may be a source of power in itself to provide signals to the other components of the controller 404. For example, the power module 530 may be or include an energy storage device (e.g., a battery). As another example, the power module 530 may be or include a localized photovoltaic power system.

The hardware processor 521 of the controller 404 executes software, algorithms (e.g., algorithms 533), and firmware in accordance with one or more example embodiments. Specifically, the hardware processor 521 may execute software on the control engine 506 or any other portion of the controller 404, as well as software used by the users 451 (including associated user systems 455), the network manager 480, and/or other components of the system 400. The hardware processor 521 may be an integrated circuit, a central processing unit, a multi-core processing chip, SoC, a multi-chip module including multiple multi-core processing chips, or other hardware processor in one or more example embodiments. The hardware processor 521 may be known by other names, including but not limited to a computer processor, a microprocessor, and a multi-core processor.

In one or more example embodiments, the hardware processor 521 executes software instructions stored in memory 522. The memory 522 includes one or more cache memories, main memory, and/or any other suitable type of memory. The memory 522 may include volatile and/or non-volatile memory. The memory 522 may be discretely located within the controller 404 relative to the hardware processor 521. In certain configurations, the memory 522 may be integrated with the hardware processor 521.

In certain example embodiments, the controller 404 does not include a hardware processor 521. In such a case, the controller 404 may include, as an example, one or more field programmable gate arrays (FPGA), one or more insulated-gate bipolar transistors (IGBTs), and/or one or more integrated circuits (ICs). Using FPGAs, IGBTs, ICs, and/or other similar devices known in the art allows the controller 404 (or portions thereof) to be programmable and function according to certain logic rules and thresholds without the use of a hardware processor. Alternatively, FPGAs, IGBTs, ICs, and/or similar devices may be used in conjunction with one or more hardware processors 521.

The transceiver 524 of the controller 404 may send and/or obtain control and/or communication signals. Specifically, the transceiver 524 may be used to transfer data between the controller 404 and the users 451 (including associated user systems 455), the sensor devices 460, the sensor devices 360, the controllers 304, the other controllers 404 of the analytic system 450, the fluid component sources 428, the conveyance system 488, the network manager 480, and the other components of the system 400. The transceiver 524 may use wired and/or wireless technology. The transceiver 524 may be configured in such a way that the control and/or communication signals sent and/or obtained by the transceiver 524 may be obtained and/or sent by another transceiver that is part of a user system 455, a sensor device 460, the sensor devices 360, the controllers 304, the other controllers 404 of the analytic system 450, the fluid component sources 428, the conveyance system 488, the network manager 480, and/or another component of the system 400. The transceiver 524 may send and/or obtain any of a number of signal types, including but not limited to radio frequency signals.

When the transceiver 524 uses wireless technology, any type of wireless technology may be used by the transceiver 524 in sending and obtaining signals. Such wireless technology may include, but is not limited to, Wi-Fi, Zigbee, VLC, cellular networking, BLE, UWB, and Bluetooth. The transceiver 524 may use one or more of any number of suitable communication protocols (e.g., ISA100, HART) when sending and/or obtaining signals.

Optionally, in one or more example embodiments, the security module 523 secures interactions between the controller 404, the users 451 (including associated user systems 455), the sensor devices 460, the sensor devices 360, the controllers 304, the other controllers 404 of the analytic system 450, the fluid component sources 428, the conveyance system 488, the network manager 480, and the other components of the system 400. More specifically, the security module 523 authenticates communication from software based on security keys verifying the identity of the source of the communication. For example, user software may be associated with a security key enabling the software of a user system 455 to interact with the controller 404. Further, the security module 523 may restrict receipt of information, requests for information, and/or access to information.

A user 451 may be any person that interacts, directly or indirectly, with a controller 404 and/or any other component of the testing system 400. Examples of a user 451 may include, but are not limited to, a business owner, an engineer, a company representative, a geologist, a consultant, a drilling engineer, a contractor, and a manufacturer's representative. A user 451 may use one or more user systems 455, which may include a display (e.g., a GUI). A user system 455 of a user 451 may interact with (e.g., send data to, obtain data from) the controller 404 via an application interface and using the communication links 405. The user 451 may also interact directly with the controller 404 through a user interface (e.g., keyboard, mouse, touchscreen).

The network manager 480 is a device or component that controls all or a portion (e.g., a communication network, the controller 404) of the system 400. The network manager 480 may be substantially similar to some or all of the controller 404, as described above. For example, the network manager 480 may include a controller that has one or more components and/or similar functionality to some or all of the controller 404. Alternatively, the network manager 480 may include one or more of a number of features in addition to, or altered from, the features of the controller 404. As described herein, control and/or communication with the network manager 480 may include communicating with one or more other components of the same system 400 and/or another system. In such a case, the network manager 480 may facilitate such control and/or communication. The network manager 480 may be called by other names, including but not limited to a master controller, a network controller, and an enterprise manager. The network manager 480 may be considered a type of computer device, as discussed below with respect to FIG. 6.

Interaction between each controller 404, the sensor devices 460, the sensor devices 360, the controllers 304, the other controllers 404 of the analytic system 450, the fluid component sources 428, the conveyance system 488, the users 451 (including any associated user systems 455), the network manager 480, and other components (e.g., the valves 485, the wells 420) of the system 400 may be conducted using communication links 405 and/or power transfer links 487. Each communication link 405 may include wired (e.g., Class 1 electrical cables, Class 2 electrical cables, electrical connectors, Power Line Carrier, RS485) and/or wireless (e.g., Wi-Fi, Zigbee, visible light communication, cellular networking, Bluetooth, Bluetooth Low Energy (BLE), ultrawide band (UWB), WirelessHART, ISA100) technology. A communication link 405 may transmit signals (e.g., communication signals, control signals, data) between each controller 404, the sensor devices 460, the sensor devices 360, the controllers 304, the other controllers 404 of the analytic system 450, the fluid component sources 428, the conveyance system 488, the users 451 (including any associated user systems 455), the network manager 480, and the other components of the system 400.

Each power transfer link 487 may include one or more electrical conductors, which may be individual or part of one or more electrical cables. In some cases, as with inductive power, power may be transferred wirelessly using power transfer links 487. A power transfer link 487 may transmit power between each controller 404, the sensor devices 460, the sensor devices 360, the controllers 304, the other controllers 404 of the analytic system 450, the fluid component sources 428, the conveyance system 488, the users 451 (including any associated user systems 455), the network manager 480, and the other components of the system 400. Each power transfer link 487 may be sized (e.g., 12 gauge, 18 gauge, 4 gauge) in a manner suitable for the amount (e.g., 480V, 24V, 120V) and type (e.g., alternating current, direct current) of power transferred therethrough.

Each of the controllers 304 is a device or component that controls a portion (e.g., a communication network, some of the field equipment 109) of the system 400. A controller 304 may be substantially similar to some or all of the controller 404, as described above. For example, a controller 304 may include a controller that has one or more components and/or similar functionality to some or all of the controller 404. Alternatively, a controller 304 may include one or more of a number of features in addition to, or altered from, the features of the controller 404. As described herein, control and/or communication with a controller 304 may include communicating with one or more other components of the same system 400 and/or another system. In such a case, a controller 304 may facilitate such control and/or communication. Each controller 304 may be considered a type of computer device, as discussed below with respect to FIG. 6.

A user 451 (which may include an associated user system 455), the sensor devices 460, the sensor devices 360, the controllers 304, the other controllers 404 of the analytic system 450, the fluid component sources 428, the conveyance system 488, the network manager 480, and the other components of the system 400 may interact with a controller 404 using the application interface 526. Specifically, the application interface 526 of a controller 404 obtains data (e.g., information, communications, instructions, updates to firmware) from and sends data (e.g., information, communications, instructions) to the user systems 455 of the users 451, the sensor devices 460, the sensor devices 360, the controllers 304, the other controllers 404 of the analytic system 450, the fluid component sources 428, the conveyance system 488, the network manager 480, and/or the other components of the system 400. Examples of an application interface 526 may be or include, but are not limited to, an application programming interface, a web service, a data protocol adapter, some other hardware and/or software, or any suitable combination thereof. Similarly, the user systems 455 of the users 451, the sensor devices 460, the sensor devices 360, the controllers 304, the other controllers 404 of the analytic system 450, the fluid component sources 428, the conveyance system 488, the network manager 480, and/or the other components of the system 400 may include an interface (similar to the application interface 526 of the controller 404) to obtain data from and send data to a controller 404 in certain example embodiments.

In addition, as discussed above with respect to a user system 455 of a user 451, one or more of the sensor devices 460, one or more of the sensor devices 360, one or more of the controllers 304, one or more of the other controllers 404 of the analytic system 450, one or more of the fluid component sources 428, some or all of the conveyance system 488, the network manager 480, and/or one or more of the other components (or portions thereof) of the system 400 may include a user interface. Examples of such a user interface may include, but are not limited to, a graphical user interface, a touchscreen, a keyboard, a monitor, a mouse, some other hardware, or any suitable combination thereof.

The controller 404, the users 451 (including associated user systems 455), the sensor devices 460, the sensor devices 360, the controllers 304, the other controllers 404 of the analytic system 450, the fluid component sources 428, the conveyance system 488, the network manager 480, and the other components of the system 400 may use their own system or share a system in certain example embodiments. Such a system may be, or contain a form of, an Internet-based or an intranet-based computer system that is capable of communicating with various software. A computer system includes any type of computing device and/or communication device, including but not limited to a controller 404. Examples of such a system may include, but are not limited to, a desktop computer with a Local Area Network (LAN), a Wide Area Network (WAN), Internet or intranet access, a laptop computer with LAN, WAN, Internet or intranet access, a smart phone, a server, a server farm, an android device (or equivalent), a tablet, smartphones, and a personal digital assistant (PDA). Such a system may correspond to a computer system as described below with regard to FIG. 6.

Further, as discussed above, such a system may have corresponding software (e.g., user system software, sensor device software, controller software). The software may execute on the same or a separate device (e.g., a server, mainframe, desktop personal computer (PC), laptop, PDA, television, cable box, satellite box, kiosk, telephone, mobile phone, or other computing devices) and may be coupled by the communication network (e.g., Internet, Intranet, Extranet, LAN, WAN, or other network communication methods) and/or communication channels, with wire and/or wireless segments according to some example embodiments. The software of one system may be a part of, or operate separately but in conjunction with, the software of another system within the system 400.

Figure 6:
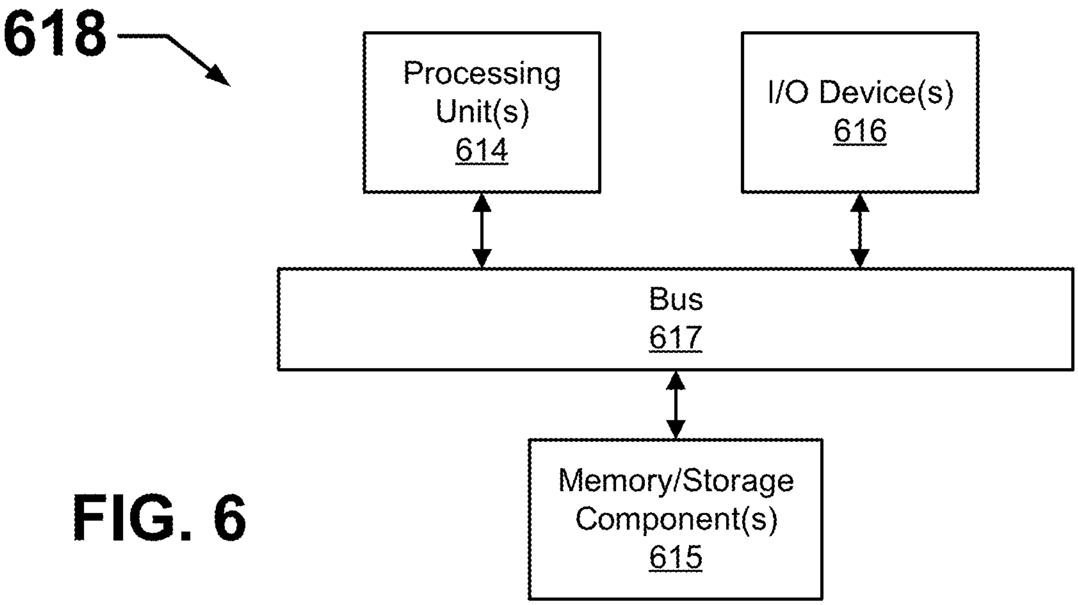
FIG. 6 shows a computing device in accordance with certain example embodiments.

FIG. 6 illustrates one embodiment of a computing device 618 that implements one or more of the various techniques described herein, and which is representative, in whole or in part, of the elements described herein pursuant to certain example embodiments. For example, a controller 404 (including components thereof, such as a control engine 506, a hardware processor 521, a storage repository 531, a power module 530, and a transceiver 524) may be considered a computing device 618 (also called a computer system 618 herein). Computing device 618 is one example of a computing device and is not intended to suggest any limitation as to scope of use or functionality of the computing device and/or its possible architectures. Neither should the computing device 618 be interpreted as having any dependency or requirement relating to any one or combination of components illustrated in the example computing device 618.

The computing device 618 includes one or more processors or processing units 614, one or more memory/storage components 615, one or more input/output (I/O) devices 616, and a bus 617 that allows the various components and devices to communicate with one another. The bus 617 represents one or more of any of several types of bus structures, including a memory bus or memory controller, a peripheral bus, an accelerated graphics port, and a processor or local bus using any of a variety of bus architectures. The bus 617 includes wired and/or wireless buses.

The memory/storage component 615 represents one or more computer storage media. The memory/storage component 615 includes volatile media (such as random access memory (RAM)) and/or nonvolatile media (such as read only memory (ROM), flash memory, optical disks, magnetic disks, and so forth). The memory/storage component 615 includes fixed media (e.g., RAM, ROM, a fixed hard drive, etc.) as well as removable media (e.g., a Flash memory drive, a removable hard drive, an optical disk, and so forth).

One or more I/O devices 616 allow a user 451 to enter commands and information to the computing device 618, and also allow information to be presented to the user 451 and/or other components or devices. Examples of input devices 616 include, but are not limited to, a keyboard, a cursor control device (e.g., a mouse), a microphone, a touchscreen, and a scanner. Examples of output devices include, but are not limited to, a display device (e.g., a monitor or projector), speakers, outputs to a lighting network (e.g., DMX card), a printer, and a network card.

Various techniques are described herein in the general context of software or program modules. Generally, software includes routines, programs, objects, components, data structures, and so forth that perform particular tasks or implement particular abstract data types. An implementation of these modules and techniques are stored on or transmitted across some form of computer readable media. Computer readable media is any available non-transitory medium or non-transitory media that is accessible by a computing device. By way of example, and not limitation, computer readable media includes "computer storage media".

"Computer storage media" and "computer readable medium" include volatile and non-volatile, removable and non-removable media implemented in any method or technology for storage of information such as computer readable instructions, data structures, program modules, or other data. Computer storage media include, but are not limited to, computer recordable media such as RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which is used to store the desired information and which is accessible by a computer.

The computer device 618 is connected to a network (not shown) (e.g., a LAN, a WAN such as the Internet, cloud, or any other similar type of network) via a network interface connection (not shown) according to some example embodiments. Those skilled in the art will appreciate that many different types of computer systems exist (e.g., desktop computer, a laptop computer, a personal media device, a mobile device, such as a cell phone or personal digital assistant, or any other computing system capable of executing computer readable instructions), and the aforementioned input and output means take other forms, now known or later developed, in other example embodiments. Generally speaking, the computer system 618 includes at least the minimal processing, input, and/or output means necessary to practice one or more embodiments.

Further, those skilled in the art will appreciate that one or more elements of the aforementioned computer device 618 is located at a remote location and connected to the other elements over a network in certain example embodiments. Further, one or more embodiments is implemented on a distributed system having one or more nodes, where each portion of the implementation (e.g., a fluid component source 428, a testing apparatus 470, the processing system 495) is located on a different node within the distributed system. In one or more embodiments, the node corresponds to a computer system. Alternatively, the node corresponds to a processor with associated physical memory in some example embodiments. The node alternatively corresponds to a processor with shared memory and/or resources in some example embodiments.

Figure 7A:
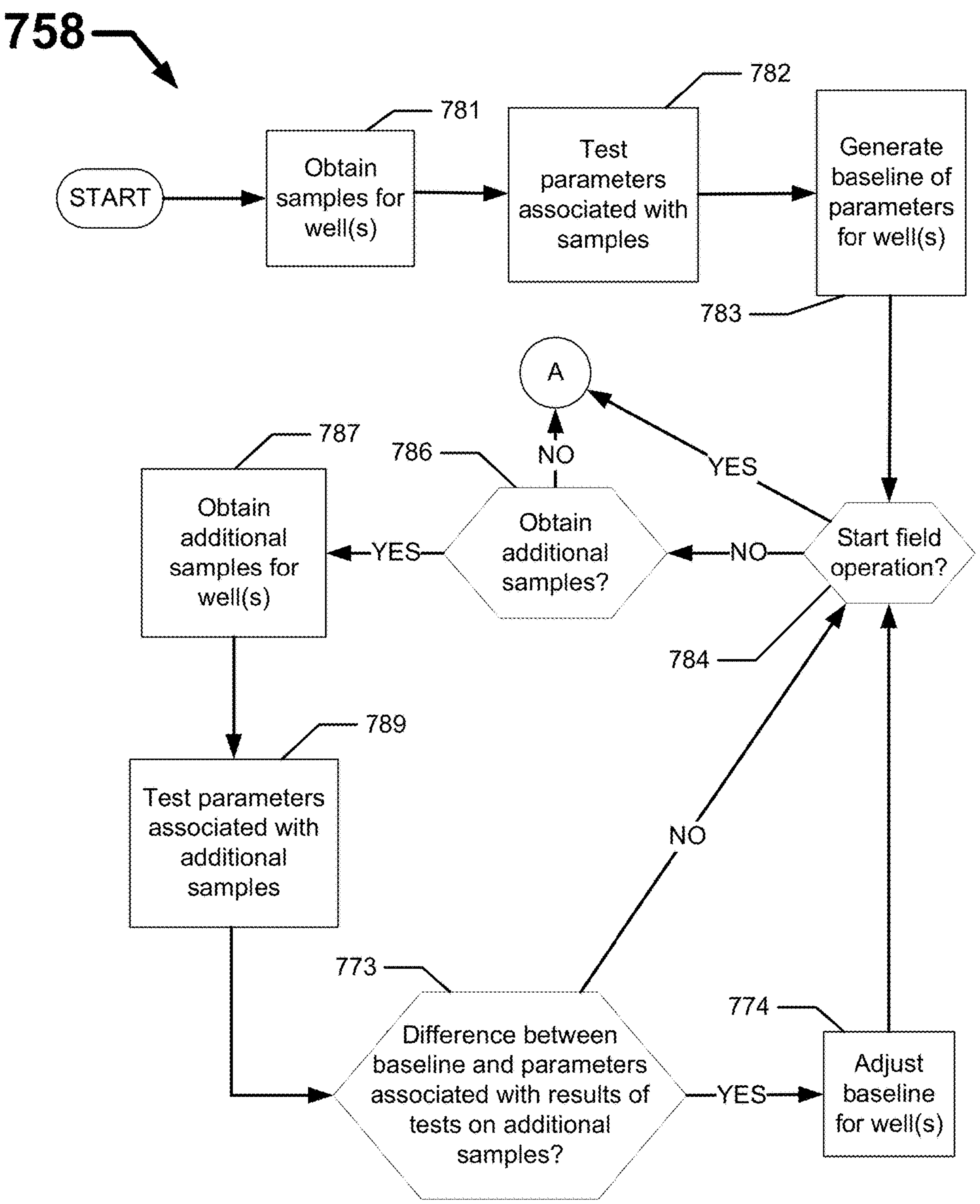
FIGS. 7A and 7B show a flowchart of a method for well evaluation using water chemistry analysis according to certain example embodiments.
Figure 7B:
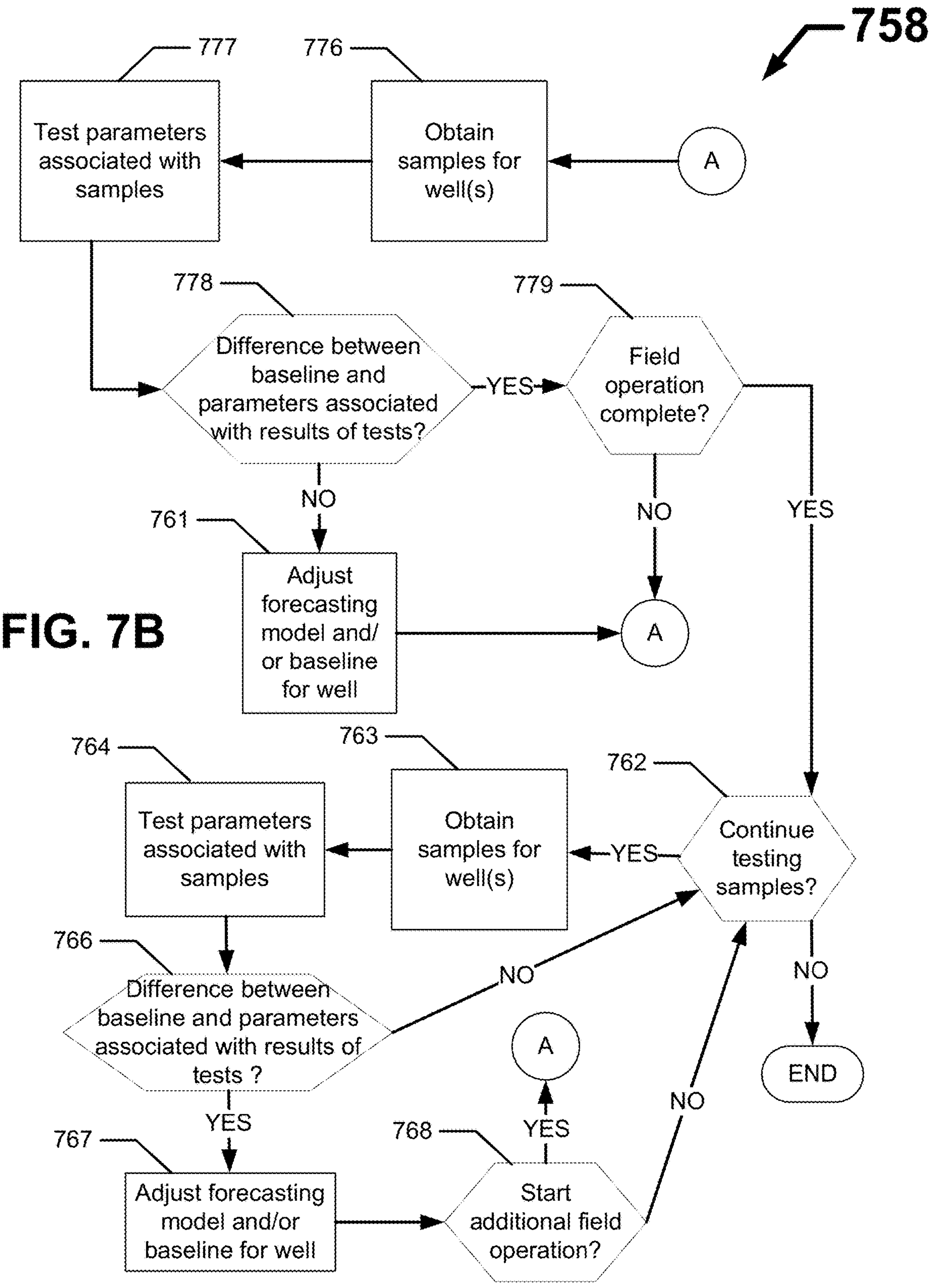

FIGS. 7A and 7B show a flowchart 758 of a method for evaluating one or more wells using water chemistry analysis according to certain example embodiments. While the various steps in this flowchart 758 are presented sequentially, one of ordinary skill will appreciate that some or all of the steps may be executed in different orders, may be combined or omitted, and some or all of the steps may be executed in parallel. Further, in one or more of the example embodiments, one or more of the steps shown in this example method may be omitted, repeated, and/or performed in a different order. Some or all of the steps of the method of FIGS. 7A and 7B may be performed off site (e.g., in a laboratory remote from a field operation). In addition, or in the alternative, some or all of the steps of the method of FIGS. 7A and 7B may be performed on site (e.g., in the field, adjacent to a wellbore 120) where a field operation is being performed or planned.

In addition, a person of ordinary skill in the art will appreciate that additional steps not shown in FIGS. 7A and 7B may be included in performing this method. Accordingly, the specific arrangement of steps should not be construed as limiting the scope. Further, a particular computing device, such as the computing device 618 discussed above with respect to FIG. 6, may be used to perform or facilitate the performance of one or more of the steps for the methods shown in FIGS. 7A and 7B in certain example embodiments. Any of the functions performed below by a controller 404 (an example of which is shown in FIG. 5) may involve the use of one or more protocols 532, one or more algorithms 533, and/or stored data 534 stored in a storage repository 531. In addition, or in the alternative, any of the functions in the method may be performed by a user (e.g., user 451).

The method shown in FIGS. 7A and 7B is merely an example that may be performed by using an example system described herein. In other words, systems for evaluating one or more wells using water chemistry analysis may perform other functions using other methods in addition to and/or aside from those shown in FIGS. 7A and 7B. Referring to FIGS. 1A through 7B, the method shown in the flowchart 758 of FIGS. 7A and 7B begins at the START step and proceeds to step 781, where samples 447 for multiple wells 420 is obtained. As used herein, the term "obtaining" may include collecting, receiving, retrieving, accessing, generating, etc. or any other manner of obtaining samples of the water 447 from a well 420. The samples 447 may be obtained from some or all wells 420 of a pad. The samples 447 obtained at this point in time are prior to a field operation. Each sample 447 may include some amount of water (e.g., produced water, formation water). Each sample 447 of this step 781 may be called a first sample or an initial sample.

Each sample 447 may be extracted from a wellbore 420 during a part (e.g., exploration, production, shut-in period) of a field operation. The samples 447 may be obtained at the surface (e.g., surface 108, surface 208) using field equipment 109, part of the conveyance system 488, and/or other equipment (e.g., pumps, compressors). Some or all of the process of obtaining the samples 447 from a well 420 may be controlled by a controller 404 (or a collecting component thereof) of the analytic system 450 using one or more protocols 532, one or more algorithms 533 (e.g., models), measurements of one or more sensor devices 460, input from a user 451 (which may include an associated user system 455), and/or any other source of information within the system 400. In addition, or in the alternative, some or all of the process of obtaining the samples 447 from a well 420 may be controlled by a user 451. The samples 447 may be obtained from a well 420 continuously over an extended period of time or on an iterative basis. The rate (e.g., daily, weekly, randomly) of collecting and testing samples 447 may vary (e.g., based on field operations, based on field conditions, based on business need, based on whether there is no significant change in the analyzed water chemistry) over time. Samples 447 from the same well 420 and/or different wells 420 may be obtained from different formation depths (e.g., as end members).

For some well networks, there may be existing (parent) wells 420 that are on production and other (child) wells 420 that have not yet been placed on production (e.g., planned wells 420, SWD wells 420 undergoing completion, wells 420 undergoing field operations related to exploration, wells 420 awaiting a fracturing operation). In such cases, this step 781, as well as step 782, step 783, step 786, step 787, step 789, and step 774, may apply to the some or all of the parent wells 420 and/or some or all of the child wells 420 that exist. One or more of the wells 420 during step 781, step 782, step 783, step 786, step 787, step 789, and step 774 may not shut in. To the extent that there is a well 420 that is shut in, step 781, step 782, step 783, step 786, step 787, step 789, and step 774 may not apply to that well 420 for the time that the shut in is effective.

In step 782, one or more parameters associated with the samples 447 are tested. Testing of the one or more parameters associated with the samples 447 may be conducted using one or more sensor devices 460 to measure the one or more parameters that are directly or indirectly associated with the samples 447. The parameters associated with the samples 447 may be tested at the surface (e.g., surface 108, surface 208). The parameters associated with the samples 447 that are tested may include, but are not limited to, the composition of the samples 447, the amount (concentration) of each part of the composition, the amount and type of TDSs in the samples 447, the state (e.g., liquid, solid) of each part of the composition, the temperature of the samples 447, and the viscosity of the samples 447. Some or all of the testing of one or more of the samples 447 may include water chemistry analysis.

Some or all of the process of testing the parameters associated with the samples 447 may be controlled by a controller 404 (or a collecting component thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, some or all of the process of testing the parameters associated with the samples 447 may be controlled by a user 451. The parameters associated with the samples 447 may be tested continuously over an extended period of time or on a discrete basis.

In some cases, the samples 447 may be processed by the processing system 495 before being tested and/or after being tested. In the latter case, the parameters associated with the samples 447 may be retested after the samples 447 has been processed. The samples 447 may be processed multiple times and/or tested multiple times. The samples 447 may be processed for any of a number of purposes, including but not limited to removing cuttings and other unwanted solids, changing the pH, and adding chemicals (e.g., a fluid component 427). The samples 447 may be processed using any of a number of appropriate equipment of the processing system 495, including but not limited to heaters, chillers, mixers, filters, agitators, pumps, and centrifuges.

Some or all of the processing of the samples 447 using the processing system 495 may be controlled by a controller 404 (or a collecting component thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, some or all of the processing of the samples 447 using the processing system 495 may be controlled by a user 451. The samples 447 may be processed using the processing system 495 continuously over an extended period of time or on a discrete basis.

In step 783, a baseline for one or more of the parameters of each of the wells 420 is generated. Some or all of the baseline may be generated by a controller 404 (or the baseline determination module 541 thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, some or all of the process of generating a baseline for the parameters associated with the samples 447 from a well 420 may be controlled by a user 451. The baseline for the parameters of a well 420 may be generated based on raw measurements made by sensor devices 460, adjusted measurements made by sensor devices 460, outputs of algorithms 533 (e.g., models) using measurements made by sensor devices 460 as inputs, some other information associated with measurements made by sensor devices 460, or any suitable combination thereof.

In some cases, generating a baseline for the parameters from a well 420 may include developing strategies and forecasts that may be used in one or more steps below. Chemistry calculations based on the results generated in this step 783 may be performed by a controller 404 (including portions thereof). In addition to modeling, lab testing and/or other evaluation methods, using the analytic system 450, may be used to evaluate the baseline for the parameters that was generated to determine if adjustments to the baseline need to be made. Generating a baseline for one or more of the parameters from a well 420 may be performed at the surface (e.g., surface 108, surface 208). The baseline for one or more of the parameters of a well 420 may be generated continuously over an extended period of time or on a discrete basis. If applicable, the baseline for one or more of the parameters of a well 420 may be evaluated against historical data, other present data, and/or forecasts.

In some cases, this step 783 also includes generating and/or calibrating a forecasting model (also sometimes called a simulation model) using the baseline and/or the values of the parameters associated with the samples that resulted from the testing prior to the field operation. The forecasting model may be or include one or more algorithms 533. Some or all of the forecasting model may be generated or calibrated by a controller 404 (or the baseline determination module 541 and/or the field operation evaluation module 543 thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, some or all of the process of generated or calibrated the forecasting model for the well 420 may be controlled by a user 451. The forecasting model for a well 420 may be generated or calibrated based on raw measurements made by sensor devices 460, adjusted measurements made by sensor devices 460, outputs of algorithms 533 (e.g., models) using measurements made by sensor devices 460 as inputs, some other information associated with measurements made by sensor devices 460, or any suitable combination thereof.

In some cases, generating and/or calibrating the forecasting model for the well 420 may include generating and/or calibrating strategies and forecasts. Chemistry calculations based on the results adjusted in this step 783 may be performed by a controller 404 (including portions thereof). In addition to modeling, lab testing and/or other evaluation methods, using the analytic system 450, may be used to evaluate the forecasting model for the well 420 that was generated and/or calibrated to determine if adjustments to the forecasting model and/or other aspects (e.g., other algorithms 533) of the well 420 need to be made. Generating and/or calibrating the forecasting model for the well 420 may be performed at the surface (e.g., surface 108, surface 208). The forecasting model for the well 420 may be generated and/or calibrated continuously over an extended period of time or on a discrete basis. If applicable, the forecasting model for the well 420 may be generated and/or calibrated based on historical data, other present data, and/or forecasts.

In step 784, a determination is made as to whether a field operation has started. The field operation may be directly applied to one or more of the wells 420. The effects of the field operation may affect those same wells 420, as well as one or more other wells 420 in the subterranean formation (e.g., subterranean formation 110, subterranean formation 210). The determination may be made by a controller 404 (or the field operation evaluation module 543 thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, the determination may be made by a user 451. The determination may be made at the surface (e.g., surface 108, surface 208). If a field operation has started, then the process proceeds to step 776. If a field operation has not started, then the process proceeds to step 786.

In step 786, a determination is made as to whether additional samples 447 have been obtained from one or more of the wells 420. The determination may be made by a controller 404 (or a selecting component thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, the determination may be made by a user 451. The determination may be made at the surface (e.g., surface 108, surface 208). If additional samples 447 have been obtained from one or more of the wells 420, then the process proceeds to step 787. If additional samples 447 have not been obtained from one or more of the wells 420, then the process proceeds to step 776.

In step 787, additional samples 447 are obtained. The additional samples 447 may be obtained from one well 420 or multiple wells 420 of a pad. The additional samples 447 obtained at this point in time is prior to a field operation and is sometimes referred to herein as first samples. The additional samples 447 may be extracted from a wellbore 420 during a part of a field operation. The additional samples 447 may be obtained at the surface (e.g., surface 108, surface 208) using field equipment 109, part of the conveyance system 488, and/or other equipment (e.g., pumps, compressors).

Some or all of the process of obtaining the additional samples 447 from a well 420 may be controlled by a controller 404 (or a collecting component thereof) of the analytic system 450 using one or more protocols 532, one or more algorithms 533 (e.g., models), measurements of one or more sensor devices 460, input from a user 451 (which may include an associated user system 455), and/or any other source of information within the system 400. In addition, or in the alternative, some or all of the process of obtaining the additional samples 447 from a well 420 may be controlled by a user 451. The additional samples 447 may be obtained from a well 420 continuously over an extended period of time or on an iterative basis. The rate (e.g., daily, weekly, randomly) of collecting and testing samples 447 may vary (e.g., based on field operations, based on field conditions, based on business need, based on whether there is no significant change in the analyzed water chemistry) over time. Samples 447 from the same well 420 and/or different wells 420 may be obtained from different formation depths (e.g., as end members).

In step 789, one or more parameters associated with the additional samples 447 is tested. Testing of the one or more parameters associated with the additional samples 447 may be conducted using one or more sensor devices 460 to measure the one or more parameters that are directly or indirectly associated with the additional samples 447. The parameters associated with the additional samples 447 may be tested at the surface (e.g., surface 108, surface 208). The parameters associated with the additional samples 447 that are tested may be the same as, or different than, the parameters associated with the samples 447 that are tested in step 782.

Some or all of the process of testing the parameters associated with the additional samples 447 may be controlled by a controller 404 (or a collecting component thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, some or all of the process of testing the parameters associated with the additional samples 447 may be controlled by a user 451. The parameters associated with the additional samples 447 may be tested continuously over an extended period of time or on a discrete basis.

In some cases, the additional samples 447 may be processed by the processing system 495 before being tested and/or after being tested. In the latter case, the parameters associated with the additional samples 447 may be retested after the additional samples 447 has been processed. The additional samples 447 may be processed multiple times and/or tested multiple times. The additional samples 447 may be processed for any of a number of purposes, including but not limited to removing cuttings and other unwanted solids, changing the pH, and adding chemicals (e.g., a fluid component 427). The additional samples 447 may be processed using any of a number of appropriate equipment of the processing system 495, including but not limited to heaters, chillers, mixers, filters, agitators, pumps, and centrifuges.

Some or all of the processing of the additional samples 447 using the processing system 495 may be controlled by a controller 404 (or a collecting component thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, some or all of the processing of the additional samples 447 using the processing system 495 may be controlled by a user 451. The additional samples 447 may be processed using the processing system 495 continuously over an extended period of time or on a discrete basis.

In step 773, a determination is made as to whether there is a difference between the baseline for the water 447 and the parameters associated with results of the tests on the additional samples 447. In certain example embodiments, the samples 447 and the additional samples 447 are obtained from the same well 420 (e.g., at approximately the same depth). In some cases, the difference between the baseline for parameters associated with the results of the tests on the samples 447 and the parameters associated with the results of the tests on the additional samples 447 must be substantial enough (e.g., exceed a threshold difference value, exceed a threshold percentage difference) rather than an absolute or literal difference. The difference may be based on or include one or more of any of a number of factors or variables. For example, the difference may be based on or include a characterization of water saturation.

The determination may be made by a controller 404 (or the baseline determination module 541 thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, the determination may be made by a user 451. The determination may be made at the surface (e.g., surface 108, surface 208). If there is a difference between the baseline for the parameters associated with the results of the tests on the samples 447 and the parameters associated with the results of the tests on the additional samples 447, then the process proceeds to step 774. If there is not a difference between the baseline for the parameters associated with the results of the tests on the samples 447 and the parameters associated with the results of the tests on the additional samples 447, then the process reverts to step 784.

In step 774, the baseline for at least one of the wells 420 is adjusted. Some or all of a baseline may be adjusted by a controller 404 (or the baseline determination module 541 thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, some or all of the process of adjusting the baseline for the parameters associated with the results of testing the samples 447 from the well 420 may be controlled by a user 451. The baseline for the parameters associated with the results of testing the samples 447 of the well 420 may be adjusted based on raw measurements made by sensor devices 460, adjusted measurements made by sensor devices 460, outputs of algorithms 533 (e.g., models) using measurements made by sensor devices 460 as inputs, some other information associated with measurements made by sensor devices 460, or any suitable combination thereof.

In some cases, adjusting the baseline for the parameters associated with the results of testing the samples 447 from a well 420 may include adjusting strategies and forecasts, as discussed above with respect to step 783, that may be used in one or more steps below. Chemistry calculations based on the results adjusted in this step 774 may be performed by a controller 404 (including portions thereof). In addition to modeling, lab testing and/or other evaluation methods, using the analytic system 450, may be used to evaluate the baseline for the parameters associated with the results of testing the samples 447 that was adjusted to determine if other adjustments to the baseline and/or other aspects (e.g., algorithms 533) of the well 420 need to be made. Adjusting the baseline for the parameters associated with the results of testing the samples 447 from the well 420 may be performed at the surface (e.g., surface 108, surface 208). The baseline for the parameters associated with the results of testing the samples 447 of the well 420 may be adjusted continuously over an extended period of time or on a discrete basis. If applicable, the baseline for the parameters associated with the results of testing the samples 447 of the well 420 may be adjusted based on historical data, other present data, and/or forecasts. When step 774 is complete, the process reverts to step 784.

In step 776, samples 447 for multiple wells 420 is obtained. The samples 447 may be obtained from all wells 420 of a pad or only select wells 420 of the pad. The samples 447 obtained at this point in time is during a field operation and is sometimes referred to herein as second samples or subsequent samples. The samples 447 may be extracted from a wellbore 420 during a part of the field operation of step 784. The samples 447 may be obtained at the surface (e.g., surface 108, surface 208) using field equipment 109, part of the conveyance system 488, and/or other equipment (e.g., pumps, compressors). Some or all of the process of obtaining the samples 447 from a well 420 may be controlled by a controller 404 (or a collecting component thereof) of the analytic system 450 using one or more protocols 532, one or more algorithms 533 (e.g., models), measurements of one or more sensor devices 460, input from a user 451 (which may include an associated user system 455), and/or any other source of information within the system 400. In addition, or in the alternative, some or all of the process of obtaining the samples 447 from a well 420 may be controlled by a user 451.

The samples 447 may be obtained from a well 420 continuously over an extended period of time or on an iterative basis. The rate (e.g., hourly, daily, weekly) of collecting and testing samples 447 during a field operation may vary (e.g., based on field operations, based on field conditions, based on business need, based on whether there is no significant change in the analyzed water chemistry) over time. Samples 447 from the same well 420 and/or different wells 420 may be obtained from different formation depths (e.g., as end members). This step 776, as well as step 777 and step 761, may apply to the some or all of the parent wells 420 and/or some or all of the child wells 420 that exist. One or more of the wells 420 during step 776, step 777, and step 761 may not shut in. To the extent that there is a well 420 that is shut in, step 776, step 777, and step 761 may not apply to that well 420 for the time that the shut in is effective.

In step 777, one or more parameters associated with the samples 447 is tested. Testing of the one or more parameters associated with the samples 447 may be conducted using one or more sensor devices 460 to measure the one or more parameters that are directly or indirectly associated with the samples 447. The parameters associated with the samples 447 may be tested at the surface (e.g., surface 108, surface 208). The parameters associated with the samples 447 that are tested may be the same as, or different than, the parameters that are tested in step 782 and/or step 789.

Some or all of the process of testing the parameters associated with the samples 447 may be controlled by a controller 404 (or a collecting component thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, some or all of the process of testing the parameters associated with the samples 447 may be controlled by a user 451. The parameters associated with the samples 447 may be tested continuously over an extended period of time or on a discrete basis.

In some cases, the samples 447 may be processed by the processing system 495 before being tested and/or after being tested. In the latter case, the parameters associated with the samples 447 may be retested after the samples 447 has been processed. The samples 447 may be processed multiple times and/or tested multiple times. The samples 447 may be processed for any of a number of purposes, including but not limited to removing cuttings and other unwanted solids, changing the pH, and adding chemicals (e.g., a fluid component 427). The samples 447 may be processed using any of a number of appropriate equipment of the processing system 495, including but not limited to heaters, chillers, mixers, filters, agitators, pumps, and centrifuges.

Some or all of the processing of the samples 447 using the processing system 495 may be controlled by a controller 404 (or a collecting component thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, some or all of the processing of the samples 447 using the processing system 495 may be controlled by a user 451. The samples 447 may be processed using the processing system 495 continuously over an extended period of time or on a discrete basis.

In step 778, a determination is made as to whether there is a difference between the baseline for parameters associated with the samples 447 and the parameters associated with the results of the tests on the second or subsequent samples 447 for the well 420 from step 777. In certain example embodiments, the difference between the baseline of the parameters associated with the results of the tests on the first or initial samples 447 and the parameters associated with the results of the tests on the second or subsequent samples 447 must be substantial enough (e.g., exceed a threshold difference value, exceed a threshold percentage difference) rather than an absolute or literal difference.

The determination may be made by a controller 404 (or the baseline determination module 541 and/or the field operation evaluation module 543 thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, the determination may be made by a user 451. The determination may be made at the surface (e.g., surface 108, surface 208). If there is a difference between the baseline of the parameters associated with the results of the tests on the first or initial samples 447 and the parameters associated with the results of the tests on the second or subsequent samples 447, then the process proceeds to step 779. If there is not a difference between the baseline of the parameters associated with the results of the tests on the first or initial samples 447 and the parameters associated with the results of the tests on the second or subsequent samples 447, then the process reverts to step 761.

In step 779, a determination is made as to whether the field operation is complete. The determination may be made by a controller 404 (or the field operation evaluation module 543 thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, the determination may be made by a user 451. The determination may be made at the surface (e.g., surface 108, surface 208). If the field operation is complete, then the process proceeds to step 763. If the field operation is not complete, then the process reverts to step 762.

In step 761, the forecasting model and/or the baseline for the well 420 is adjusted. Some or all of the baseline and/or the forecasting model may be adjusted by a controller 404 (or the baseline determination module 541 and/or the field operation evaluation module 543 thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, some or all of the process of adjusting the baseline and/or the forecasting model for the well 420 may be controlled by a user 451. The baseline and/or the forecasting model for the well 420 may be adjusted based on raw measurements made by sensor devices 460, adjusted measurements made by sensor devices 460, outputs of algorithms 533 (e.g., models) using measurements made by sensor devices 460 as inputs, some other information associated with measurements made by sensor devices 460, or any suitable combination thereof.

In some cases, adjusting the baseline and/or the forecasting model for the well 420 may include adjusting strategies and forecasts, as discussed above with respect to step 783. Chemistry calculations based on the results adjusted in this step 761 may be performed by a controller 404 (including portions thereof). In addition to modeling, lab testing and/or other evaluation methods, using the analytic system 450, may be used to evaluate the baseline and/or the forecasting model for the well 420 that was adjusted to determine if other adjustments to the baseline, the forecasting model, and/or other aspects (e.g., other algorithms 533) of the well 420 need to be made. Adjusting the baseline and/or the forecasting model for the well 420 may be performed at the surface (e.g., surface 108, surface 208). The baseline and/or the forecasting model for the well 420 may be adjusted continuously over an extended period of time or on a discrete basis. If applicable, the baseline and/or the forecasting model for the well 420 may be adjusted based on historical data, other present data, and/or forecasts. When step 761 is complete, the process proceeds to step 762.

In step 762, a determination is made as to whether samples 447 continue to be tested. Such a determination may be based on whether any of a number of factors, including but not limited to whether another field operation will be preferred on the same and/or a different well 420, whether the status of a well 420 changes (e.g., from shut-in to not shut-in), the amount of time that has passed since the field operation ended, and the amount of change in the current test results relative to the baseline for the samples 447 of the well 420. The determination may be made by a controller 404 (or the recommendation module 542 thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, the determination may be made by a user 451. The determination may be made at the surface (e.g., surface 108, surface 208). If samples 447 continue to be tested, then the process reverts to step 763. If samples 447 do not continue to be tested, then the process proceeds to the END step.

In step 763, samples 447 for one or multiple wells 420 are obtained. The samples 447 may be obtained from all wells 420 of a pad or only one or more select wells 420 of the pad. The samples 447 obtained at this point in time is after the field operation has ended and is sometimes referred to herein as third samples or further subsequent samples. The samples 447 may be extracted from a wellbore 420 during a part of a field operation. The samples 447 may be obtained at the surface (e.g., surface 108, surface 208) using field equipment 109, part of the conveyance system 488, and/or other equipment (e.g., pumps, compressors). Some or all of the process of obtaining the samples 447 from a well 420 may be controlled by a controller 404 (or a collecting component thereof) of the analytic system 450 using one or more protocols 532, one or more algorithms 533 (e.g., models), measurements of one or more sensor devices 460, input from a user 451 (which may include an associated user system 455), and/or any other source of information within the system 400. In addition, or in the alternative, some or all of the process of obtaining the samples 447 from a well 420 may be controlled by a user 451.

The samples 447 may be obtained from a well 420 continuously over an extended period of time or on an iterative basis. The rate (e.g., daily, weekly, monthly) of collecting and testing samples 447 may vary (e.g., based on field operations, based on field conditions, based on business need, based on whether there is no significant change in the analyzed water chemistry) over time. To the extent that a field operation has just been completed, the samples 447 obtained from one or more of the various wells 420 may be done so as soon after completion of the field operation as possible in certain example embodiments. This step 763, as well as step 764 and step 767, may apply to the some or all of the parent wells 420 and/or some or all of the child wells 420 that exist. One or more of the wells 420 during step 763, step 764, and step 767 may not shut in. To the extent that there is a well 420 that is shut in, step 763, step 764, and step 767 may not apply to that well 420 for the time that the shut in is effective.

Samples 447 from the same well 420 and/or different wells 420 may be obtained from different formation depths (e.g., as end members). If a well 420 is shut in during the field operation that just concluded, one or more samples 447 from that well 420 should be obtained and tested soon (e.g., within a few hours, within a day, within a few days) after the well is no longer shut in and returned to production (sometimes called RTP). Similarly, if the field operation that just concluded was performed on one or more particular wells 420, then one or more samples 447 from those wells 420 may be obtained and tested soon (e.g., within a few hours, within a day, within a few days) after the well is put on production.

In step 764, one or more parameters associated with the samples 447 are tested. Testing of the one or more parameters associated with the samples 447 may be conducted using one or more sensor devices 460 to measure the one or more parameters that are directly or indirectly associated with the samples 447. The parameters associated with the samples 447 may be tested at the surface (e.g., surface 108, surface 208). The parameters associated with the samples 447 that are tested may be the same as, or different than, the parameters that are tested in step 782, step 789, and/or step 777.

Some or all of the process of testing the parameters associated with the samples 447 may be controlled by a controller 404 (or a collecting component thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, some or all of the process of testing the parameters associated with the samples 447 may be controlled by a user 451. The parameters associated with the samples 447 may be tested continuously over an extended period of time or on a discrete basis.

In some cases, the samples 447 may be processed by the processing system 495 before being tested and/or after being tested. In the latter case, the parameters associated with the samples 447 may be retested after the samples 447 has been processed. The samples 447 may be processed multiple times and/or tested multiple times. The samples 447 may be processed for any of a number of purposes, including but not limited to removing cuttings and other unwanted solids, changing the pH, and adding chemicals (e.g., a fluid component 427). The samples 447 may be processed using any of a number of appropriate equipment of the processing system 495, including but not limited to heaters, chillers, mixers, filters, agitators, pumps, and centrifuges.

Some or all of the processing of the samples 447 using the processing system 495 may be controlled by a controller 404 (or a collecting component thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, some or all of the processing of the samples 447 using the processing system 495 may be controlled by a user 451. The samples 447 may be processed using the processing system 495 continuously over an extended period of time or on a discrete basis.

In step 766, a determination is made as to whether there is a difference between the baseline of the parameters associated with the results of the tests on prior samples 447 and the parameters associated with the results of the tests on the most recent samples 447 for the well 420 from step 764. In some cases, the baseline may be adjusted (as in step 767 below) relative to the initial baseline (as in step 783). In certain example embodiments, the difference between the baseline of the parameters associated with the results of the tests on prior samples 447 and the parameters associated with the results of the tests on the most recent samples 447 must be substantial enough (e.g., exceed a threshold difference value, exceed a threshold percentage difference) rather than an absolute or literal difference.

The determination may be made by a controller 404 (or the baseline determination module 541 and/or the field operation evaluation module 543 thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, the determination may be made by a user 451. The determination may be made at the surface (e.g., surface 108, surface 208). If there is a difference between the baseline of the parameters associated with the results of the tests on prior samples 447 and the parameters associated with the results of the tests on the most recent samples 447, then the process proceeds to step 767. If there is not a difference between the baseline of the parameters associated with the results of the tests on prior samples 447 and the parameters associated with the results of the tests on the most recent samples 447, then the process reverts to step 762.

In step 767, the forecasting model and/or the baseline for the well 420 is adjusted. Some or all of the baseline and/or the forecasting model may be adjusted by a controller 404 (or the baseline determination module 541 and/or the field operation evaluation module 543 thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, some or all of the process of adjusting the baseline and/or the forecasting model for the well 420 may be controlled by a user 451. The baseline and/or the forecasting model for the well 420 may be adjusted based on raw measurements made by sensor devices 460, adjusted measurements made by sensor devices 460, outputs of algorithms 533 (e.g., models) using measurements made by sensor devices 460 as inputs, some other information associated with measurements made by sensor devices 460, or any suitable combination thereof.

In some cases, adjusting the baseline and/or the forecasting model for the well 420 may include adjusting strategies and forecasts, as discussed above with respect to step 783. Chemistry calculations based on the results adjusted in this step 767 may be performed by a controller 404 (including portions thereof). In addition to modeling, lab testing and/or other evaluation methods, using the analytic system 450, may be used to evaluate the baseline and/or the forecasting model for the well 420 that was adjusted to determine if other adjustments to the baseline, the forecasting model, and/or other aspects (e.g., other algorithms 533) of the well 420 need to be made. Adjusting the baseline and/or the forecasting model for the well 420 may be performed at the surface (e.g., surface 108, surface 208). The baseline and/or the forecasting model for the well 420 may be adjusted continuously over an extended period of time or on a discrete basis. If applicable, the baseline and/or the forecasting model for the well 420 may be adjusted based on historical data, other present data, and/or forecasts.

In some cases, one or more controllers 404 of the analytic system 450 may be used to control or facilitate control of the implementation of the output of any of the algorithms 533 (e.g., models) of the analytic system 450. For example, when the output of an algorithm 533 indicates a particular amount and type of chemical component or compound to add to a fluid 437 for use in one or more wells 420 during a current or planned field operation, one or more of the controllers 404 of the analytic system 450 may obtain the amount and type of chemical component or compound from one or more of the fluid component sources 428, mix the chemical component or compound into a fluid 437 using the processing system 495, and deliver the resulting fluid 437 to one or more of the wells 420 using the conveyance system 488.

In step 768, a determination is made as to whether an additional field operation has started. The additional field operation may be directly applied to one or more of the wells 420. The effects of the field operation may affect those same wells 420, as well as one or more other wells 420 in the subterranean formation (e.g., subterranean formation 110, subterranean formation 210). The determination may be made by a controller 404 (or the field operation evaluation module 543 thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, the determination may be made by a user 451. The determination may be made at the surface (e.g., surface 108, surface 208). If a field operation has started, then the process proceeds to step 776. If a field operation has not started, then the process reverts to step 762.

Figure 8:
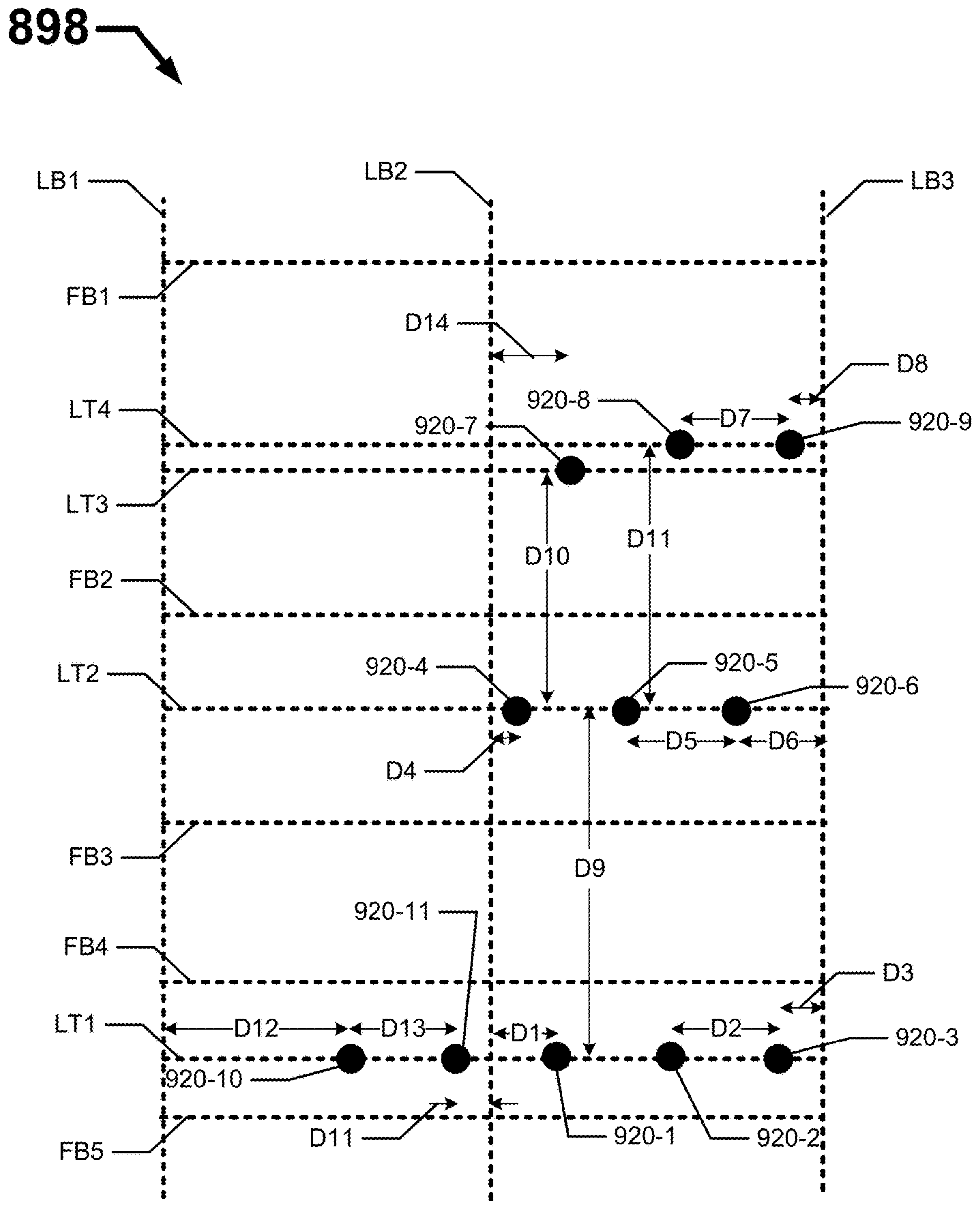
FIG. 8 shows a gun barrel diagram of multiple wells in a subterranean formation for use with certain example embodiments.
Figure 9:
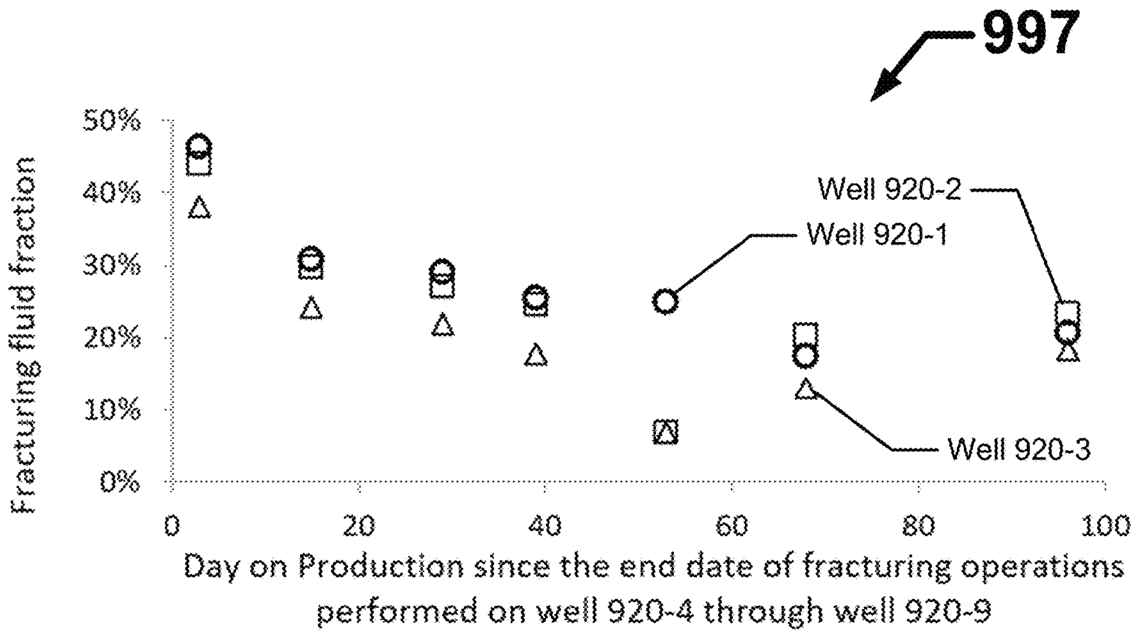
FIG. 9 shows a graph of a ratio of fracturing fluid in produced water samples for the parent wells according to certain example embodiments.
Figure 10:
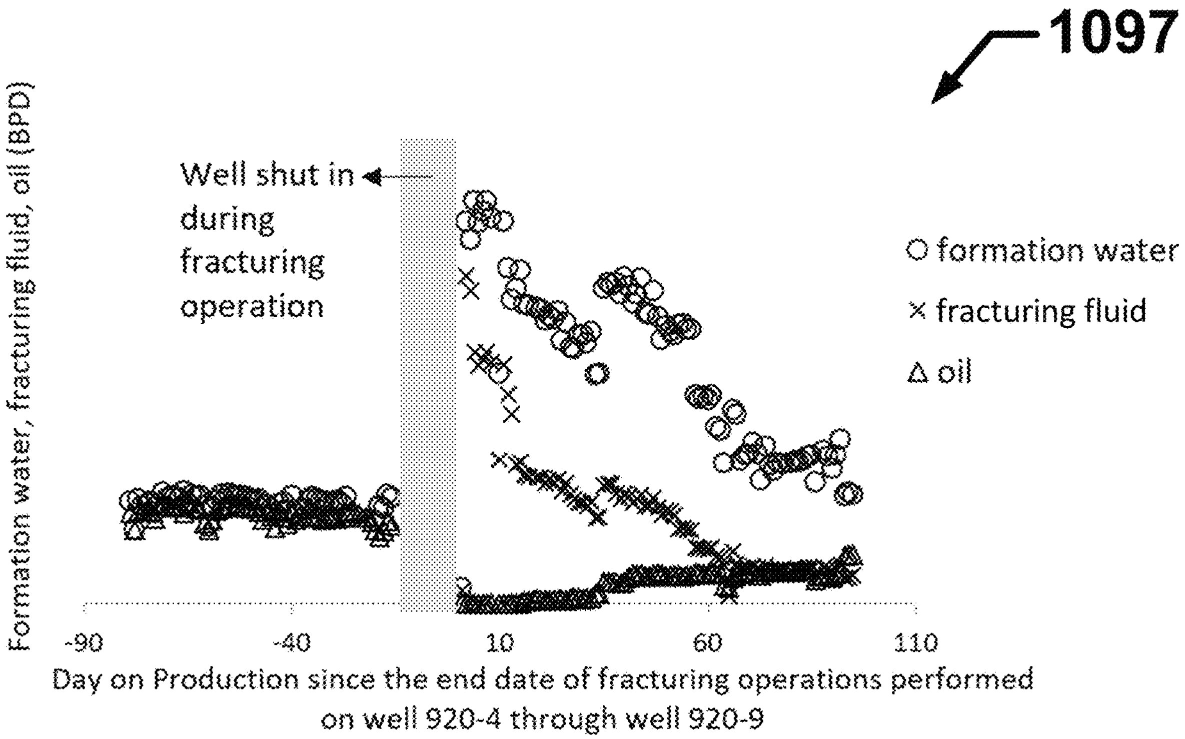
FIG. 10 shows a graph of production rates of various fluids over time for a well according to certain example embodiments.
Figure 11:
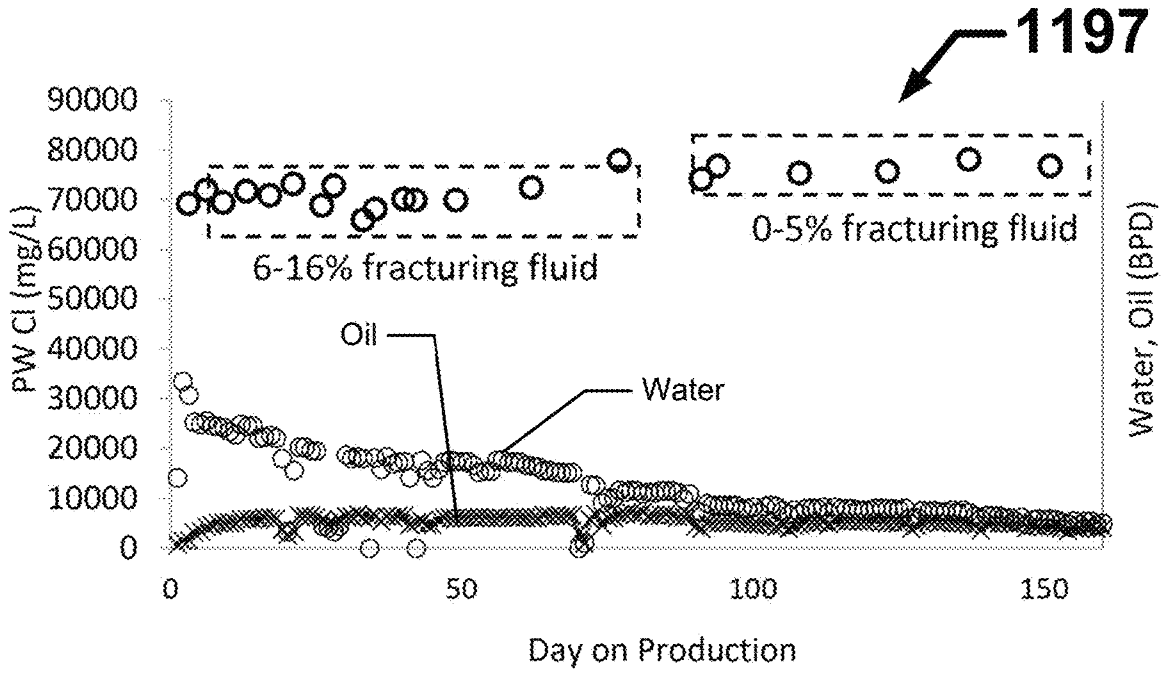
FIG. 11 shows a graph of various collection elements of a well while on production according to certain example embodiments.
Figure 12:
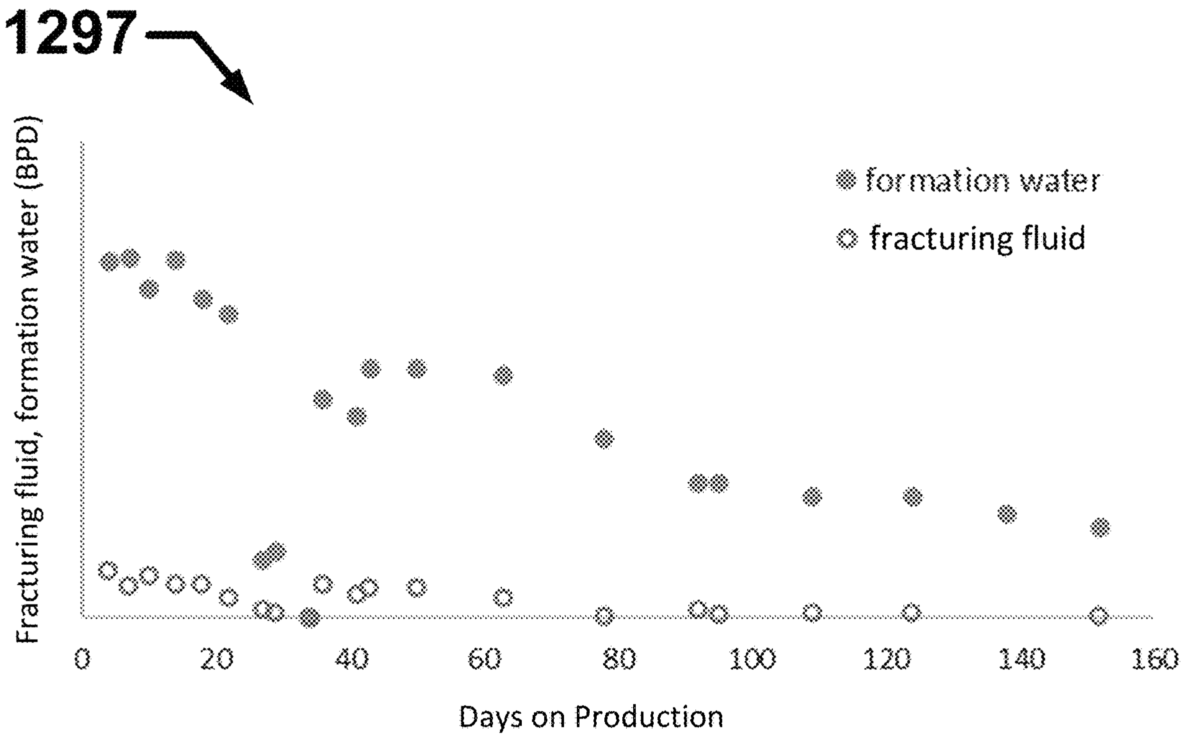
FIG. 12 shows a graph of the production rate of fracturing fluid and formation water for a well while on production according to certain example embodiments.

An example of the use of example embodiments on 11 wells 920 in the context of hydraulic fracturing is discussed below with respect to FIGS. 8 through 24. FIG. 8 shows a gun barrel diagram 898 of multiple wells in a subterranean formation for use with certain example embodiments. FIG. 9 shows a graph 997 of a ratio of fracturing fluid (sometimes referred to as frac water herein) in produced water (sometimes referred to as PW herein) samples for the parent wells 920-1, 920-2, 920-3 according to certain example embodiments. FIG. 10 shows a graph 1097 of production rates of various fluids (in this case, formation water, fracturing fluid, and oil) over time for well 920-1 according to certain example embodiments. FIG. 11 shows a graph 1197 of various collection elements of well 920-4 while on production according to certain example embodiments. FIG. 12 shows a graph 1297 of the production rate of fracturing fluid and formation water for well 920-4 while on production according to certain example embodiments.

Figure 13:
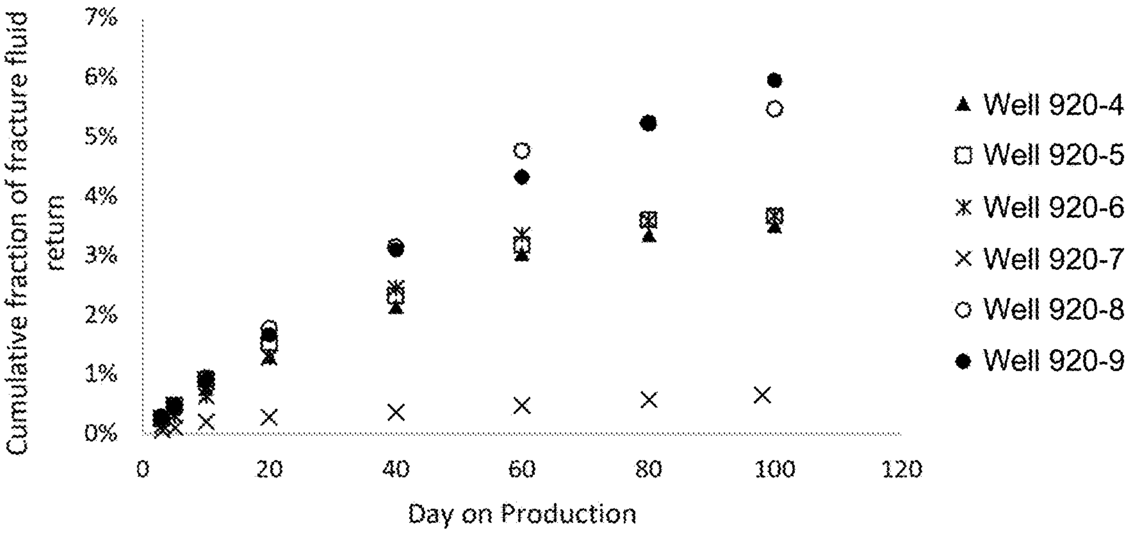
FIG. 13 shows a graph of the ratio of fracturing fluid in water for the child wells while on production according to certain example embodiments.
Figure 14:
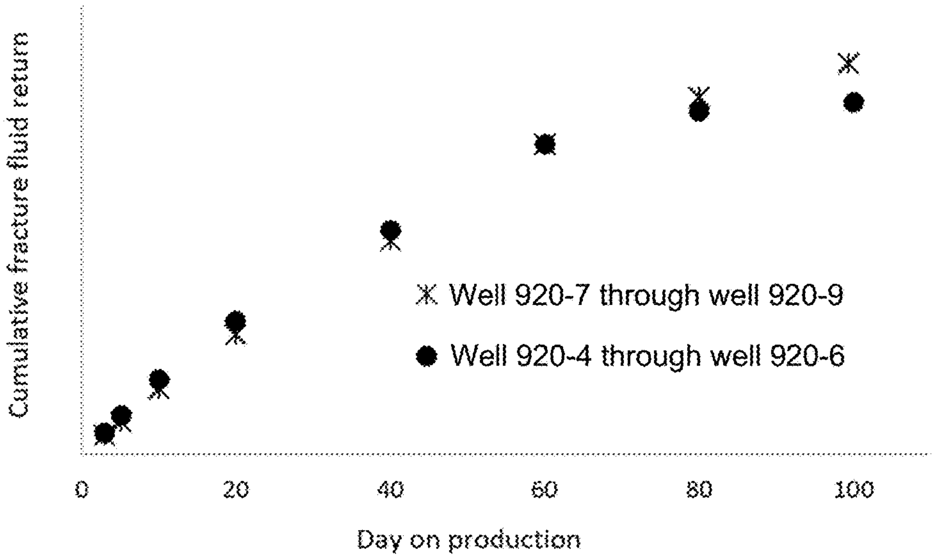
FIG. 14 shows a graph of fracturing fluid in water samples per group of child wells while on production according to certain example embodiments.
Figure 15:
FIG. 15 shows a graph of formation water samples for the child wells while on production according to certain example embodiments.
Figure 16:
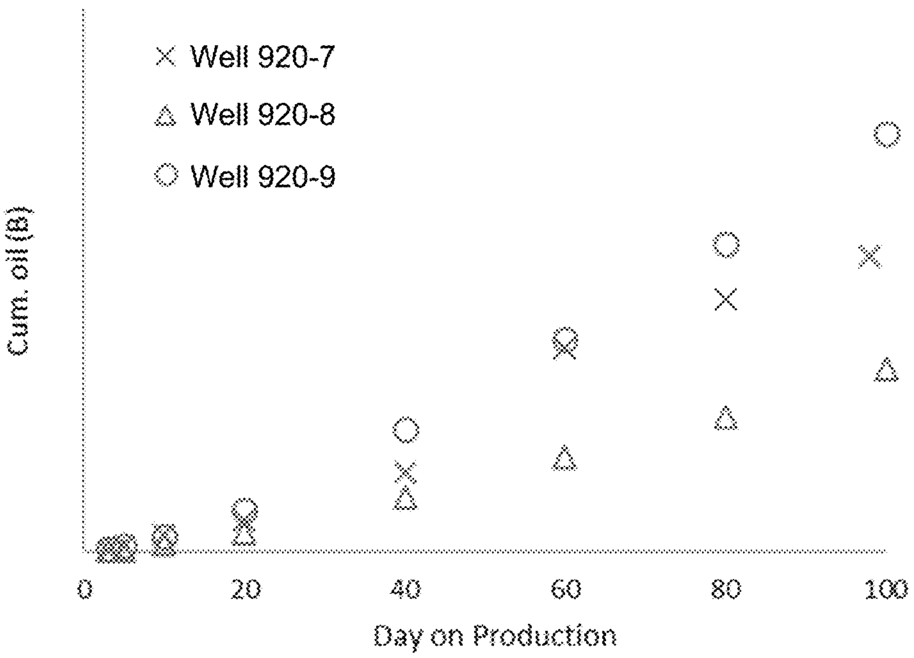
FIG. 16 shows a graph of oil production for the child wells while on production according to certain example embodiments.
Figure 17:
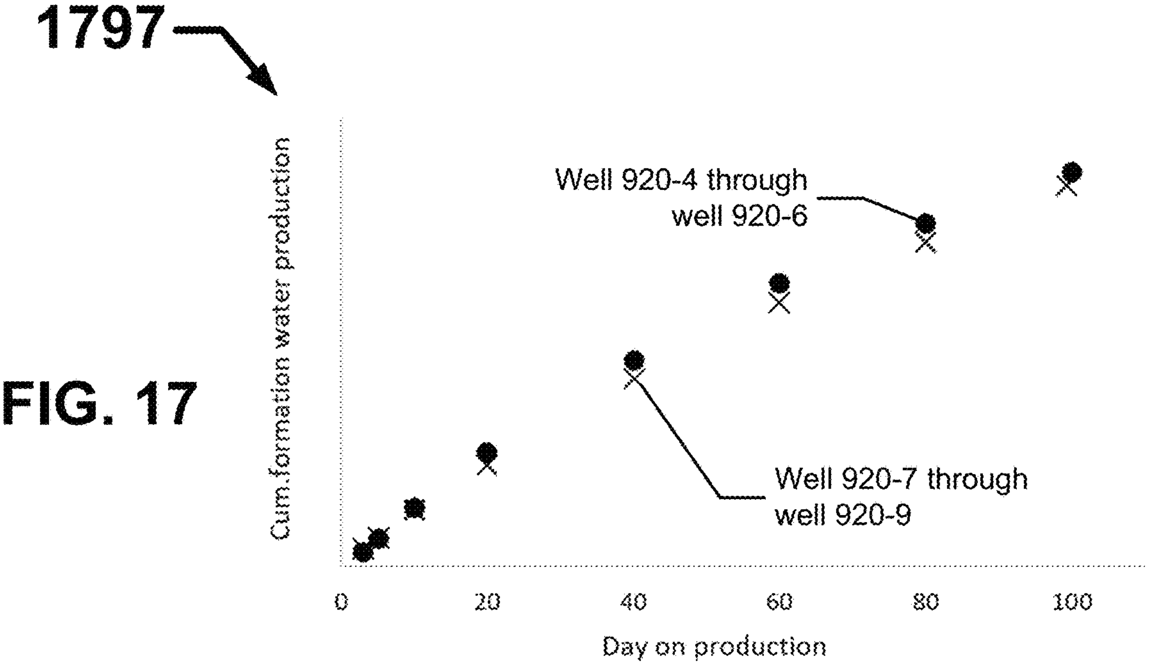
FIG. 17 shows a graph of formation water for groups of the child wells while on production according to certain example embodiments.
Figure 18:
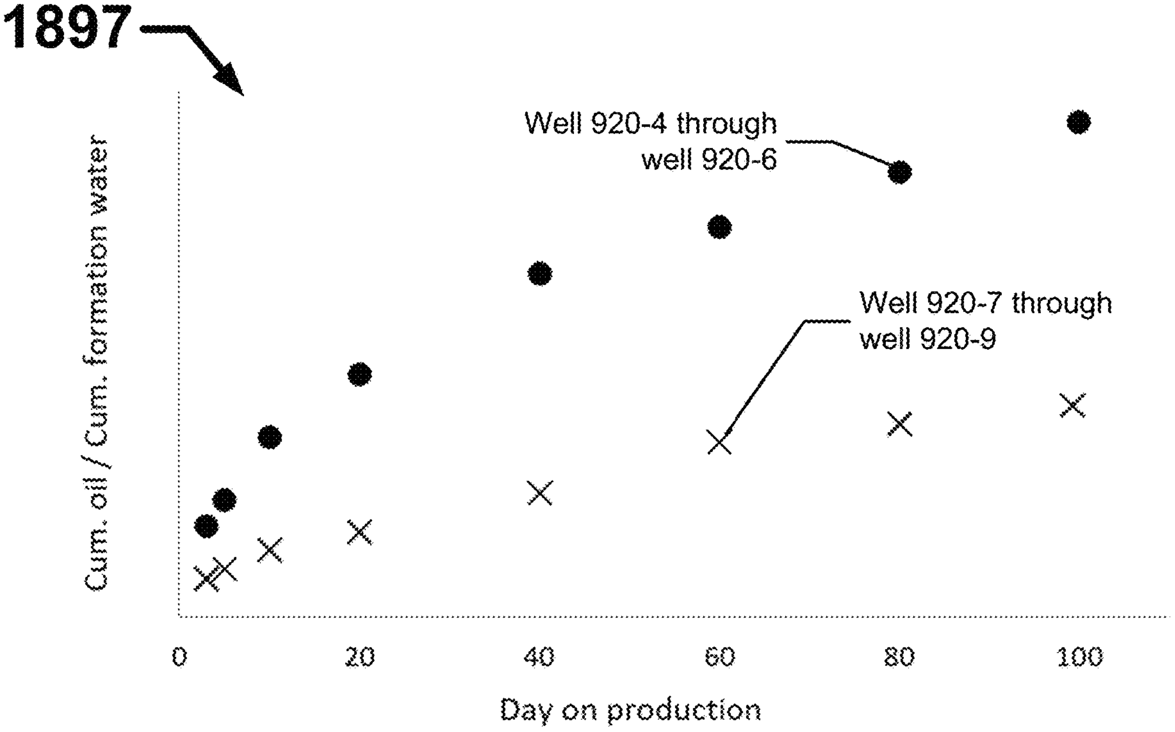
FIG. 18 shows a graph of oil production for groups of the child wells while on production according to certain example embodiments.

FIG. 13 shows a graph 1397 of the ratio of fracturing fluid in water samples for the child wells 920-4, 920-5, 920-6, 920-7, 920-8, and 920-9 while on production according to certain example embodiments. FIG. 14 shows a graph 1497 of fracturing fluid in water samples per group of child wells 920-7 through 920-9 and 920-4 through 920-6 while on production according to certain example embodiments. FIG. 15 shows a graph 1597 of formation water for the child wells 920-7, 920-8, and 920-9 while on production according to certain example embodiments. FIG. 16 shows a graph 1697 of oil production for the child wells 920-7, 920-8, and 920-9 while on production according to certain example embodiments. FIG. 17 shows a graph 1797 of formation water for groups of the child wells 920-7 through 920-9 and 920-4 through 920-6 while on production according to certain example embodiments. FIG. 18 shows a graph 1897 of oil production for groups of the child wells 920-7 through 920-9 and 920-4 through 920-6 while on production according to certain example embodiments.

Figure 19:
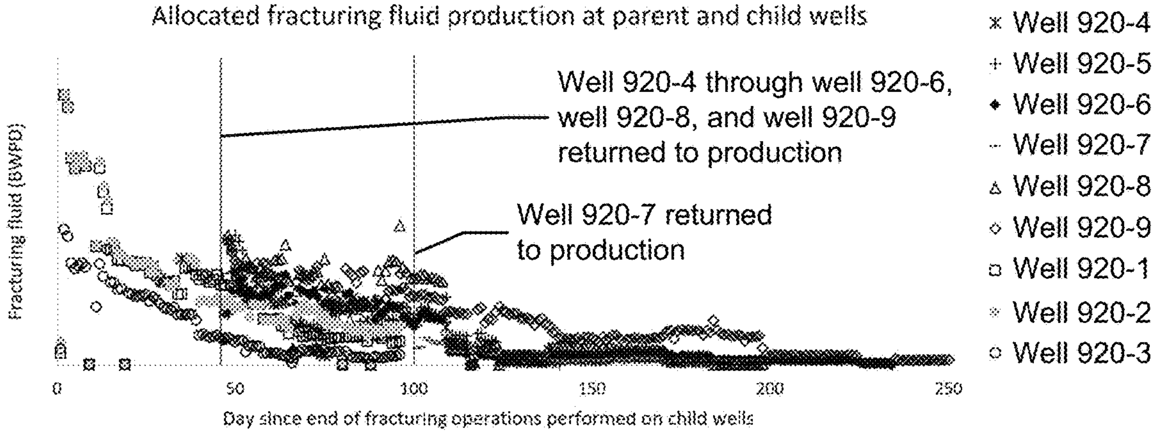
FIG. 19 shows a graph of fracturing fluid production for one or more wells over time according to certain example embodiments.
Figure 20:
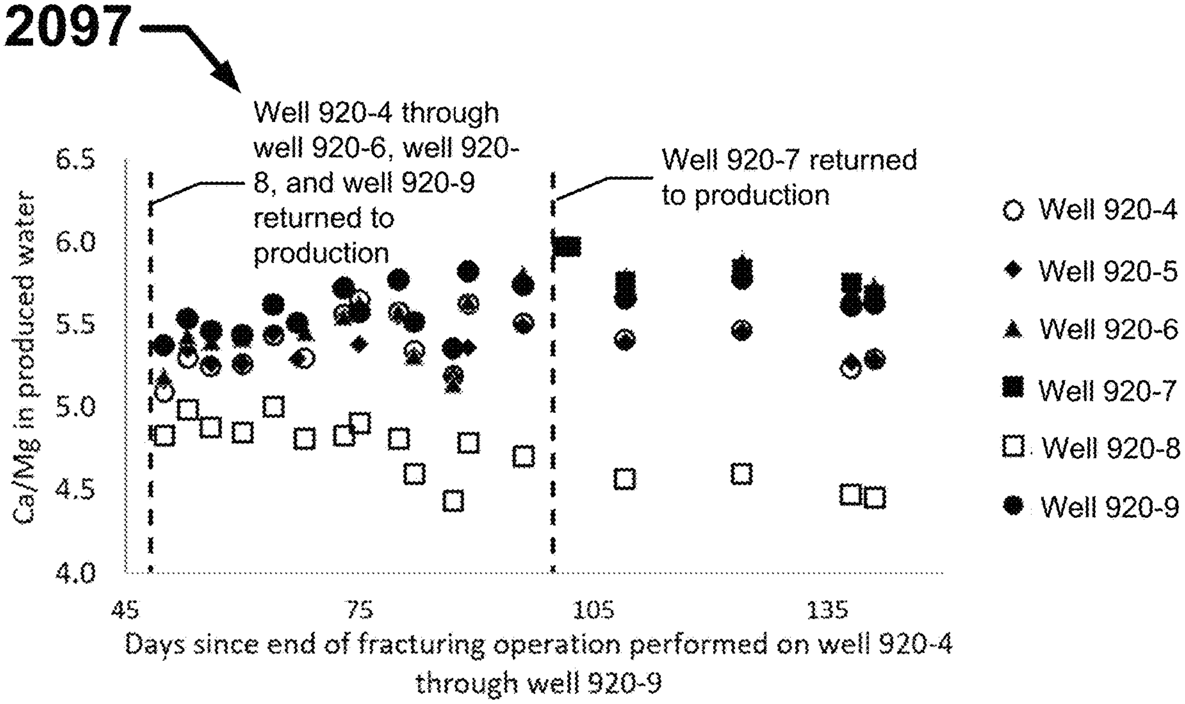
FIG. 20 shows a graph of certain ions in produced water of various wells according to certain example embodiments.
Figure 21:
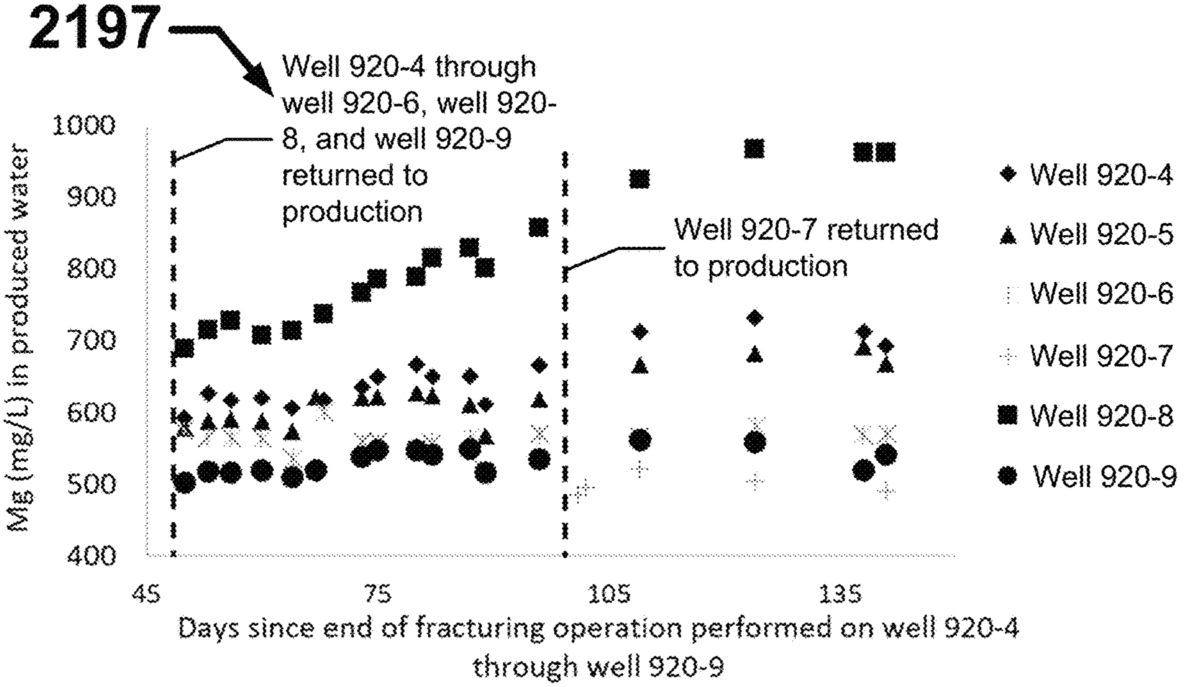
FIG. 21 shows a graph of Mg in produced water for various wells according to certain example embodiments.
Figure 22:
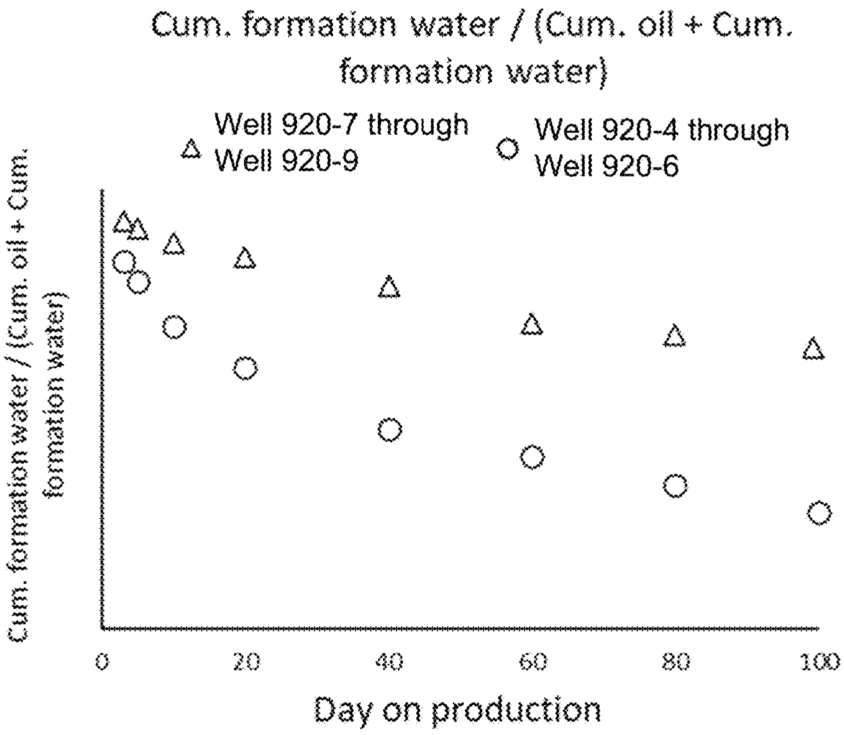
FIG. 22 shows a graph of ratios of formation water for various child wells while on production according to certain example embodiments.
Figure 23:
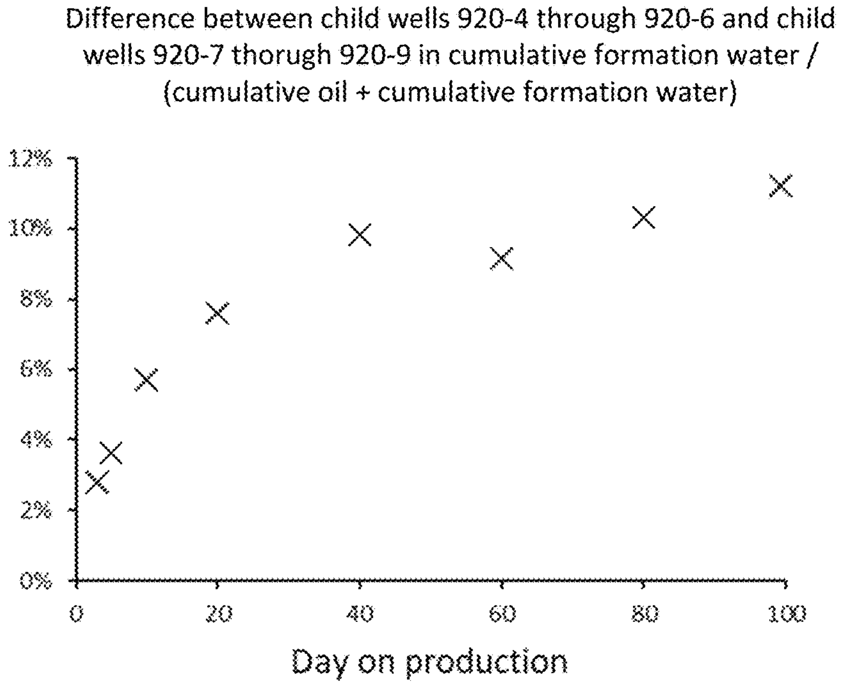
FIG. 23 shows a graph of ratios of differences in formation water between various child wells while on production according to certain example embodiments.
Figure 24:
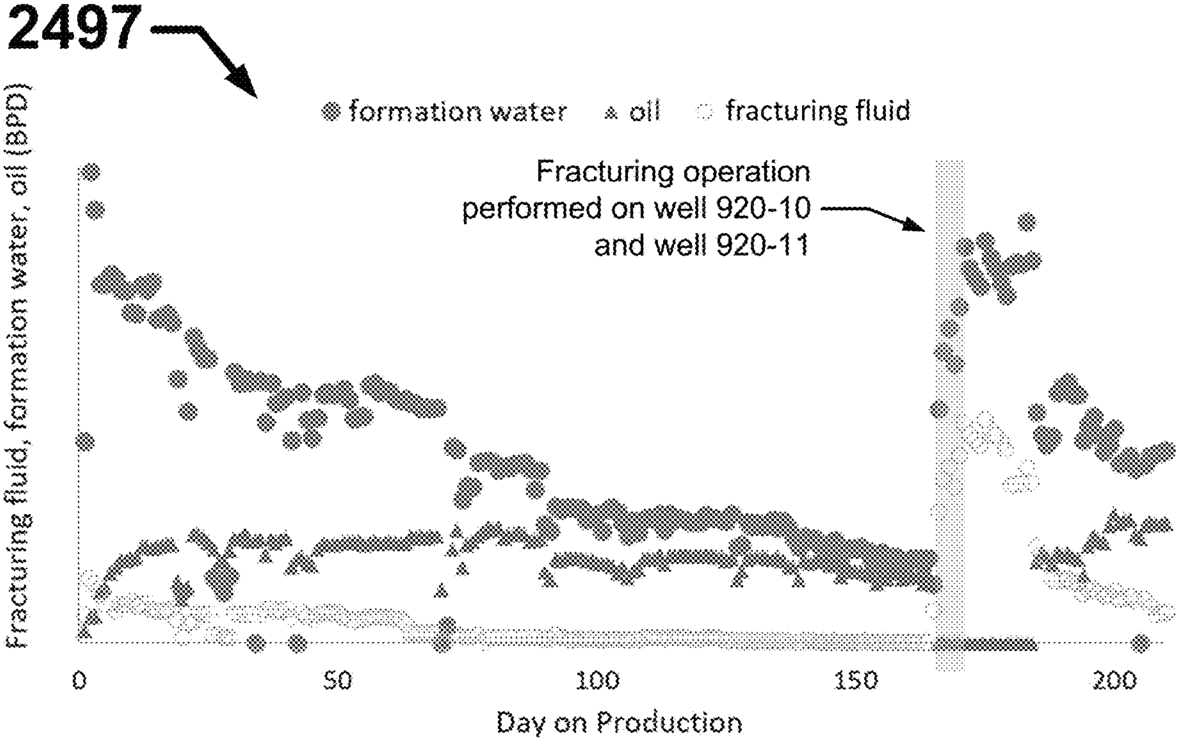
FIG. 24 shows a graph of production rates of various fluids in one of the wells according to certain example embodiments.

FIG. 19 shows a graph 1997 of fracturing fluid production for multiple wells 920 over time according to certain example embodiments. FIG. 20 shows a graph 2097 of certain ions in produced water of various wells 920 according to certain example embodiments. FIG. 21 shows a graph 2197 of Mg in produced water for various wells 920 according to certain example embodiments. FIG. 22 shows a graph 2297 of ratios of formation water for various child wells 920-7 through 920-9 and 920-4 through 920-6 while on production according to certain example embodiments. FIG. 23 shows a graph 2397 of ratios of differences in formation water between various child wells 920 while on production according to certain example embodiments. In other words, FIG. 23 and FIG. 24 illustrate an example approach that may be used to estimate a difference in water saturation between target formations. FIG. 24 shows a graph 2497 of production rates of various fluids in one of the wells according to certain example embodiments.

Referring to the description of the prior figures, the gun barrel diagram 898 of FIG. 8 shows a total of 11 horizontal wells 920 viewed as a cross section slice through the lateral portion of each drilled well 920. Specifically, the gun barrel diagram 898 illustrates the subsurface vertical and lateral spacing of the horizontal sections of the wells 920 within a development field. Listed in order of drilling/completion are well 920-1, well 920-2, well 920-3, well 920-4, well 920-5, well 920-6, well 920-7, well 920-8, well 920-9, well 920-10, and well 920-11.

Well 920-1, well 920-2, and well 920-3 are considered as a group (sometimes referred to in this example as parent wells) because of their substantially similar depth. Similarly, well 920-4, well 920-5, and well 920-6 are considered as a group because of their substantially similar depth. Further, well 920-7, well 920-8, and well 920-9 are considered as a group because of their substantially similar depth. Well 920-4 through well 920-9 are sometimes referred to in this example as child wells. Finally, well 920-10 and well 920-11, which are of approximately the same depth as well 920-1, well 920-2, and well 920-3, are considered as a separate group because they were drilled/completed at a later point in time.

Line LT1 in the gun barrel diagram 898 represents the landing target depth for well 920-1, well 920-2, well 920-3, well 920-10, and well 920-11. Line LT2 represents the landing target depth for well 920-4, well 920-5, well 920-6. Line LT3 represents the landing target depth for well 920-7. Line LT4, which is just above line LT3, represents the landing target depth for well 920-8 and well 920-9. Line LT1 and line LT2 are separated from each other by a distance D9 (e.g., 510 feet). Line LT2 and line LT3 are separated from each other by a distance D10 (e.g., 330 feet). Line LT2 and line LT4 are separated from each other by a distance D11 (e.g., 370 feet).

Line FB1, line FB2, line FB3, line FB4, and line FB5 (all substantially horizontal lines) in the gun barrel diagram 898 represent a formation boundary. Well 920-1, well 920-2, well 920-3, well 920-10, and well 920-11 are located between FB4 and FB5. Well 920-4, well 920-5, well 920-6 are located between FB2 and FB3. Well 920-7, well 920-8, and well 920-9 are located between FB1 and FB2. Line LB1, line LB2, and line LB3 (all vertical lines) in the gun barrel diagram 898 represent land boundaries.

Well 920-1 is located a distance D1 (e.g., 630 feet) from line LB2 and is positioned between line LB2 and line LB3. Well 920-2 is located a distance D2 (e.g., 840 feet) from well 920-3 and is positioned between line LB2 and line LB3. Well 920-3 is located a distance D3 (e.g., 330 feet) from line LB3 and is positioned between line LB2 and line LB3. Well 920-4 is located a distance D4 (e.g., 207 feet) from line LB2 and is positioned between line LB2 and line LB3. Well 920-5 is located a distance D5 (e.g., 840 feet) from well 920-6 and is positioned between line LB2 and line LB3. Well 920-6 is located a distance D6 (e.g., 750 feet) from line LB3 and is positioned between line LB2 and line LB3.

Well 920-7 is located a distance D14 (e.g., 770 feet) from line LB2 and is positioned between line LB2 and line LB3. Well 920-8 is located a distance D7 (e.g., 840 feet) from well 920-9 and is positioned between line LB2 and line LB3. Well 920-9 is located a distance D8 (e.g., 330 feet) from line LB3 and is positioned between line LB2 and line LB3. Well 920-10 is located a distance D12 (e.g., 1513 feet) from line LB1 and is positioned between line LB and line LB2. Well 920-11 is located a distance D13 (e.g., 840 feet) from well 920-10 and a distance D11 (e.g., 315 feet) from line LB2 and is positioned between line LB2 and line LB3.

Well 920-1, well 920-2, and well 920-3 were put on production earlier (e.g., approximately 2.5 years) than when well 920-4, well 920-5, well 920-6, well 920-7, well 920-8, and well 920-9 were put on production. In some cases, well 920-4, well 920-5, well 920-6, well 920-7, well 920-8, and well 920-9 have substantially the same start and end dates for fracturing operations on those wells 920. Further, in this example, well 920-8 was put on production earlier (e.g., by 54 days) than when well 920-4, well 920-5, well 920-6, well 920-7, and well 920-9 were put on production. Well 920-10 and well 920-11 underwent a fracturing operation later (e.g., about 5 months) after well 920-4, well 920-5, well 920-6, well 920-7, and well 920-9 were put on production.

Produced water is collected from samples (e.g., samples 447) over time at the wellhead for all wells 920. Prior to the fracturing of child well 920-4 through well 920-9, produced water geochemistry surveillance (i.e., collection and testing of samples of the water, as discussed above) is utilized to extrapolate formation water data for parent well 920-1 through parent well 920-3. In this example, well 920-1, well 920-2, and well 920-3 are shut in during the fracturing operations and subsequently (e.g., the next day) put on production (sometimes referred to as POP) the day after hydraulic fracturing of well 920-4 through well 920-9 is completed. Produced water samples are periodically collected and tested for well 920-1, well 920-2, and well 920-3 after those wells 920 are returned to production.

The collection and testing rate of samples of the water from each well 920 may vary. For example, the rate of collecting and testing samples of the water from well 920-4 through well 920-9 may be more frequent (e.g., 2 samples/week) for some initial period (e.g., the first month after those wells 920 are put on production), then slightly less frequent (e.g., 1 sample per week) for some period of time (e.g., one month) after the initial period, then even less frequent (e.g., 1 sample every 2 weeks) for some subsequent period of time (e.g., four months) after the prior period, then even less frequent (e.g., 1 sample every month) for some subsequent period of time (e.g., six months) after the prior period, and then then even less frequent (e.g., 1 sample every quarter) for some subsequent period of time (e.g., 12 months) after the prior period. The sampling plan for a particular well 920 may be adjusted based on well status and field operation conditions.

In addition to time-lapse sampling of water (e.g., produced water) from samples (e.g., samples 447) obtained from one or more of the wells 920, samples of water (e.g., water included in fracturing fluid, which is a form of a fluid 437) may also be collected for each of the wells 920 within some period of time (e.g., 1 day, 1 week, 1 month) prior to the start of the fracturing operation of one or more of the wells 920 (e.g., of child well 920-4 through child well 920-9). Concentrations of dissolved ions and/or other elements (e.g., Cl, Na, K, Ca, Mg, Sr) of all collected samples of water may be analyzed in lab within some period of time (e.g., 2 weeks) of the sampling date for one or more of the wells 920.

Table 1 below lists the water chemistry data of samples that includes the water (e.g., water in fracturing fluid, which is a form of a fluid 437) used for the completion of child well 920-4 through well 920-9 and two samples of water (e.g., produced water) from the parent well 920-1. At this point in time, well 920-1 has been put on production for over 2 years, and the composition of the water chemistry of the water has been stabilized prior to the simultaneous hydraulic fracturing operation of well 920-4 through well 920-9. The sample of the water collected on the day prior to the simultaneous fracturing operation of well 920-4 through well 920-9 is deemed as representative of formation water in the local landing zone of parent well 920-1.

TABLE 1

| Dissolved Ions | Fracturing Fluid For Well 920-4 Through Well 920-9 | Water Collected From Well 920-1 Within 24 Hours Prior To Fracturing Operation | Water Collected From Well 920-1 Within 3 Days of the End of Fracturing Operation |
|---|---|---|---|
| Cl (mg/L) | 1570 | 87326 | 47628 |
| $SO_4$ (mg/L) | 1054 | 810 | 994 |
| Na (mg/L) | 1415 | 41028 | 25425 |
| Ca (mg/L) | 75 | 6725 | 2175 |
| Mg (mg/L) | 56 | 1401 | 407 |
| Sr (mg/L) | 0 | 429 | 175 |
| K (mg/L) | 12.3 | 479 | 344 |
| Density (g/ml) | 1.003 | 1.096 | 1.077 |

Given the difference in water chemistry data between the fracturing fluid (frac water) and the formation water, water chemistry data may be used to calculate the fraction of fracturing fluid and formation water in samples (e.g., samples 447) of the water (e.g., produced water) from parent well 920-1 through parent well 920-3. As shown in Table 1, changes in the water chemistry composition of the water for well 920-1 occurred after the simultaneous fracturing operation of well 920-4 through well 920-9. Water chemistry data for the water shows that the sample of the water collected from well 920-1 on Day 3 after the end of the simultaneous fracturing operation of well 920-4 through well 920-9 was a mixture of fracturing fluid and formation water.

Water commingling and rock-water interaction at subsurface/fracture networks (e.g., fractures 101) may lead to scale precipitation and mineral dissolution/transformation and impact the concentrations of almost all ions except Cl in the water. Cl ion was deemed as a conservative parameter and used to calculate the fraction of fracturing fluid and formation water in the produced water obtained and test from the parent well 920-1 through parent well 920-3. The fractions (e.g., ratios) and production rate of fracturing fluid and formation water in the produced water may be calculated via the following equations (types of algorithms 533):

$$f_{frac} = \frac{C_{formation} - C}{C_{formation} - C_{frac}} \tag{1}$$

$$f_{formation} = \frac{C - C_{frac}}{C_{formation} - C_{frac}} \tag{2}$$

$$r_{frac} = r_{produced\ water} * f_{frac} \tag{3}$$

$$r_{formation} = r_{produced\ water} * f_{formation}, \tag{4}$$

where

C is the Cl concentration in the water, $C_{frac}$ is the Cl concentration in the water within the fracturing fluid, $C_{formation}$ is the Cl concentration in the formation water, $f_{frac}$ is the volume fraction of water within the fracturing fluid in the produced water, $f_{formation}$ is the volume fraction of formation water in produced water, r is the rate of production of the produced water, and $r_{frac}$ is the rate production of the fracturing fluid.

For all the wells 920 in this example, including both parent wells (well 920-1 through well 920-3) and child wells (well 920-4 through well 920-11), $C_{formation}$ is determined based on produced water chemistry surveillance over time. For most of child well 920-4 through child well 920-11 in this example, the produced water composition of the water became stabilized after about 3 months after those wells 920 were put on production if the well 920 was not impacted by a new fracturing operation and/or other field operations. The stabilized produced water Cl concentration may be used as $C_{formation}$.

For dates on which a sample of produced water for a well 920 is not collected, the volume fraction of fracturing fluid to produced water may be estimated to be the average of the calculated fractions of fracturing fluid of the closest sampling dates before and after those missed dates. For example, if samples of produced water is collected and fractions of fracturing fluid is calculated based on water chemistry data for Day 4 and Day 7, the estimated volume fraction of fracturing fluid for Day 5 and Day 6 may be the average of the calculated volume fractions of the fracturing fluid on Day 4 and Day 7 for that well 920.

Fracture-driven interaction (FDI) may result in fracturing fluid production in parent well 920-1 through parent well 920-3. The graph 997 of FIG. 9 shows the fraction of fracturing fluid relative to produced water in samples (e.g., samples 447) collected or otherwise obtained from parent well 920-1 through parent well 920-3 during the first 100 days after parent well 920-1 through parent well 920-3 are put on production, which started one day after the end date of the fracturing operation. The amount of fracturing fluid in the produced water of well 920-1 is about 46% on Day 3 and remains above 20% during the first 100 days after the end of the fracturing operation of child well 920-4 through child well 920-9. The amount of fracturing fluid in the produced water of well 920-2 in this example is lower than but very close to the amount of fracturing fluid in the produced water of well 920-1 during this period of time.

While the amount of fracturing fluid in the produced water of well 920-3 is shown in the graph 997 of FIG. 9 to be the lowest among these 3 wells 920, it is 38% on Day 3 and remains above 15% during the first 40 days since the end of the hydraulic fracturing operations. The graph 997 of FIG. 9 may indicate which well has principal fractures (e.g., fractures 101 that have proppant 112 lodged therein) as opposed to secondary fractures (e.g., fractures 101 that have little or no proppant 112 lodged therein). For example, if the fracturing fluid fraction of a well 920 is above a certain level (e.g., 25%, 40%) or within range of levels (e.g., 25% to 90%, 40% to 100%, 50% to 75%), then the analytic system 450 may conclude that the well 920 has a number of principal fractures that are likely to last for a longer duration (e.g., an extra 3 months, an extra 6 months, an extra year) relative to secondary fractures.

As a result, the well 920 that is identified as having principal fractures based on the fracturing fluid fraction may produce higher volumes of fluid and/or for a longer period of time relative to a well with secondary fractures. For example, the analytic system 450 may revise the forecasting model for well 920-1 and well 920-2 by extending an amount of days on production and/or increasing an amount of fluids produced for the well 920-1 and well 920-2 because the well 920-1 and the well 920-2 have a fracturing fluid fraction that exceeds 40% (or some other threshold value) or is within range of levels (e.g., 25% to 90%, 40% to 100%, 50% to 75%) when first tested after being returned to production. Conversely, of a well 920 has a fracturing fluid fraction that falls below some threshold value (e.g., 10%, 20%, 40%) or within range of levels (e.g., 0% to 40%, 4% to 30%, 10% to 20%), then the analytic system 450 may revise the forecasting model for that well 920 reducing an amount of days on production and/or decreasing an amount of fluids produced for the well 920.

Notably, the formation water produced at parent well 920-1 through parent well 920-3 after the fracturing operation may also include formation water from landing targets of the child wells 920 (e.g., well 920-4 through well 920-9). For the wells 920 in this example, the difference among the estimated Cl concentrations in the formation water for the landing target of parent wells 920 (e.g., well 920-1 through well 920-3) and child wells 920 (e.g., well 920-4 through well 920-9) may be up to 10%. The estimated formation water Cl concentration for the landing target of the parent well(s) 920 may be used to calculate volume fractions of fracturing fluid and formation water for the produced water source allocation of the parent well 920.

In certain example embodiments, one or more models, equations, formulas, and/or other forms of algorithms (e.g., algorithms 533) may be used to determine the ratio or amount of fracturing fluid found in produced water (e.g., a form of water 146) in one well 920 (e.g., well 920-2) when the fracturing fluid is used in a fracturing operation performed on another well 920 (e.g., well 920-4). For example, the volume of fracturing fluid produced through well 920-2 when the fracturing fluid is used in a fracturing operation performed on well 940-4 may be found by the following equation:

$$V = r \times f = r \times [(C_2 - C_3) \div (C_2 - C_1)], \quad (5)$$

where $C_1$ is the chlorine (Cl) concentration in the fracturing fluid used in the fracturing operation performed on well 920-4; $C_2$ is the Cl concentration in a sample (e.g., sample 447) taken from well 920-2 within one week prior to the start of the fracturing operation performed on well 920-4; $C_3$ is the Cl concentration in a sample (e.g., sample 447) taken from well 920-2 on a day during the fracturing operation performed on well 920-4; r is the water production rate (in BWPD) of well 920-2 on the sampling date; V is the fracturing fluid volume (in BWPD) produced in well 920-2 on the sampling date; and f is the fraction of fracturing fluid used in well 920-4 that appears in the produced water of well 920-2.

In some cases, the concentration of other elements (e.g., Na, K) found in the fracturing fluid used in the fracturing operation performed on one well 920 and in samples (e.g., samples 447) taken from another well 920 may be used in the above algorithms (or alternative algorithms) in addition to or instead of the concentration of Cl. In a different scenario, testing of samples (e.g., samples 447) obtained from a well 920 not undergoing a fracturing operation may show that the fracturing fluid contact/commingling with other water sources may have occurred before the fracturing fluid reaches that well. In such cases, a change in production rates of that well may be an indication of the effect of the fracturing fluid on that well. In other words, the fracturing fluid may not directly reach the other well, but instead the fracturing fluid may force other fluid(s) in the fractures/subsurface between the well whose samples are being tested and the well undergoing the fracturing operation to enter into the well whose samples are being tested.

FDI/parent-child interaction due to fracturing operation of child well 920-4 through child well 920-9 may cause an increase in formation water production and a decrease in oil production, in addition to fracturing fluid production at the parent well 920-1 through parent well 920-3 during 100+ days since the end of the fracturing operation on the child wells 920. As an example, the graph 1097 of FIG. 10 shows the allocated daily production rates of formation water, fracturing fluid, and oil rate over time for parent well 920-1. During the first 11 days since well 920-1 returned to production after being shut in during the fracturing operation on the child well 920-4 through child well 920-9, the rate of produced water in the samples (e.g., samples 447) is approximately 5-6 times higher than the rate prior to the shut in period (coinciding with the fracturing operation).

Also, the allocated rate of formation water is approximately 3.5 times greater than the produced water rate prior to the fracturing operation, and the allocated rate of fracturing fluid production is approximately 2-3 times greater than the produced water rate prior to the fracturing operation. During the first 95 days of the well 920-1 returning to production after the fracturing operation, the cumulative formation water production at well 920-1 is approximately 2.5 times greater than the cumulative fracturing fluid production.

While the fraction of fracturing fluid in the collected samples of produced water from the parent wells 920 (e.g., well 920-1 through well 920-3) may be up to at least 45% and remain above 20% for approximately 3 months, the produced water from child wells 920 (e.g., well 920-4 through well 920-9) show dominating signatures of formation water since the initial flowback/production stage. The graph 1197 of FIG. 11 shows the Cl concentrations in the produced water of samples (e.g., samples 447) along with water and oil production rates over time for child well 920-4. The Cl concentration in the produced water in the first collected sample from well 920-4 is approximately 70,000 mg/L, which is 40+ times higher than the Cl concentration (1570 mg/L) in the fracturing fluid.

There is slight fluctuation but no significant change in produced water compositions during the first 2 months that the well 920-4 is put on production. On Day 77 since well 920-4 is put on production, there is a step increase in both Cl concentration in the produced water within samples (e.g., samples 447) along with a step decrease in water rate and water cut. After Day 77, well 920-4 shows a steady decrease in water cut, and the Cl concentration level in the produced water is substantially flat without significant changes until the well 920-4 experiences a FDI due to a fracturing operation applied to well 920-4 and well 920-5. The produced water composition during this second stage may be representative of formation water chemistry in the landing target of well 920-4. The calculated fraction of fracturing fluid is 6%-16% during the first stage and 0%-5% for the second stage. The graph 1297 of FIG. 12 shows the allocated rates of formation water and fracturing fluid production at well 920-4 during the same time period.

The graph 1397 of FIG. 13 plots the cumulative fraction of fracturing fluid produced at individual child well 920-4 through child well 920-9 over the first 100 days that those wells 920 are put on production. Well 920-4 through well 920-6 show a substantially similar fracturing fluid return profile. Specifically, the cumulative fracturing fluid produced at individual wells 920 during the first 100 days in this example are calculated to be 3.5%-3.7% of the total amount of fracturing fluid injected in the wells 920 during the completion stage. For well 920-7 through well 920-9, the fracturing fluid return for well 920-8 and well 920-9 are substantially the same as each other and are higher than the fracturing fluid return for well 920-4 through well 920-7.

The cumulative fraction of fracturing fluid return at well 920-7 for the first 100 days is only ~0.7%, which is lower than that for all other 5 wells 920. The low fracturing fluid return at well 920-7 and the relatively high fracturing fluid return at well 920-8 and well 920-9 are likely due to the fact that the put on production date for well 920-8 was 54 days later than that for the other 5 wells 920 shown in the graph 1397. The graph 1497 of FIG. 14 shows the total cumulative fracturing fluid return from well 920-7 through well 920-9 is similar to total cumulative fracturing fluid return from well 920-4 through well 920-6. The very similar fracturing fluid return profile is likely due to the same fracturing design for all 6 of the wells 920 on the same pad.

The graph 1597 of FIG. 15 plots the cumulative production of formation water over days put on production for well 920-7 through well 920-9, and the graph 1697 of FIG. 16 plots the cumulative oil production over the days put on production for well 920-7 through well 920-9. The formation water production for well 920-8 in this case is slightly higher than the formation water production for well 920-9, and is more than twice the formation water production for well 920-7 during the first 100 days on production. The relatively low water production for well 920-7 is likely due to the 54 days delay on putting well 920-7 on production compared to the other wells 920. Oil production is lower for well 920-8 compared to the oil production for well 920-7 and well 920-9. Based on analysis of oil production and allocated formation water production data, the water saturation at the landing target of well 920-8 may be estimated to be 4+% higher than the average water saturation of wells 920-7 through well 920-9 in this example.

The graph 1797 of FIG. 17 plots the total cumulative production of formation water, and the graph 1897 of FIG. 18 plots the ratio of total cumulative oil to total cumulative formation water for well 920-7 through well 920-9 and for well 920-4 through well 920-6. While the total formation water production for well 920-7 through well 920-9 is very close to that for well 920-4 through well 920-6, the ratio of total cumulative oil to total cumulative water is lower for well 920-7 through well 920-9 compared to the same ratio for well 920-4 through well 920-6. Analysis based on cumulative formation water production and oil production data of the well 920-10 and well 920-11 may suggest the water saturation is 10+% higher for well 920-7 through well 920-9 compared to for well 920-4 through well 920-6.

In this example, a substantial amount of fracturing fluid may be produced from all three parent wells (parent well 920-1 through parent well 920-3) prior to the child wells (child well 920-4 through child well 920-9) being put into production. The graph 1997 of FIG. 19 plots the allocated daily fracturing fluid production over time for well 920-1 through well 920-9 starting at the end of the fracturing operation for well 920-4 through well 920-9. During the fracturing operation, well 920-1 through well 920-3 were shut in and then returned to production the day after the fracturing operation ended.

During the first 3 months after the fracturing operation ended, the fracturing fluid production was similar for well 920-1 and well 920-2. The cumulative fracturing fluid production for well 920-3 is about 50% of that at well 920-2 during that time. The peak fracturing fluid production rates at the child well 920-4 through child well 920-7 and child well 920-9 are substantially the same as or lower than the peak fracturing fluid return rate for well 920-3. Well 920-8 is put on production 54 days later than child well 920-5 through 920-9. The peak fracturing fluid return rate for well 920-4 is lower than the peak fracturing fluid return rate for each of well 920-5 through well 920-9. The graph 1997 indicates that the fracturing fluid present in the generated fracture networks may get produced by multiple wells 920 in this case. The fracturing fluid return at an individual well 920 may largely depend on when it was returned to production. The graph 1997 may indicate that the earlier the return-to-production date for a well 920, the higher the fracturing fluid production from the well 920.

In some cases, the fracturing fluid/rock-water interaction may play a key role in unlocking hydrocarbon production from shale and tight formations. To optimize the efficiency of a hydraulic fracturing operation for improving oil recovery, it may be important to appropriately manage fracturing fluid production at parent wells 920 (e.g., parent well 920-1 through parent well 920-3) to ensure sufficient contact between the fracturing fluid and the effective pay zone. Instant fracturing fluid production from parent wells 920 during fracturing operations and prior to returning child wells 920 to production may potentially decrease the effectiveness of the fracturing operation and oil productivity at the parent wells 920, such as is shown in the graph 1097 of FIG. 10 discussed above.

Produced water chemistry surveillance data, as described herein using example embodiments, suggest subsurface water heterogeneity in this region. Produced water from well 920-8 consistently shows highly distinguishable chemistry signatures both in terms of ion ratios (e.g., Ca/Mg as shown in the graph 2097 of FIG. 20) and ion concentrations (e.g., Mg as shown in the graph 2197 of FIG. 21) from all other wells 920, indicating possible presence of a different water source near the landing target of well 920-8. This appears consistent with the data in this example, which supports that water saturation at the landing target of well 920-8 is estimated to be 4+% higher than the average water saturation for well 920-7 and well 920-9.

Example embodiments may also be used to track and forecast water saturation in the formation based on produced water source allocation. For example, the graph 2297 of FIG. 22 shows the ratio of cumulative formation water production to the sum of the cumulation of oil production and the cumulative formation water production for child well 920-4 through child well 920-6 and for child well 920-7 through child well 920-9. As another example, the graph 2397 of FIG. 23 shows the ratio of the difference between the cumulative formation water production for child well 920-4 through child well 920-6 and the cumulative formation water production for child well 920-7 through child well 920-9, and the sum of the cumulation of oil production and the cumulative formation water production for child well 920-4 through child well 920-6 and for child well 920-7 through child well 920-9.

As the ratio of the fracturing fluid in the produced water within samples (e.g., samples 447) decreases over time, the produced water becomes more representative of formation water near the landing target for the well 920. The child wells 920 may be categorized into 3 groups based on similarity of the stabilized produced water chemistry. Group (1) is well 920-8. Group (2) is well 920-5 and well 920-5. Group (3) is well 920-7, well 920-9, and well 920-6. In this example, the produced water within samples (e.g., samples 447) from well 920-6 shows more similar chemistry signatures to the chemistry signatures of the produced water of well 920-5 during the first week on production and becomes more similar to the chemistry signatures of the produced water in samples (e.g., samples 447) of well 920-9 over time.

The graph 2497 of FIG. 24 shows the allocated daily production rates of formation water, fracturing fluid, and oil rate over time for a child well 920-4. A fracturing operation of well 920-10 and well 920-11 is shown in the graph 2497 to have occurred during approximately days 165-170 of well 920-4 being put on production. Before (e.g., during the initial flowback/production stage), during, and after the fracturing operation, formation water production dominates relative to the production of oil and fracturing fluid. Formation water and fracturing fluid production decreased and water cut decreased over time until the beginning of the fracturing operation. Immediately after the fracturing operation starts, the oil production at well 920-4 drops to 0, and the production rates of both formation water and fracturing fluid increases substantially with the formation water production at higher rate than the fracturing fluid production.

On approximately day 186, well 920-4 resumes production of oil and has a step decrease in production of both formation water and fracturing fluid. From there, the water production and water cut continue to decrease over time. The results show the fracturing fluid volume produced from well 920-4 at a later production stage due to fracture-driven interaction during the fracturing operation of well 920-10 and well 920-11 is substantially higher than the fracturing fluid return at the earlier stage (prior to the fracturing operation).

Using a mechanistic model to assess the impact of the fracturing operation, the impact of FDI's on oil production may depend on the producing pressure of the impacted wells. As the formation depletes and pressure drops over time, later FDI's may result in a greater impact compared with the earlier FDI's. This is consistent with the comparison between the graph 1097 of FIG. 10 and the graph 2497 of FIG. 24, showing a relatively larger decrease in oil productivity, a higher water cut increase, and a longer lasting impact at the parent well 920-1 compared to child well 920-4. Optimizing well stacking/spacing and sequencing development/fracturing to minimize adverse impacts from FDI's may be accomplished using example embodiments to develop saltwater handling/disposal in certain formations and as formation pressure depletes over time.

Summarizing, using example embodiments, cumulative volumes of formation water and fracturing fluid production are determined for child and parent wells 920 in an 11-well configuration from the end of a fracturing operation of the child wells to 3+ months after the child wells are put on production. The difference in water saturation among landing targets/formations are quantitatively estimated based on an integrated analysis of time-lapse water geochemistry surveillance and production data. This Example illustrates that time-lapse produced water geochemistry surveillance according to example embodiments provides a cost-effective, diagnostic, and quantitative approach to investigate the evolution of in-situ water source allocation in the near wellbore region over time and provide an important reference to drive for improved understanding of reservoir drainage dynamics/recovery mechanisms and asset development optimizations. The derived produced water source allocation results according to example embodiments provide a basis to devise life-of-well production performance optimization strategy and produced water management for fractured wells.

The results of this example also show that FDIs may cause a sudden and substantial increase in both formation water and fracturing fluid production, along with decreased oil productivity at parent wells. Fracturing fluid volume produced at a well at later production stages due to fracture-driven interaction may be higher than the fracturing fluid return at initial flowback/production stages. With saltwater handling/disposal, example embodiments may be used to optimize well placement/development sequences to appropriately manage fracturing fluid production at parent wells and enable sufficient contact/interaction between fracturing fluid and the effective pay zone. Example embodiments may be used to avoid relatively larger fracturing fluid production from parent wells, which may jeopardize the effectiveness of a fracturing operation and subsequent oil productivity/well performance for both parent and child wells.

Figure 25:
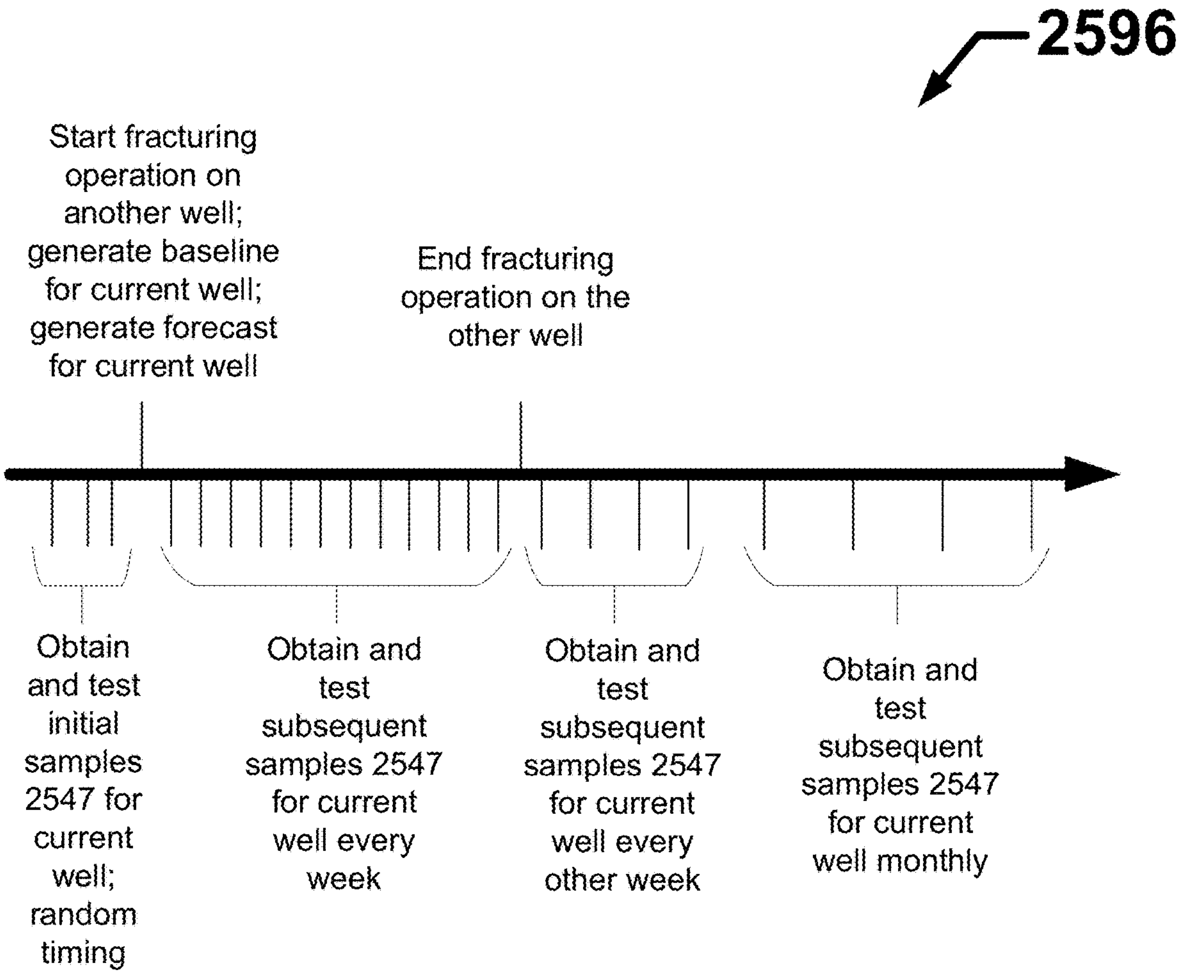
FIGS. 25 through 27 show examples of timelines that may be followed as to how often samples from a well are obtained and tested according to certain example embodiments.
Figure 26:
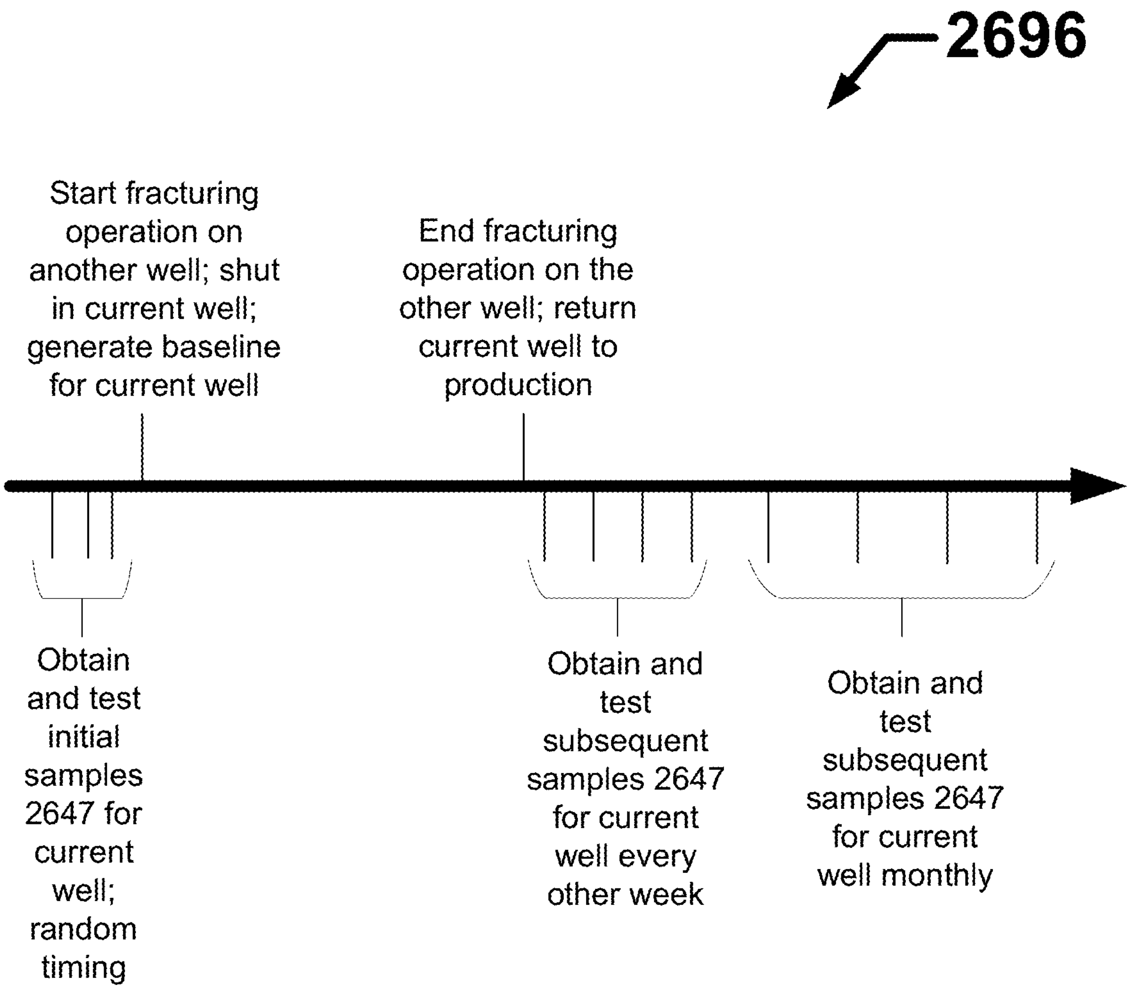
Figure 27:
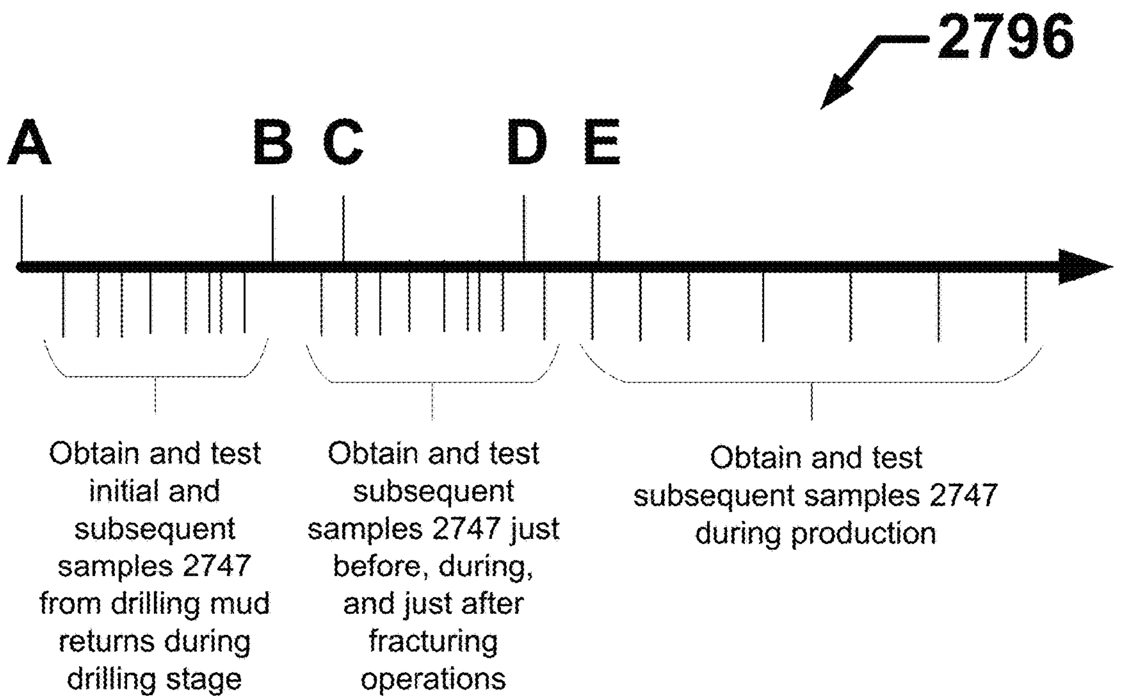

As discussed in the example above, the rate at which samples (e.g., samples 447) are obtained and tested for a particular well 920 in a network of wells may vary. FIGS. 25 through 27 show examples of timelines that may be followed as to how often samples from a well are obtained and tested according to certain example embodiments. Specifically, FIG. 25 shows a timeline 2596 of obtaining and testing samples 2547 for a current well (e.g., well 920-3) that remains in production while another well (e.g., well 920-6) undergoes a fracturing operation.

Referring to the description of the prior figures, as the timeline 2596 of FIG. 25 shows, before the fracturing operation of the other well begins, one or more (in this case, three) initial samples 2547 are obtained from the current well and tested. As a result, a controller (e.g., controller 404) of the example analytic system (e.g., example analytic system 450) generates a baseline of one or more of the parameters associated with the initial samples 2547 for the current well. The initial samples 2547 in this case are taken at random times, but other sampling rates may be used in alternative embodiments.

When the fracturing operation of the other well begins, the baseline of the current well is established. Also, a controller of the example analytic system may use the baseline and one or more models (e.g., forms of algorithms 533) to generate a forecast of the amount of certain parameters to be found in the samples 2547 from the current well during the fracturing operation. During the fracturing operation of the other well, subsequent samples 2547 are obtained from the current well and tested. The results of these tests during the fracturing operation of the other well are compared to the baseline and/or the forecast. In this case, the subsequent samples 2547 (12 in total in this example) are obtained from the current well and tested on a weekly basis during the fracturing operation of the other well among the group of wells. In alternative embodiments, the rate at which the subsequent samples 2547 are obtained from the current well and tested during the fracturing operation of the other well may be different (e.g., daily, every other day, every other week, randomly).

When the fracturing operation of the other well ends, additional subsequent samples 2547 are obtained from the current well and tested. The rate at which the additional subsequent samples 2547 are obtained from the current well and tested after the fracturing operation of the other well ends may be the same as, or different than, the rate at which the subsequent samples 2547 are obtained from the current well and tested during the fracturing operation of the other well. In this example, for the first month after the fracturing operation of the other well ends, the additional subsequent samples 2547 are obtained from the current well and tested every week. After that time, the additional subsequent samples 2547 are obtained from the current well and tested on a monthly basis. In alternative embodiments, the rate at which the additional subsequent samples 2547 are obtained from the current well and tested after the fracturing operation of the other well ends may be different (e.g., daily, every other day, every other week, randomly).

Referring now to FIG. 26, the timeline 2696 shows that, before the fracturing operation of the other well begins, one or more (in this case, three) initial samples 2647 are obtained from the current well and tested. As a result, a controller (e.g., controller 404) of the example analytic system (e.g., example analytic system 450) generates a baseline of one or more of the parameters associated with the initial samples 2647 for the current well. The initial samples 2647 in this case are taken at random times, but other sampling rates may be used in alternative embodiments.

In this example, just before the fracturing operation of the other well begins, the current well is shut in. When the fracturing operation of the other well begins, or around the time that the current well is shut in, the baseline of the current well is established. Also, a controller of the example analytic system may use the baseline and one or more models (e.g., forms of algorithms 533) to generate a forecast of the amount of certain parameters to be found in the samples 2647 from the current well after the fracturing operation ends. During the fracturing operation of the other well, no samples 2647 are obtained from the current well because the current well is shut in.

Around the time (e.g., shortly afterwards) that the fracturing operation of the other well ends, the current well is returned to production. After the current well is returned to production, subsequent samples 2647 are obtained from the current well and tested. The rate at which the subsequent samples 2647 are obtained from the current well and tested after the fracturing operation of the other well ends may vary. In this example, for the first month after the fracturing operation of the other well ends and the current well is returned to production, the subsequent samples 2647 are obtained from the current well and tested every week. After that time, the subsequent samples 2647 are obtained from the current well and tested on a monthly basis. In alternative embodiments, the rate at which the subsequent samples 2647 are obtained from the current well and tested after the fracturing operation of the other well ends may be different (e.g., daily, every other day, every other week, randomly).

As discussed above, the rate at which samples are obtained from a particular well and tested may vary at different stages and/or within different stages of operation of that well and/or other wells in the grouping. Table 2 below shows an example of a sampling schedule for existing and upcoming wells among well sharing a pad.

TABLE 2

| Time | Existing Wells | Upcoming Wells |
|---|---|---|
| Before a hydraulic fracturing operation | At least 3 samples (no set schedule) | N/A |
| During a hydraulic fracturing operation | 1 sample per week for wells not shut in | N/A |
| 0-2 months after end of hydraulic fracturing operation | 1 sample per week | N/A |
| 0-1 months after upcoming wells are put on production | 1 sample per month | 2 samples per week |
| 1-2 months after upcoming wells are put on production | 1 sample per month | 1 sample per week |
| 2-6 months after upcoming wells are put on production | 1 sample per month | 2 samples per month |
| 6-12 months after upcoming wells are put on production | 1 sample/2 months | 1 sample per month |
| 12-24 months after upcoming wells are put on production | 1 sample per year | 1 sample/3 months |
| 24+ months after upcoming wells are put on production | 1 sample per year | 1 sample per year |

FIG. 26 shows a timeline 2796 over the entire life of a well and how testing of water samples may be used according to example embodiments. Point A at the beginning of the timeline 2796 indicates when drilling of a well begins, and point B indicates when the drilling of the well is complete. Point C indicates when fracturing operations begin, and point D indicates when fracturing operations end. Point E indicates when production of the wellbore begins, and production operations continue through the end of the time captured in the timeline 2796.

Between point A and point B in the timeline 2796, water samples 2747 (both initial water samples 2747 used to establish a baseline and subsequent samples 2747) may be recovered from drilling mud returns during drilling operations for the wellbore. For example, when subsurface waterflow is encountered or suspected during drilling operations, mud filtrate samples 2747 may be collected to understand the potential source of waterflow and to support the optimization of fracturing design and asset development strategy. The analysis may include, for example, cation analysis, anion analysis, isotope analysis, and/or bacteria analysis.

As a specific example, multiple different samples 2747 may be taken for different purposes. In such a case, one sample 2747 may be or include collecting a filtrate from mud with no presence of subsurface water sources to serve as a baseline of mud filtrate. Another sample 2747 may be or include collecting a filtrate from returned mud with likely presence of encountered water. Such samples 2747 may be taken from different depths (e.g., TVD) as the wellbore is drilled, including from depth in the lateral sections of the wellbore.

Between point C and point D in the timeline 2796, the fracturing water may be a blend of different water sources. Samples of the fracture water blend may be collected and analyzed. In addition, or in the alternative, individual sources of fracture water may be collected and analyzed. In some cases, the samples 2747 collected during the timeframe that is proximate to and including between point C and point D may be derived from other non-fracturing related activities, including but not limited to completion operations. In other words, samples 2747 collected and analyzed after point B and before point E may be related to any of a number of field operations that may occur between when drilling ends and when the well is put on production.

From point E onward in the timeline 2796, the sample schedule may vary. For example, for the first month after the well is put on production (POP), water samples 2747 may be collected and analyzed twice per week. For the second month after the well is POP, water samples 2747 may be collected and analyzed once per week. For months 3-6 after the well is POP, water samples 2747 may be collected and analyzed twice per month. For months 7-12 after the well is POP, water samples 2747 may be collected and analyzed once per month.

Water samples 2747 from the drilling mud may be collected in one or more of any number of ways. For example, a filter press test may be run for each drilling mud sample to extract the water sample 2747. Water samples 2747 may be analyzed using one or more of a number of technologies. For example, water samples 2747 may be analyzed by ICP and/or IC for ion concentrations. In some cases, stable isotope analysis may be used on some or all of the water samples 2747.

Once the drilling operation is complete at time B, preparations are made for fracturing operations on the wellbore. Just before the fracturing operations begin at time C, additional samples 2747 are collected and tested. This collection and testing of samples 2747 continues throughout the fracturing operations and just after the fracturing operations end at time D. When production operations of the wellbore begin at time E, additional samples 2747 are collected and tested.

The frequency of collection and testing of water samples 2747 may vary. For example, during the drilling operations (between time A and time B in the timeline 2796), the collection and testing of water samples 2747 may be more frequent relative to the frequency of collection and testing of water samples 2747 during the fracturing operations (between time C and time D in the timeline 2796), which may be more frequent relative to the frequency of collection and testing of water samples 2747 during the production operations (after time E in the timeline 2796).

Figure 28:
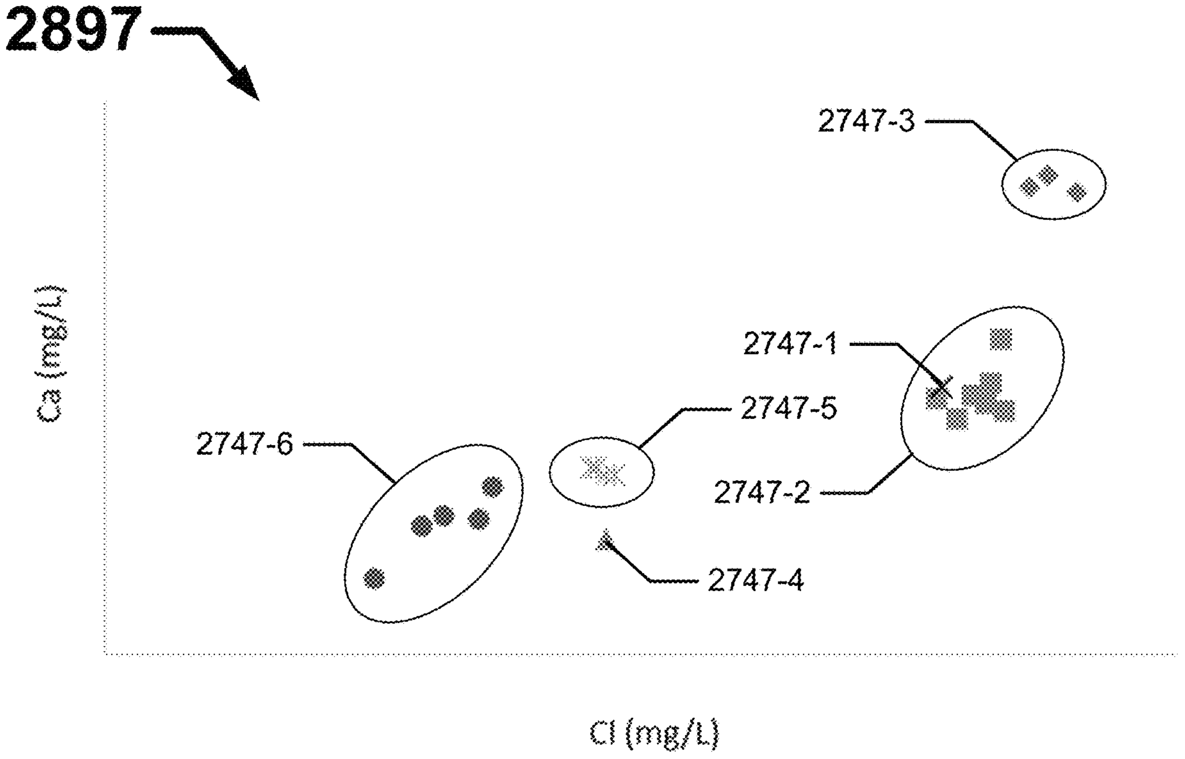
FIG. 28 shows a graph of results of samples collected and tested under the timeline of FIG. 27 according to certain example embodiments.

FIG. 28 shows a graph 2897 that plots data related to an example under the timeline 2796 of FIG. 27 to identify a water source during drilling operations of a wellbore. Specifically, the graph 2897 of FIG. 28 shows a plot of amounts of Ca (in mg/L) versus amounts of Cl (in mg/L) found in water samples 2747 collected and tested from 5 different depths (or range of depths) within a wellbore during drilling operations (between time A and time B in the timeline 2796 of FIG. 27). When subsurface waterflow is encountered or suspected during drilling, mud filtrate samples are collected and analyzed to understand a potential source of the waterflow. The water samples 2747 may be collected at different depths (e.g., total depth), and testing of the water samples 2747 may reveal a variation of water sources along different parts (e.g., the lateral or horizontal section) of the wellbore.

The initial water sample 2747-1 is among a group of water samples 2747-2 collected and sampled at a first depth (or range of depths) of the wellbore. Another group of water samples 2747-3 are collected and sampled at a second (lower) depth (or range of depths) of the wellbore. A water sample 2747-3 is collected and sampled at a third (lower) depth (or range of depths) of the wellbore. Another group of water samples 2747-3 are collected and sampled at a fourth (lower) depth (or range of depths) of the wellbore. Finally, another group of water samples 2747-3 are collected and sampled at a fifth (lower) depth (or range of depths) of the wellbore.

This collection and testing of the water samples 2747 during drilling operations may impact subsequent field operations on the wellbore. For example, collection and testing of the water samples 2747 during drilling operations may lead to a change in fracturing design (e.g., elect to not fracture certain lateral sections to reduce water production from untargeted formations). As another example, collection and testing of the water samples 2747 during drilling operations may lead to an updated understanding of subsurface water chemistry, which in turn may change the fracturing water chemistry (e.g., the fracturing water sourcing) and/or one or more of the fracturing chemical additives.

As yet another example, collection and testing of the water samples 2747 during drilling operations may lead to a shut-in of adjacent water injection wells to eliminate or minimize the negative impact of waterflow on well operations. As yet another example, collection and testing of the water samples 2747 during drilling operations may improve and/or update an understanding of landing a lateral of the wellbore before fracturing and/or production operations. For instance, the water samples 2747 in the form of mud filtrate in water phase collected from drilling mud returns during a drilling operation may show a similar water chemistry composition to the water samples 2747-2. It may be determined that such water chemistry composition is produced water that is not economic due to large quantities of water production. As a result, using the information obtained from water sample testing using example embodiments, a decision may be made to not fracture and/or produce from the well, even though the well is drilled.

Monitoring during a drilling operation may also lead to decision factors as to further development of a wellbore. For example, strong waterflow encountered during a drilling operation may be indicative of whether further development of the well, at least on the planned schedule and trajectory, is warranted. As another example, in collecting and analyzing water samples 2747 during drilling, the resulting water chemistry data may indicate the waterflow encountered during drilling of the lateral section of a development well is similar to the water chemistry of the water samples 2747-5 shown in the graph 2897 of FIG. 28.

In some cases, such as in a lateral section of a wellbore, samples that include oil-based mud may be collected and analyzed because the impact of the presence of mud in the water sample 2747 may be insignificant. In such a case, the water chemistry composition data for the base brine used to prepare the mud may be obtained. For example, when injection water channeling from adjacent SWD wells is identified during drilling, the analysis using example embodiments may lead to a decision not to fracture certain sections of the lateral for the wellbore being drilled in order to reduce water cut/water production from a development well. In such a case, an injection operation may need to be temporarily ceased or paused for a period of time.

Figure 29:
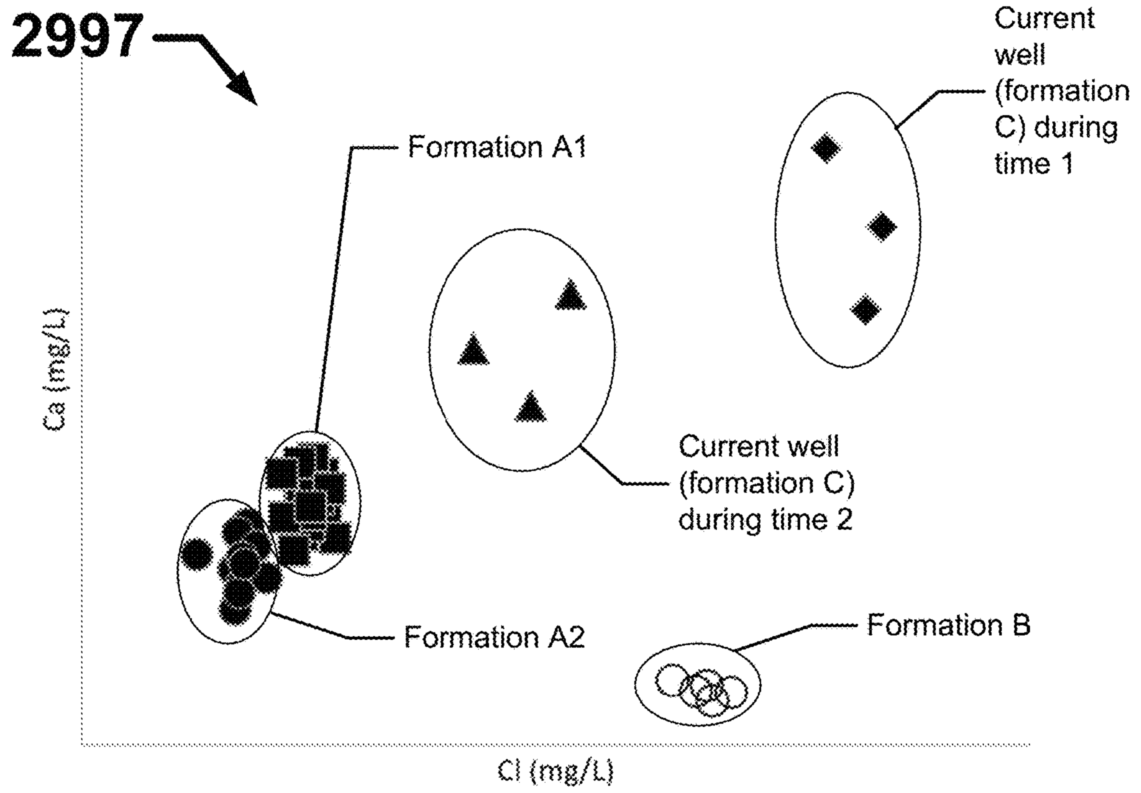
FIG. 29 shows a graph of a fluid flowing between wells according to certain example embodiments.

FIG. 29 shows a graph 2997 of a fluid flowing between wells according to certain example embodiments. Referring to the description of the prior figures, the graph 2997 of FIG. 29 shows a plot of amounts of Ca (in mg/L) versus amounts of Cl (in mg/L) found in samples (e.g., samples 447) from 3 different formations (formation A, formation B, and formation C). Formation A is subdivided into 2 parts (formation A1 and formation A2). The current well in this case is located in formation C. The graph 2997 shows that the water chemistry data indicates that a fluid (e.g., formation water, fracturing fluid) from formation A1 and formation A2 has traveled through fractures (e.g., fractures 101) to formation C and the current well.

Based on the data, the estimated fraction of fluid from formation A1 and formation A2 that appears in the level of Ca to Cl in the samples from the current well in formation C obtained during time 2 is approximately 50%-70% of the level of Ca to Cl in the samples from the current well in formation C obtained during time 1, which precedes time 2. In alternative embodiments, other ion concentrations (aside from Ca and/or Cl), ion ratios, stable isotope data (as shown in FIG. 30 below), and/or other parameters may be used to understand the effect of a field operation in one well on another well, whether the two wells are within the same formation, the same range of depths, etc.

Figure 30:
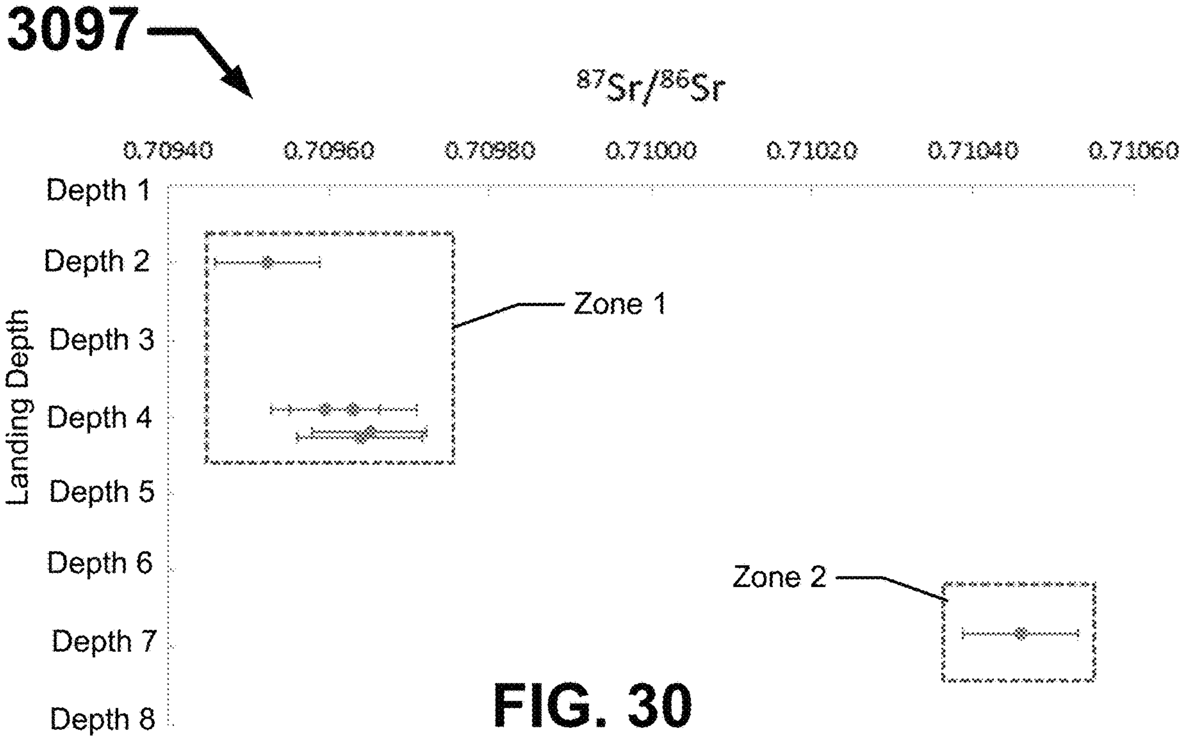
FIG. 30 shows a graph of isotope data according to certain example embodiments.

FIG. 30 shows a graph 3097 of isotope data according to certain example embodiments. Referring to the description of the prior figures, the graph 3097 of FIG. 30 plots ranges of isotope $^{87}Sr/^{86}Sr$ found in samples (e.g., samples 447) in two different zones (zone 1 and zone 2). In this case, zone 1 is closer to the surface compared to zone 2. In this example, the range of ratios of the isotope measured in the samples from the one or more wells in zone 1 are lower than the range of the ratio of the isotope measured in the samples from the one or more wells in zone 2.

Testing and analysis of geochemistry data of samples (e.g., samples 447) from wells (e.g., wells 420) may be used to apply to one or more of a number of operational objectives relative to the wells. Examples of such objectives may include, but are not limited to, identification and allocation of produced water sources; fracture driven interaction/well interaction studies; scaling risk assessment and management; reservoir surveillance, drainage diagnostics, and recovery mechanisms; well performance root cause analysis; improved understanding of water saturation characterization; optimize placement and completion design of new producing wells and/or SWD; optimize key decision making in Shale & Tight asset development; and optimize reservoir simulation and production/reserves forecasts.

Example embodiments may be designed to utilize water chemistry data, water/oil/gas production rates, gas-oil ratio, water cut, other surveillance data, data analytics, and/or other information to monitor the effects of a hydraulic fracturing operation on other wells and quantify real-time fluid communication between wells. Different methodologies may be used to achieve a reliable forecast. As an example, a database/dashboard may be used to integrate water chemistry data, daily water/oil/gas production rates, and linkage to information about individual wells and identify/analyze the effect of fracturing operations and fluid communication and/or drainage volume communication between wells.

The information about the existing (parent) wells and the relatively new (child) wells (e.g., wells undergoing a hydraulic fracturing operation) may include, but is not limited to, well history/location/formation/completion design. The volume of fracturing fluid and/or other fluid in the formation that communicates with other wells by the fracturing fluid that enters the fracture network of existing/parent wells from the one or more wells undergoing the fracturing operation may be estimated based on the collected produced water chemistry data and production rates of existing/parent wells before/during/after the fracturing operation. Rock-fluid interaction on water chemistry may be taken into consideration when interpreting the water data and may be used to calibrate the estimation as needed. The water chemistry parameters used for calculation may include, but are not limited to, ion concentrations (e.g., Cl, Ca, K, Na, Mg), ion ratios (e.g., Na/K, Ca/Mg, Cl/Ca), and/or stable isotopes (e.g., $^{87}Sr/^{86}Sr$, or any other ions). Produced water compositions may stabilize over time and possibly represent formation water produced from the intended zone for landing and completion. Such produced water may refer to stabilized produced water, or the estimated formation water produced from a well.

The database and/or dashboard may be updated over time and may be used as one reference to optimize well placement (landing/spacing), completion design, reservoir simulation and/or modeling, and decision making in asset development. Artificial intelligence and machine learning may be used to help process and/or interpret the information and/or results obtained in the data dashboard for different applications. Example embodiments may additionally or alternatively be used to optimize reservoir modeling, simulation, and/or earth modeling. An example of an outline for a database according to example embodiments is shown below with respect to Table 3.

TABLE 3

| Situation | Prior to hydraulic fracturing operation | During hydraulic fracturing operation | After hydraulic fracturing operation ends |
|---|---|---|---|
| New well(s) to be hydraulically fractured | Obtain fracturing fluid chemistry data | Obtain fracturing fluid chemistry data | Obtain produced water chemistry data and daily water, oil, and gas production rates |
| Existing well(s) not to be shut in during fracturing operation | Obtain produced water chemistry data and daily water, oil, and gas production rates | Obtain produced water chemistry data and daily water, oil, and gas production rates | Obtain produced water chemistry data and daily water, oil, and gas production rates |
| Existing well(s) to be shut in during fracturing operation | Obtain produced water chemistry data and daily water, oil, and gas production rates | Not Applicable | Obtain produced water chemistry data and daily water, oil, and gas production rates |

Figure 31:
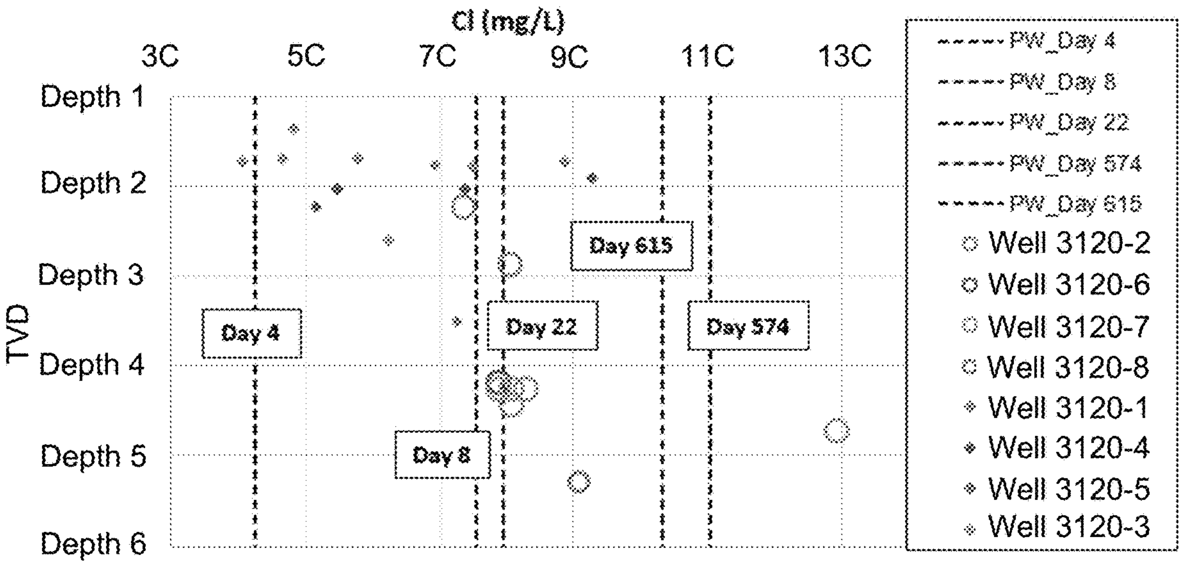
FIG. 31 shows a graph of chlorine concentrations time lapsed over one or more wells according to certain example embodiments.

FIG. 31 shows a graph 3197 of chlorine concentrations time lapsed over multiple wells according to certain example embodiments. Referring to the description of the prior figures, the graph 3197 shows that on day 4 of the sampling and testing period, the produced formation water (part of a sample) may predominately be water from well 3120-1, well 3120-2, and well 3120-3, which are at a shorter TVD and which have lower concentrations of Cl. On day 8 and day 22, the Cl levels in the produced formation water are close to the Cl levels in samples obtained from well 3120-6 and well 3120-7. On day 574 and day 615, the Cl levels in the produced formation water may be outside the available formation water Cl range of well 3120-1 through well 3120-5, and so contributions from non-targeted formation zones such as well 3120-7 may be suspected.

Example embodiments may be used to provide systems and methods for evaluating one or more wells using water chemistry analysis. Example embodiments may provide a number of benefits. Such benefits may include, but are not limited to, optimizing well performance, optimizing hydraulic fracturing operations, optimizing saltwater disposal operations, optimizing injection and production wells, utilizing geothermal resources, greater ease of use, extending the life of a well (including both parent wells and child wells), flexibility, configurability, and compliance with applicable industry standards and regulations.

Although embodiments described herein are made with reference to example embodiments, it should be appreciated by those skilled in the art that various modifications are well within the scope of this disclosure. Those skilled in the art will appreciate that the example embodiments described herein are not limited to any specifically discussed application and that the embodiments described herein are illustrative and not restrictive. From the description of the example embodiments, equivalents of the elements shown therein will suggest themselves to those skilled in the art, and ways of constructing other embodiments using the present disclosure will suggest themselves to practitioners of the art. Therefore, the scope of the example embodiments is not limited herein.

What is claimed is:

1. A method for identifying a source of produced water in a formation using water chemistry analysis, the method comprising:

testing, using a testing apparatus and a sensor device of an analytic system, a plurality of water chemistry parameters associated with a first sample obtained from each of a plurality of wells in the formation over a period of time prior to implementing a field operation of a well of the plurality of wells in the formation, wherein each first sample comprises water from multiple sources, wherein each first sample is delivered from the plurality of wells in the formation to the analytic system using a conveyance network, and wherein the plurality of water chemistry parameters associated with the first sample comprises at least one of a group consisting of an ion concentration, an ion ratio, and an amount of a stable isotope;

generating, using a controller of the analytic system and based on results of testing the plurality of water chemistry parameters associated with each first samples, a baseline of at least one of the plurality of water chemistry parameters associated with the first sample for each of the plurality of wells in the formation;

testing, using testing apparatus and the sensor device of the analytic system, the plurality of water chemistry parameters associated with a second sample obtained from each of the plurality of wells in the formation during the field operation of the well, wherein the second sample comprises water from the multiple sources, and wherein each second sample is delivered from the plurality of wells in the formation to the analytic system using the conveyance network;

determining, using the controller of the analytic system, a difference in the plurality of water chemistry parameters associated with the second sample between the baseline and results of testing the second sample for at least one of the plurality of wells in the formation, wherein the difference exceeds a threshold parameter value for the at least one of the plurality of water chemistry parameters associated with the second sample, wherein the difference comprises a characterization of water chemistry, and wherein the characterization of water chemistry establishes reservoir drainage dynamics of the well; and generating, using the controller of the analytic system and based on determining the difference, a composition of a field operation fluid for injection into the well during a field operation, wherein the composition of the field operation fluid for injection results by controlling an amount of a fluid component of the field operation fluid for injection that is provided by a fluid component source, and wherein the composition of the field operation is used to enhance operational effectiveness with respect to the well based on the reservoir drainage dynamics of the well.

2. The method of claim 1, further comprising:

comparing, using the controller of the analytic system, the results of testing the second sample to expected results generated by a forecasting model of the analytic system;

determining, using the controller of the analytic system, that a second difference between the results and the expected results exceeds a threshold forecast value; and generating, using the controller of the analytic system, a revision to the forecasting model based on the second difference.

3. The method of claim 2, wherein the second difference comprises a fracturing fluid fraction of the at least one of the plurality of wells in the formation, wherein the revision to the forecasting model comprises extending an amount of days on production for the at least one of the plurality of wells in the formation when the threshold parameter value is greater than a threshold value, wherein the revision to the forecasting model comprises reducing an amount of days on production for the at least one of the plurality of wells in the formation when the threshold parameter value is less than the threshold value, and wherein the threshold value is 40%.

4. The method of claim 2, wherein at least one well of the plurality of wells in the formation is a geothermal resource, wherein the field operation comprises injecting the field operation fluid for injection into the at least one well to utilize the geothermal resource.

5. The method of claim 1, wherein the results of testing the parameter associated with the second sample indicates a volume of the field operation fluid for injection that is found in at least one of a remainder of the plurality of wells in the formation.

6. The method of claim 1, further comprising:

recommending, using the controller of the analytic system, a change to the field operation based on the difference, wherein the change comprises altering at least one of a group consisting of a duration of the field operation, a chemical composition of the field operation fluid, a flow rate, a pressure, and a temperature of the field operation fluid for injection.

7. The method of claim 6, further comprising:

testing, using the testing apparatus and the sensor device of the analytic system, the water chemistry parameter associated with a third sample obtained from each of the plurality of wells in the formation during the field operation of the well after the change has been implemented, wherein the third sample comprises water; and determining, using the controller of the analytic system, an additional difference in the water chemistry parameter between the baseline and results of testing the third sample for at least one of the plurality of wells in the formation, wherein the additional difference exceeds the threshold parameter value for the water chemistry parameter associated with the third sample, and wherein the additional difference comprises an additional characterization of water chemistry.

8. The method of claim 1, wherein at least one well of the plurality of wells in the formation is an injection well, wherein the field operation comprises injecting saltwater into the at least one well of the plurality of wells in the formation.

9. The method of claim 1, further comprising:
controlling a fluid component source to regulate the composition of the field operation fluid for injection into the well during the field operation.

10. The method of claim 1, wherein at least one of the plurality of wells in the formation is shut in during the period of time prior to implementing the field operation of the well or during the field operation of the well.

11. The method of claim 1, further comprising:
generating, using the controller of the analytic system, a model that provides the expected results using the baseline; and
applying, using the controller of the analytic system, the model to another plurality of wells in a separate geographic location having a similar subterranean formation relative to the plurality of wells.

12. The method of claim 1, further comprising:
generating, after completing the field operation and using the controller of the analytic system, a recommendation for a subsequent well added to the plurality of wells in the formation, wherein the recommendation for the subsequent well comprises a placement of the subsequent well and a completion design of the subsequent well.

13. The method of claim 1, further comprising:
generating, based on testing the water chemistry parameter and using the controller of the analytic system, a forecasting model for at least one of the plurality of wells in the formation.

14. The method of claim 1, further comprising:
calibrating, by the controller of the analytic system and using the baseline, a forecasting model for at least one of the plurality of wells in the formation.

15. The method of claim 1, wherein the formation is an unconventional formation.

16. A system for identifying a source of produced water in a formation using water chemistry analysis, the system comprising:
a plurality of wells in the formation from which initial samples and subsequent samples are obtained;
a fluid source that is configured to provide a field operation fluid that is used in a field operation for one of the plurality of wells in the formation; and
an analytic system comprising:
a testing apparatus configured to:
test, using the water chemistry analysis, a plurality of water chemistry parameters associated with the initial sample obtained from each of the plurality of wells in the formation over a period of time prior to implementing the field operation for the one of the plurality of wells in the formation, wherein the initial sample comprises water from multiple sources, wherein each initial sample is delivered from the plurality of wells in the formation to the analytic system using a conveyance network, and wherein the plurality of water chemistry parameters comprises at least one of a group consisting of an ion concentration, an ion ratio, and an amount of a stable isotope; and
test, using the water chemistry analysis, the plurality of water chemistry parameters associated with the subsequent samples obtained from the plurality of wells in the formation during the field operation of the one of the plurality of wells in the formation, wherein the subsequent samples comprise water from the multiple sources, wherein each subsequent sample is delivered from the plurality of wells in the formation to the analytic system using the conveyance network; and
a controller communicably coupled to the testing apparatus, wherein the controller is configured to:
generate, based on results of testing the plurality of water chemistry parameters associated with each initial samples sample, a baseline of the plurality of water chemistry parameters associated with the initial sample for each of the plurality of wells in the formation;
determine a difference in the plurality of water chemistry parameters associated with the initial sample between the baseline and results of testing the subsequent samples for at least one of the plurality of wells in the formation, wherein the difference exceeds a threshold parameter value for at least one of the plurality of water chemistry parameters associated with the initial sample, wherein the difference comprises a characterization of water chemistry, and wherein the characterization of water chemistry establishes reservoir drainage dynamics of the well;
generate, based on determining the difference, a composition of the field operation fluid from the fluid source for injection into the one of the plurality of wells in the formation during the field operation, wherein the composition of the field operation fluid results by controlling an amount of a fluid component of the field operation fluid that is provided by a fluid component source, and wherein the composition of the field operation is used to enhance operational effectiveness with respect to the well based on the reservoir drainage dynamics of the well.

17. The system of claim 16, wherein the testing apparatus of the analytic system comprises:
a sensor device configured to measure the plurality of water chemistry parameters parameter associated with each initial sample samples and each subsequent sample samples obtained from the plurality of wells in the formation.

18. The system of claim 16, wherein the testing apparatus is further configured to test the field operation fluid obtained from at least one of the plurality of wells in the formation during the field operation of the one of the plurality of wells in the formation.

19. The system of claim 16, wherein the field operation fluid provided by the fluid source is adjusted during the field operation based on a recommendation made by the controller of the analytic system.

20. A method for identifying a source of produced water in a well within a formation using water chemistry analysis, the method comprising:
testing, using a testing apparatus and a sensor device of an analytic system, a plurality of water chemistry parameters associated with a plurality of first samples obtained from the well within the formation over a period of time prior to implementing a field operation, wherein the plurality of first samples comprises water from multiple sources, wherein each initial sample is delivered from the well within the formation to the analytic system using a conveyance network, and wherein the plurality of water chemistry parameters associated with the plurality of first samples comprises at least one of a group consisting of an ion concentration, an ion ratio, and an amount of a stable isotope;

generating, using a controller of the analytic system and based on results of testing the plurality of water chemistry parameters associated with the plurality of first samples, a baseline of at least one of the plurality of water chemistry parameters associated with the plurality of first samples for the well within the formation;

testing, using the testing apparatus and the sensor device of the analytic system, the plurality of water chemistry parameters associated with a second sample obtained from the well within the formation during the field operation, wherein the second sample comprises water from the multiple sources, and wherein the second sample is delivered from the well within the formation to the analytic system using the conveyance network;

determining a difference in the parameter between the baseline and results of testing the second sample for the well, wherein the difference exceeds a threshold parameter value for the parameter, and wherein the difference comprises a characterization of water saturation chemistry, and wherein the characterization of water chemistry establishes reservoir drainage dynamics of the well within the formation; and generating, using the controller of the analytic system and based on determining the difference, a composition of a fluid for injection into the well within the formation during the field operation, wherein the composition of the field operation fluid results by controlling an amount of a fluid component of the field operation fluid that is provided by a fluid component source, and wherein the composition of the field operation is used to enhance operational effectiveness with respect to the well within the formation based on the reservoir drainage dynamics of the well within the formation.

* * * * *